US010047344B2

(12) United States Patent
Poon et al.

(10) Patent No.: US 10,047,344 B2
(45) Date of Patent: Aug. 14, 2018

(54) BIOPHYSICALLY SORTED OSTEOPROGENITORS FROM CULTURE EXPANDED BONE MARROW DERIVED MESENCHYMAL STROMAL CELLS (MSCS)

(71) Applicants: Massachusetts Institute of Technology, Cambridge, MA (US); National University of Singapore, Singapore (SG)

(72) Inventors: Zhiyong Poon, Singapore (SG); Wong Cheng Lee, Singapore (SG); Krystyn J. Van Vliet, Cambridge, MA (US)

(73) Assignees: National University of Singapore, Singapore (SG); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/119,534

(22) PCT Filed: Feb. 18, 2015

(86) PCT No.: PCT/US2015/000029
§ 371 (c)(1),
(2) Date: Aug. 17, 2016

(87) PCT Pub. No.: WO2015/126528
PCT Pub. Date: Aug. 27, 2015

(65) Prior Publication Data
US 2017/0009208 A1 Jan. 12, 2017

Related U.S. Application Data

(60) Provisional application No. 61/941,081, filed on Feb. 18, 2014.

(51) Int. Cl.
*C12N 5/0775* (2010.01)
*A61K 35/28* (2015.01)
*A61K 35/12* (2015.01)
*C12N 5/077* (2010.01)

(52) U.S. Cl.
CPC ............ *C12N 5/0663* (2013.01); *A61K 35/28* (2013.01); *C12N 5/0654* (2013.01); *A61K 2035/124* (2013.01)

(58) Field of Classification Search
None
See application file for complete search history.

(56) References Cited

U.S. PATENT DOCUMENTS

| 7,118,746 | B1* | 10/2006 | Naughton | A61K 8/02 424/184.1 |
|---|---|---|---|---|
| 7,294,503 | B2 | 11/2007 | Quake et al. | |
| 7,309,486 | B1 | 12/2007 | Zamoyski | |
| 7,374,937 | B1* | 5/2008 | Prockop | C12N 5/0663 435/372 |
| 7,517,453 | B2 | 4/2009 | Bitensky et al. | |
| 8,186,913 | B2 | 5/2012 | Toner et al. | |
| 8,208,138 | B2 | 6/2012 | Papautsky et al. | |
| 9,458,489 | B2 | 10/2016 | Lim et al. | |
| 9,789,485 | B2 | 10/2017 | Han et al. | |
| 2007/0026381 | A1 | 2/2007 | Huang et al. | |
| 2007/0131622 | A1 | 6/2007 | Oakey et al. | |
| 2007/0263477 | A1 | 11/2007 | Sudarsan | |
| 2007/0264675 | A1 | 11/2007 | Toner et al. | |
| 2008/0128331 | A1 | 6/2008 | Lean et al. | |
| 2009/0014360 | A1 | 1/2009 | Toner et al. | |
| 2009/0050538 | A1 | 2/2009 | Lean et al. | |
| 2009/0053749 | A1 | 2/2009 | Manalis et al. | |
| 2009/0114607 | A1 | 5/2009 | Lean et al. | |
| 2009/0136982 | A1 | 5/2009 | Tang et al. | |
| 2009/0283452 | A1 | 11/2009 | Lean et al. | |
| 2010/0150880 | A1 | 6/2010 | Aubin et al. | |
| 2010/0314323 | A1 | 12/2010 | Lean et al. | |
| 2010/0314327 | A1 | 12/2010 | Lean et al. | |
| 2012/0028272 | A1 | 2/2012 | Sethu | |
| 2013/0011210 | A1 | 1/2013 | Toner et al. | |
| 2013/0109011 | A1 | 5/2013 | Park et al. | |
| 2013/0130226 | A1 | 5/2013 | Lim et al. | |
| 2014/0093867 | A1 | 4/2014 | Burke et al. | |
| 2014/0093952 | A1 | 4/2014 | Serway | |
| 2014/0154795 | A1 | 6/2014 | Lipkens et al. | |

(Continued)

FOREIGN PATENT DOCUMENTS

JP 2007-268490 10/2007
WO WO 2007/021409 A1 2/2007
WO WO 2007/081902 A3 7/2007

(Continued)

OTHER PUBLICATIONS

Kim et al., Stem Cells Dev. Nov. 1, 2012;21(16):2958-2968.*
Lee et al., Lab Chip. Apr. 7, 2011;11(7):1359-1367.*
Adams, A. A., et al., "Highly Efficient Circulating Tumor Cell Isolation from Whole Blood and Label-Free Enumeration Using Polymer-Based Microfluidics with an Integrated Conductivity Sensor," Journal of the American Chemical Society, 130(27): 8633-8641 (2008).
Allard, W.J., et al., "Tumor Cells Circulate in the Peripheral Blood of All Major Carcinomas but not in Healthy Subjects or Patients With Nonmalignant Diseases", Clin. Cancer Res., 10: 6897-6904 (Oct. 15, 2004).
Al-Soud, W.A. et al., "Purification and Characterization of PCR-Inhibitory Components in Blood Cells", Journal of Clinical Microbiology, 39(2): p. 485-493 (2001).

(Continued)

*Primary Examiner* — Daniel C Gamett
(74) *Attorney, Agent, or Firm* — Hamilton, Brook, Smith & Reynolds, P.C.

(57) ABSTRACT

The invention provides, inter alia, populations of large mesenchymal stem cells (MSC)(as well as conditioned medium from these cells) with enhanced regenerative potential, as well as methods of culturing and using these populations, such as therapeutic methods of mediating tissue repair or enhancing homing and engraftment of hematopoietic stem cells. These large MSC populations can, in certain embodiments, be produced by biophysically sorting an MSC-containing population.

20 Claims, 60 Drawing Sheets

(56) References Cited

U.S. PATENT DOCUMENTS

| | | | |
|---|---|---|---|
| 2015/0238963 | A1 | 8/2015 | Han et al. |
| 2017/0296732 | A1 | 10/2017 | Ebrahimi Warkiani et al. |

FOREIGN PATENT DOCUMENTS

| | | |
|---|---|---|
| WO | WO 2008/130977 A2 | 10/2008 |
| WO | WO 2010/115025 A2 | 10/2010 |
| WO | WO 2011/109762 A1 | 9/2011 |
| WO | WO 2013/116696 A1 | 8/2013 |
| WO | WO 2014/046621 A1 | 3/2014 |
| WO | WO 2015/057159 | 4/2015 |
| WO | WO 2015/126528 A1 | 8/2015 |
| WO | WO 2016/044537 | 3/2016 |
| WO | WO 2016/044555 | 3/2016 |

OTHER PUBLICATIONS

Antia, M., et al., "Microfluidic Approaches to Malaria Pathogenesis," Cellular Microbiology, 10(10): 1968-1974 (2008).
Asmolov, E.S., "The Inertial Lift on a Spherical particle in a Plane Poiseuille Flow at Large Channel Reynolds Number," Journal of Fluid Mechanics, 381: 63-87 (1999).
Atkin, S.L., et al., "Hypotonic Lysis of Red Blood Cell Contamination from Human Anterior Pituitary Adenoma Cell Preparations", In Vitro Cell Dev Biol Anim, 31(9): p. 657-658 (Oct. 1995).
Bhagat A.A.S., et al., "Enhancing Particle Dispersion in a Passive Planar Micromixer Using Rectangular Obstacles," Journal of Micromechanics and Microengineering. 18(8): 085005 (9 pp) (2008).
Bhagat AAS, et al. "Inertial Microfluids for Sheath-Less High-Throughput Flow Cytometry", Biomedical Microdevices, 12(2): 187-95 (2010).
Bhagat, "Inertial Microfluidics for Particle Separation and Filteration", Ph.D. thesis, College of Engineering, University of Cincinnati, 2009.
Bhagat, A.A.S., et al., "Continuous Particle Separation in Spiral Microchannels Using Dean Flows and Differential Migration", The Royal Society of Chemistry Lab on a Chip, 8(11): 1906-1914 (2008).
Bhagat, A.A.S., et al., "Inertial Microfluidics for Continuous Particle Filtration and Extraction", Microfluid Nanofluid 7: 217-226 (2009).
Bhagat, A.A.S., et al., "Pinched Flow Coupled Shear-Modulated Inertial Microfluidics for High-Throughput Rare Blood Cell Separation", The Royal Society of Chemistry Lab on a Chip, 11: 1870-1878 (2011).
Bhagat, A.A.S., et al., "Enhanced Particle Filtration in Straight Microchannels Using Shear-Modulated Inertial Migration," Physics of Fluids, 20: 101702 (4 pp) (2008).
Bhagat, A.A.S., et al., "Microfluidics for Cell Separation," Medical and Biological Engineering and Computing, 48: 999-1014 (2010).
Born, C., et al., "Estimation of Disruption of Animal Cells by Laminar Shear Stress," Biotechnology and Bioengineering, 40(9): p. 1004-1010 (1992).
Bruil, A., et al., "Asymmetric Membrane Filters for the Removal of Leukocytes from Blood", Journal of Biomedical Materials Research, 25(12): 1459-1480 (1991).
Chatterjee, A., et al., "Inertial Microfluidics for Continuous Separation of Cells and Particles", Proceedings of the SPIE, vol. 7929: 10 pgs. (2011).
Chin, C.D., et al., "Lab-On-A-Chip Devices for Global Health: Past Studies and Future Opportunities," Lab-on-a-Chip,7:41-57 (2007).
Choi, S., et al., "Microfluidic Self-Sorting of Mammalian Cells to Achieve Cell Cycle Synchrony by Hydrophoresis," Analytical chemistry,.81(5): 1964-1968 (2009).
Chun, B. et al., "Inertial Migration of Neutrally Buoyant Particles in a Square Duct: An Investigation of Multiple Equilibrium Positions", Physics of Fluids, 18(3): p. 031704 (2006).

Cooke, B.M., et al., "Falciparum Malaria: Sticking Up, Standing Out, and Out-Standing," Parasitology Today. 16(10): 416-420 (2000).
Cooper, S., "Rethinking Synchronization of Mammalian Cells for Cell Cycle Analysis," Cellular and Molecular Life Sciences, 60(6): 1099-1106 (2003).
Coupier, G., et al., "Noninertial Lateral Migration of Vesicles in Bounded Poiseuille Flow," Physics of Fluids. 20(11): 4 (2008).
Cranston, H.A., et al. "Plasmodium Falciparum Maturation Abolishes Physiologic Red Cell Deformability," Science. 223(4634): 400-403 (1984).
Cristofanilli, M., et a., "Circulating Tumor Cells, Disease Progression, and Survival in Metastatic Breast Cancer", N. Engl. J. Med., 351(8), 781-791 (Aug. 19, 2004).
Dean, W.R., LXXII. The Stream-Line Motion of Fluid in a Curved Pipe (Second Paper), The London, Edinburgh and Dublin Philosophical Magazine and Journal of Science,, Series 7, 5:30, 673-695 (1928).
Dean, W.R., XVI. Note on the Motion of Fluid in a Curved Pipe, The London, Edinburgh and Dublin Philosophical Magazine and Journal of Science, Series 7, 4(20): p. 208-223 (1927).
Delamarche, E., et al., "Stability of Molded Polydimethylsiloxane Microstructures," Advanced Materials, 9(9): 741-746 (1997).
Demirev, P.A., et al. "Detection of Malaria Parasites in Blood by Laser Desorption Mass Spectrometry," Analytical Chemistry. 74(14): 3262-3266 (2002).
Di Carlo D. "Inertial Microfluidics", The Royal Society of Chemistry Lab on a chip, 9(21):3038-46 (2009).
Di Carlo, D., et al., "Continuous Inertial Focusing, Ordering, and Separation of Particles in Microchannels", Proceedings of the National Academy of Sciences, 104(48): p. 18892-18897.
DiCarlo, D., et al., "Equilibrium Separation and Filtration of Particles Using Differential Inertial Focusing", Anal. Chem., 80(6): p. 2204-2211 (2008).
Dondorp, A.M., et al., "Abnormal Blood Flow and Red Blood Cell Deformability in Severe Malaria," Parasitology Today. 16(6): 228-232 (2000).
Downey, G .P., et al., "Retention of Leukocytes in Capillaries: Role of Cell Size and Deformability," Journal of Applied Physiology, 69(5): 1767-1778 (1990).
Evans, E., et al., "Static and Dynamic Rigidities of Normal and Sickle Erythrocytes," Journal of Clinical Investigation, 73(2):477-488 (1984).
Fan, R, et al., "Integrated Barcode Chips for Rapid, Multiplexed Analysis of Proteins in Microliter Quantities of Blood," Nature Biotechnology. 26(12): 1373-1378 (2008).
Fiebig, E, et al., "Rapid Leukocyte Accumulation by "Spontaneous" Rolling and Adhesion in the Exteriorized Rabbit Mesentery," International Journal of Microcirculation Clinical and Experimental. 10(2): 127-144 (1991).
Final Office Action dated Dec. 5, 2014 for U.S. Appl. No. 13/582,263, "Microfluidics Sorter for Cell Detection and Isolation".
Final Office Action dated Jan. 19, 2017 for U.S. Appl. No. 14/429,280, "Micro-Fluidic Device and Uses Thereof".
Final Office Action dated Oct. 16, 2015 for U.S. Appl. No. 13/582,263, "Microfluidics Sorter for Cell Detection and Isolation".
Fredriksson, K., et al., "Red Blood Cells Inhibit Proliferation and Stimulate Apoptosis in Human Lung Fibroblasts In Vitro, Scandinavian Journal of Immunology," 59(6): p. 559-565 (2004).
Fujiwara, H., et al., "Red Blood Cell Motions in High-Hematocrit Blood Flowing Through a Stenosed Microchannel," Journal of Biomechanics. 42(7): 838-843 (2009).
Gascoyne, P., et al. "Microsample Preparation by Dielectrophoresis: Isolation of Malaria," Lab on a Chip 2(2): 70-75 (2002).
Gleghorn, J.P., et al., "Capture of Circulating Tumor Cells from Whole Blood of Prostate Cancer Patients Using Geometrically Enhanced Differential Immunocapture (GEDI) and a Prostate-Specific Antibody," Lab on a Chip, 10(1): 27-29 (2010).
Glenister, F.K., et al., "Contribution of Parasite Proteins to Altered Mechanical Properties of Malaria-Infected Red Blood Cells," Blood, 99(3):1060-1063 (2002).

(56) References Cited

OTHER PUBLICATIONS

Goldsmith, H.L., et al., "Margination of Leukocytes in Blood Flow Through Small Tubes," Microvascular Research. 27(2): 204-222 (1984).
Goldsmith, H.L., et al., "Robin Fåhraeus: Evolution of his Concepts in Cardiovascular Physiology," American Journal of Physiology. 257(3): H1005-H1015 (1989).
Gossett, D.R., et al., "Label-Free Cell Separation and Sorting in Microfluidic Systems," Anal. Bioanal. Chem., 397:3249-3267 (2010).
Gupta, A, et al., "Effect of Aspect Ratio on Inertial Migration of Neutrally Buoyant Spheres in a Rectangular Channel," 47th AIAA Aerospace Sciences Meeting, Orlando, FL (Jan. 5-8, 2009).
Hampton, R.E., et al., "Migration of Particles Undergoing Pressure-Driven Flow in a Circular Conduit," Journal of Rheology, 41(3): 621 (1997).
Han, K and A.B. Frazier, "Lateral-Driven Continuous Dielectrophoretic Microseparators for Blood Cells Suspended in a Highly Conductive Medium", The Royal Society of Chemistry, Lab on a Chip, 8(7): 1079-1086 (2008).
Han, K.-H., et al., "Paramagnetic Capture Mode Magnetophoretic Microseparator for High Efficiency Blood Cell Separations", The Royal Society of Chemistry, 6(2): p. 265-273 (2006).
Herricks, T., et al., "Deformability Limits of Plasmodium Falciparum-Infected Red Blood Cells," Cellular Microbiology. 11(9): 1340-1353 (2009).
Ho, M., et al., "Visualization of Plasmodium Falciparum-Endothelium Interactions in Human Microvasculature: Mimicry of Leukocyte Recruitment," Journal of Experimental Medicine. 192(8): 1205-1211 (2000).
Hou, H.W., et al., "Microfluidic Devices for Blood Fractionation", Micromachines, 2(3): p. 319-343 (2011).
Hou, H.W., et al., "Deformability Based Cell Margination—A Simple Microfluidic Design for Malaria-Infected Erythrocyte Separation," Lab on a chip, 10(19): 2605-2613 (2010).
Hou, H.W., et al., "Deformability Study of Breast Cancer Cells Using Microfluidies," Biomedical Microdevices, 11(3): p. 557-564 (2009).
Huang, L.R., et al., "Continuous Particle Separation Through Deterministic Lateral Displacement", Science, 304: 987-990 (2004).
Hur, S.C., et al., "Deformability-Based Cell Classification and Enrichment Using Inertial Microfluidics", The Royal Society of Chemistry, Lab on a Chip, 11(5): 912-920 (2011).
Inglis, D.W., et al. "Continuous Microfluidic Immunomagnetic Cell Separation", Applied Physics Letters, 85(21): 5093-5095 (2004).
Jaeger, BAS, et al., "Abstract P2-01-02: Circulating Tumor Cells (CTC) may Express HER2/neu in Patients With Early HER2/neu Nagative Breast Cancer—Results of the German Success C Trial", Cancer Research, 72(24 Suppl): Abstract nr P2-01-02 (2012).
Jäggi, R.D., et al., "Microfluidic Depletion of Red Blood Cells from Whole Blood in High-Aspect-Ratio Microchannels," Microfluidics and Nanofluidics. 3(1): 47-53 (2007).
Jain, A., et al., "Determinants of Leukocyte Margination in Rectangular Microchannels," PLoS One. 4(9):e7104 (8 pp) (2009).
Karl, S., et al., "Enhanced Detection of Gametocytes by Magnetic Deposition Microscopy predicts higher potential for Plasmodium Falciparum Transmission," Malaria Journal. 7(1): 66 (2008).
Kim, U., et al., "Selection of Mammalian Cells Based on Their Cell-Cycle Phase Using Dielectrophoresis," Proceedings of the National Academy of Sciences, 104(52): 20708 (2007).
Kuntaegowdanahalli, S.S., et al., "Inertial microfluidics for continuous particle separation in spiral microchannels", The Royal Society of Chemistry, Lab on a Chip, 9(20): 2973-2980 (2009).
Lara, O., et al., "Enrichment of Rare Cancer Cells Through Depletion of Normal Cells Using Density and Flow-Through, Immunomagnetic Cell Separation," Experimental hematology, 32(10): 891-904 (2004).
Lee, S.S., et al., "Extensional Flow-Based Assessment of Red Blood Cell Deformability Using Hyperbolic Converging Microchannel," Biomedical Microdevices, (2009).
Lincoln, B., et al., "Deformability-Based Flow Cytometry," Cytometry Part A, 59(2): 203-209 (2004).
Marinkovic, M., et al., "Febrile Temperature Leads to Significant Stiffening of Plasmodium Falciparum Parasitized Erythrocytes," American Journal of Physiology—Cell Physiology. 296(1):C59-C64 (2009).
Matas, J.-P., et al., "Inertial Migration of Rigid Spherical Particles in Poiseuille Flow," Journal of Fluid Mechanics, 515: 171-195 (2004).
Matas, J.P., et al., "Lateral Forces on a Sphere," Oil & Gas Science and Technology, 59(1): 59-70 (2004).
McDonald, J.C., et al., "Poly(dimethylsiloxane) as a Material for Fabricating Microfluidic Devices," Accounts of Chemical Research. 35(7): 491-499 (2002).
Members of the Toxicogenonics Research Consortium, "Standardizing Global Gene Expression Analysis Between Laboratories and Across Platforms", Nature Methods, 2(5): p. 351-356 (May 2005).
Metzner, K., et al., "Abstract 3619: The Absence of Cleaved Caspase-3 in Circulating Tumor Cells Detected Using a Non-Enrichment Based Assay", Cancer Res., 72, Supplement 1 (2012).
Migita, S., et al., "Cell Cycle and Size Sorting of Mammalian Cells Using a Microfluidic Device," Analytical Methods, 2: 657-660 (2010).
Mohamed, H., et al., "Isolation of Tumor Cells Using Size and Deformation," Journal of Chromatography A, 1216(47): 8289-8295 (2009).
Nagrath, S., et al., "Isolation of Rare Circulating Tumour Cells in Cancer Patients by Microchip Technology," Nature, 450(7173): 1235-1239 (2007).
Nash, G.B., et al., "Abnormalities in the Mechanical Properties of Red Blood Cells Caused by Plasmodium Falciparum," Blood. 74(2): 855-861 (1989).
Needham, P.L., "Separation of Human Blood Using 'Mono-Poly Resolving Medium'" Journal of Immunological Methods, 99: 283-284 (1986).
Non-Final Office Action dated Apr. 22, 2015 for U.S. Appl. No. 13/582,263, "Microfluidics Sorter for Cell Detection and Isolation".
Non-Final Office Action dated Aug. 5, 2016 for U.S. Appl. No. 14/429,280, "Micro-Fluidic Device and Uses Thereof".
Non-Final Office Action dated Mar. 26, 2014 for U.S. Appl. No. 13/582,263, "Microfluidics Sorter for Cell Detection and Isolation".
Notice of Allowance and Fees Due for U.S. Appl. No. 13/582,263, "Microfluidics Sorter for Cell Detection and Isolation", dated May 20, 2016.
Notification Concerning Transmittal of International Preliminary Report on Patentability for International Application No. PCT/US2011/027276, entitled: "Microfluidics Sorter for Cell Detection and Isolation," dated Sep. 4, 2012.
Notification Concerning Transmittal of International Preliminary Report on Patentability for International Application No. PCT/SG2013/000412, titled: "Micro-Fluidic Device and Uses Thereof," dated Nov. 25, 2013.
Notification of Transmittal of the International Search Report and the Written Opinion of the International Searching Authority for Int'l Application No. PCT/SG2013/000412, titled: "Micro-Fluidic Device and Uses Thereof," dated Nov. 25, 2013.
Notification of Transmittal of the International Search Report and the Written Opinion of the International Searching Authority, or the Declaration for International Application No. PCT/US2011/027276, entitled: "Microfluidics Sorter for Cell Detection and Isolation,": dated May 13, 2011.
Ookawara, S., et al., "Feasibility Study on Concentration of Slurry and Classification of Contained Particles by Microchannel", Chemical Engineering Journal, 101(1-3): 171-178 (2004).
Ookawara, S., et al., "Quasi-Direct Numerical Simulation of Lift Force-Induced Particle Separation in a Curved Microchannel by Use of a Macroscopic Particle Model", Chemical Engineering Science, 62(9): 2454-2465 (2007).
Panaro, N.J., et al., "Micropillar Array Chip for Integrated White Blood Cell Isolation and PCR", Biomolecular Engineering, 21(6): 157-162 (2005).

(56) References Cited

OTHER PUBLICATIONS

Paterlini-Brechot, P. and Benali, N.L.,"Circulating Tumor Cells (CTC) Detection: Clinical Impact and Future Directions," Cancer letters, 253(2): p. 180-204 (2007).
Paulitschke, M., et al., "Membrane Rigidity of Red Blood Cells Parasitized by Different Strains of Plasmodium Falciparum," Journal of Laboratory and Clinical Medicine, 122(5): 581-589 (1993).
Popel, A.S. et al., "Microcirculation and Hemorheology," Annual Review of Fluid Mechanics. 37: 43-69 (2005).
Price, A.K., et al., "Monitoring Erythrocytes in a Microchip Channel that Narrows Uniformly: Towards an Improved Microfluidic-Based Mimic of the Microcirculation," Journal of Chromatography A, 1111(2): 220-227 (2006).
Pries, A.R., et al., "Biophysical Aspects of Blood Flow in the Microvasculature," Cardiovascular Research. 32(4): 654-667 (1996).
Riethdorf, S., et al., "Detection of Circulating Tumor Cells in Peripheral Blood of Patients with Metastatic Breast Cancer: A Validation Study of the CellSearch System", Clin. Cancer Res., 13(3): 920-928 (2007).
Ring, A., et al. "Circulating Tumour Cells in Breast Cancer", The lanced Oncology, 5: 79-88 (2004).
Rosenbluth, M.J., et al., "Force Microscopy of Nonadherent Cells: A Comparison of Leukemia Cell Deformability," Biophysical Journal, 90(8): 2994-3003 (2006).
Russom, A., et al., "Differential Inertial Focusing of Particles in Curved Low-Aspect-Ratio Microchannels," New Journal of Physics, 11: 075025 (9 pp) (2009).
Safeukui, I., et al., "Retention of Plasmodium Falciparum Ring-Infected Erythrocytes in the Slow, Open Microcirculation of the Human Spleen," Blood. 112(6):2520-2528 (2008).
Schaff, U.Y., et al., "Vascular Mimetics Based on Microfluidics for Imaging the Leukocyte-Endothelial Inflammatory Response," Lab-on-a-Chip, 7:448-456 (2007).
Schmid-Schonbein, G.W., et al., "Morphometry of Human Leukocytes," Blood, 56(5): 866-875 (1980).
Segre, G. et al., "Behaviour of Macroscopic Rigid Spheres in Poiseuille Flow," J. Fluid Mech, 14: 115-136 (1962).
Segre, G. et al., "Radial Particle Displacements in Poiseuille Flow of Suspensions," Nature, 189: 209-210 (1961).
Selzer, N ., et al., "Water induces autocrine stimulation of tumor cell killing through ATP release and P2 receptor binding", Cell Death and Differentiation, 11: p. S 172-S 180 (2004).
Seo, J., et al., Membrane-Free microfiltration by asymmetric inertial migration, Applied Physics Letters, 91(3): p. 033901-3 (2007).
Sethu, P., et al., "Microfluidic Isolation of Leukocytes from Whole Blood for Phenotype and Gene Expression Analysis", Analytical Chemistry, 78(15): 5453-5461 (2006).
Sethu, P., et al., "Microfluidic Diffusive Filter for Apheresis (Leukapheresis)," Lab on a Chip, 6(1): p. 83-89 (2006).
Shelby, J.P., et al., "A Microfluidic Model for Single-Cell Capillary Obstruction by Plasmodium Falciparum-Infected Erythrocytes," Proceedings of the National Academy of Sciences of the United States of America, 100(25): 14618-14622 (2003).
Shevkoplyas, S.S., et al., "Biomimetic Autoseparation of Leukocytes from Whole Blood in a Microfluidic Device," Analytical Chemistry. 77(3): 933-937 (2005).
Shevkoplyas, S.S., et al., "Direct Measurement of the Impact of Impaired Erythrocyte Deformability on Microvascular Network Perfusion in a Microfluidic Device," Lab on a Chip. 6(7): 914-920 (2006).
Stevens, D.Y., et al., "Enabling a Microfluidic Immunoassay for the Developing World by Integration of On-Card Dry Reagent Storage," Lab on a Chip. 8(12): 2038-2045 (2008).
Suresh, S., et al., "Connections Between Single-Cell Biomechanics and Human Disease States: Gastrointestinal Cancer and Malaria," Acta Biomaterialia, 1(1): 15-30 (2005).
Sutton, N., et al., "A Novel Instrument for Studying the Flow Behaviour of Erythrocytes Through Microchannels Simulating Human Blood Capillaries," Microvascular Research, 53(3): 272-281 (1997).
Tan, S.J., et al., "Microdevice for the Isolation and Enumeration of Cancer Cells from Blood," Biomedical Microdevices, 11(4): 883-892 (2009).
Thevoz, P., et al., "Acoustophoretic Synchronization of Mammalian Cells in Microchannels," Analytical chemistry 82: 3094-3098 (2010).
Toner, M. and Irimia, D., "Blood-On-A-Chip," Annual Review of Biomedical Engineering, 7:77-103 (2005).
Tong, X, et al., "Separation and Characterization of Red Blood Cells with Different Membrane Deformability Using Steric Field-flow Fractionation," Journal of Chromatography B: Biomedical Sciences and Applications. 674(1): 39-47 (1995).
Vona, G., et al., "Enrichment, Immunomorphological, and Genetic Characterization of Fetal Cells Circulating in Maternal Blood," American Journal of Pathology, 160(1): 51-58 (2002).
Wersto, R.P., et al., "Doublet Discrimination in DNA Cell-Cycle Analysis," Cytometry Part B: Clinical Cytometry, 46(5): 296-306 (2001).
Whitfield, M.L., et al., "Identification of Genes Periodically Expressed in the Human Cell Cycle and Their Expression in Tumors," Molecular Biology of the Cell, 2002. 13(6): 1977-2000 (2002).
Xia, Y. et al., "Soft Lithography," Annual Review of Materials Science, 28(1): 153-184 (1998).
Yamada, M. et al., "Hydrodynamic filtration for on-chip particle concentration and classification utilizing microfluidics", The Royal Society of Chemistry, Lab on a Chip, 5(11): 1233-1239 (2005).
Yamada, M., et al., "Pinched Flow Fractionation: Continuous Size Separation of Particles Utilizing a Laminar Flow Profile in a Pinched Microchannel," Anal. Chem., 76(18): 5465-5471 (2004).
Yeh, C., et al., "Transient Lateral Transport of Platelet-Sized Particles in Flowing Blood Suspensions," Biophysical Journal, 66(5): 1706-1716 (1994).
Zabaglo, L., et al., "Cell Filtration—Laser Scanning Cytometry for the Characterisation of Circulating Breast Cancer Cells," Cytometry Part A, 55(2): 102-108 (2003).
Zeng, L., et al., "Wall-Induced Forces on a Rigid Sphere at Finite Reynolds Number," Journal of Fluid Mechanics, 536: 1-25 (2005).
Zhao, R., et al., "Micro-Flow Visualization of Red Blood Cell-Enhanced Platelet Concentration at Sudden Expansion," Annals of Biomedical Engineering. 36(7): 1130-1141 (2008).
Zheng, S., et al., "Membrane Microfilter Device for Selective Capture, Electrolysis and Genomic Analysis of Human Circulating Tumor Cells," Journal of Chromatography A, 1162(2): 154-161 (2007).
Zheng, S., et al., "Streamline-Based Microfluidic Device for Erythrocytes and Leukocytes Separation," Journal of Microelectromechanical Systems, 17(4): 1029-1038 (2008).
Zimmerman, P.A., et al., "Diagnosis of Malaria by Magnetic Deposition Microscopy," American Journal of Tropical Medicine and Hygiene. 74(4): 568-572 (2006).
Al-Nbaheen, M., et al. Human stromal (mesenchymal) stem cells from bone marrow, adipose tissue and skin exhibit differences in molecular phenotype and differentiation potential. *Stem Cell Rev* 9, 32-43 (2013).
Arai, F., et al. Tie2/angiopoietin-1 signaling regulates hematopoietic stem cell quiescence in the bone marrow niche. *Cell* 118, 149-161 (2004).
Awaya, N., Rupert, K., Bryant, E. & Torok-Storb, B. Failure of adult marrow-derived stem cells to generate marrow stroma after successful hematopoietic stem cell transplantation. *Experimental Hematology* 30, 937-942 (2002).
Ball, L.M., et al. Cotransplantation of ex vivo expanded mesenchymal stem cells accelerates lymphocyte recovery and may reduce the risk of graft failure in haploidentical hematopoietic stem-cell transplantation. *Blood* 110, 2764-2767 (2007).

(56) References Cited

OTHER PUBLICATIONS

Ball, L.M., et al. Graft dysfunction and delayed immune reconstitution following haploidentical peripheral blood hematopoietic stem cell transplantation. *Bone Marrow Transplantation* 35 Suppl 1, S35-38 (2005).
Battiwalla, M. & Hematti, P. Mesenchymal stem cells in hematopoietic stem cell transplantation. *Cytotherapy* 11, 503-515 (2009).
Bianco, P., Riminucci, M., Gronthos, S. & Robey, P.G. Bone marrow stromal stem cells: Nature, biology, and potential applications. *Stem Cells* 19, 180-192 (2001).
Boxall, S.A. & Jones, E. Markers for characterization of bone marrow multipotential stromal cells. *Stem Cells Int* 2012, 975871 (2012).
Calvi, L.M., et al. Osteoblastic cells regulate the haematopoietic stem cell niche. *Nature* 425, 841-846 (2003).
Cao, X., et al. Irradiation induces bone injury by damaging bone marrow microenvironment for stem cells. *Proceedings of the National Academy of Sciences of the United States of America* 108, 1609-1614 (2011).
Chen, F.M., Zhang, M. & Wu, Z.F. Toward delivery of multiple growth factors in tissue engineering. *Biomaterials* 31, 6279-6308 (2010).
Chen, L.W., Tredget, E.E., Liu, C.X. & Wu, Y.J. Analysis of Allogenicity of Mesenchymal Stem Cells in Engraftment and Wound Healing in Mice. *Plos One* 4(2009).
Christopeit, M., et al. Marked improvement of severe progressive systemic sclerosis after transplantation of mesenchymal stem cells from an allogeneic haploidentical-related donor mediated by ligation of CD137L. *Leukemia* 22, 1062-1064 (2008).
Clines, G.A., "Prospects for osteoprogenitor stem cells in fracture repair and osteoporosis", *Current Opinion in Organ Transplantation*, (2010), 15:(1): 73-78.
Ding, L. & Morrison, S.J. Haematopoietic stem cells and early lymphoid progenitors occupy distinct bone marrow niches. *Nature* 495, 231-235 (2013).
Dominici, et al., *Cytotherapy* 8(4): 315-317 (2006).
Ehninger, A. & Trumpp, A. The bone marrow stem cell niche grows up: mesenchymal stem cells and macrophages move in. *J Exp Med* 208, 421-428 (2011).
El-Badri, N.S., Wang, B.Y., Cherry & Good, R.A. Osteoblasts promote engraftment of allogeneic hematopoietic stem cells. *Experimental Hematology* 26, 110-116 (1998).
Fouillard, L., et al. Infusion of allogeneic-related HLA mismatched mesenchymal stem cells for the treatment of incomplete engraftment following autologous haematopoietic stem cell transplantation. *Leukemia* 21, 568-570 (2007).
Granero-Molto, F., et al. Regenerative effects of transplanted mesenchymal stem cells in fracture healing. *Stem Cells* 27, 1887-1898 (2009).
Greenbaum, A., et al. CXCL12 in early mesenchymal progenitors is required for haematopoietic stem-cell maintenance. *Nature* 495, 227-230 (2013).
Guan, et al., "Spiral microchannel with rectangular and trapezoidal cross-sections for size based particle separation", *Scientific Reports*, 3:1475 (2013), 9 pages.
Heo, S.C., et al. Tumor necrosis factor-alpha-activated human adipose tissue-derived mesenchymal stem cells accelerate cutaneous wound healing through paracrine mechanisms. *J Invest Dermatol* 131, 1559-1567 (2011).
Hooper, A.T., et al. Engraftment and reconstitution of hematopoiesis is dependent on VEGFR2-mediated regeneration of sinusoidal endothelial cells. *Cell Stem Cell* 4, 263-274 (2009).
Horwitz, E.M. MSC: a coming of age in regenerative medicine. *Cytotherapy* 8, 194-195 (2006).
Horwitz, E.M., Maziarz, R.T. & Kebriaei, P. MSCs in hematopoietic cell transplantation. *Biol Blood Marrow Transplant* 17, S21-29 (2011).
Hutson, E.L., et al., "Rapid Isolation, expansion, and differentiation of osteoprogenitors from full-term umbilical cord blood", *Tissue Engineering*, 11(9-10): 1407-1420 (2005).
Isolation of monomuclear cells from human cord blood by density gradient centrifugation, MACS Miltenyi Biotec (2008) 1 pg.
Itoh, S., "Bone marrow-derived HipOP cell population is markedly enriched in osteoprogenitors", *International Journal of Molecular Sciences*, 13(8): 10229-10235 (2012).
Jung, S., Panchalingam, K.M., Wuerth, R.D., Rosenberg, L. & Behie, L.A. Large-scale production of human mesenchymal stem cells for clinical applications. *Biotechnology and Applied Biochemistry* 59, 106-120 (2012).
Keating, A. Mesenchymal stromal cells: new directions. *Cell Stem Cell* 10, 709-716 (2012).
Kolf, C.M., Cho, E. & Tuan, R.S. Mesenchymal stromal cells—Biology of adult mesenchymal stem cells: regulation of niche, self-renewal and differentiation. *Arthritis Research & Therapy* 9(2007).
Kong, Y., et al. Association of an impaired bone marrow microenvironment with secondary poor graft function after allogeneic hematopoietic stem cell transplantation. *Biol Blood Marrow Transplant* 19, 1465-1473 (2013).
Kopp, H.G., Hooper, A.T., Avecilla, S.T. & Rafii, S. Functional heterogeneity of the bone marrow vascular niche. *Ann N Y Acad Sci* 1176, 47-54 (2009).
Lange, C., et al. Radiation rescue: mesenchymal stromal cells protect from lethal irradiation. *Plos One* 6, e14486 (2011).
Le Blanc, K., et al. Transplantation of mesenchymal stem cells to enhance engraftment of hematopoietic stem cells. *Leukemia* 21, 1733-1738 (2007).
Lee, R.H., et al. Characterization and expression analysis of mesenchymal stem cells from human bone marrow and adipose tissue. *Cell Physiol Biochem* 14, 311-324 (2004).
Lee, W. C., et al., "Multivariate biophysical markers predictive of mesenchymal stromal cell multipotency", *PNAS*, E4409-E4418, (2014).
Li, Z., et al. Epigenetic dysregulation in mesenchymal stem cell aging and spontaneous differentiation. *Plos One* 6, e20526 (2011).
Loffredo, F.S., Steinhauser, M.L., Gannon, J. & Lee, R.T. Bone marrow-derived cell therapy stimulates endogenous cardiomyocyte progenitors and promotes cardiac repair. *Cell Stem Cell* 8, 389-398 (2011).
Morad, V., et al. The myelopoietic supportive capacity of mesenchymal stromal cells is uncoupled from multipotency and is influenced by lineage determination and interference with glycosylation. *Stem Cells* 26, 2275-2286 (2008).
Naveiras, O., et al. Bone-marrow adipocytes as negative regulators of the haematopoietic microenvironment. *Nature* 460, 259-263 (2009).
Neiva, K., Sun, Y.X. & Taichman, R.S. The role of osteoblasts in regulating hematopoietic stem cell activity and tumor metastasis. *Braz J Med Biol Res* 38, 1449-1454 (2005).
Nivedita and Papautsky, *Biomicrofluidics*, 7:054101-1-14 (2013).
Noort, W.A., et al. Mesenchymal stem cells promote engraftment of human umbilical cord blood-derived CD34(+) cells in NOD/SCID mice. *Experimental Hematology* 30, 870-878 (2002).
Notification Concerning Transmittal of International Preliminary Report on Patentability, with International Preliminary Report on Patentability, for International Application No. PCT/US2015/000029, entitled "Biophysically Sorted Osteoprogenitors From Culture Expanded Bone Marrow Derived Mesenchymal Stromal Cells (MSCs)", dated Sep. 1, 2016.
Notification of Transmittal of the International Search Report and the Written Opinion of the International Searching Authority, with International Search Report and Written Opinion, with the International Search Report and the Written Opinion, for International Application No. PCT/US2015/000029, entitled "Biophysically Sorted Osteoprogenitors From Culture Expanded Bone Marrow Derived Mesenchymal Stromal Cells (MSCs)", dated Jun. 4, 2015.
Olbrich, M., et al., "Isolation of osteoprogenitors from human jaw periosteal cells: a comparison of two magnetic separation methods", *PLOS One*, 7(10): e47176 (2012).

(56) References Cited

OTHER PUBLICATIONS

Owen, T.A., et al., "Isolationand culture of rosent osteoprogenitor cells", *Methods in Molecular Biology*, 455, 3-18 (2008).
Park, D., et al. Endogenous bone marrow MSCs are dynamic, fate-restricted participants in bone maintenance and regeneration. *Cell Stem Cell* 10, 259-272 (2012).
Park, J.S., Yang, H.N., Woo, D.G., Jeon, S.Y. & Park, K.H. The promotion of chondrogenesis, osteogenesis, and adipogenesis of human mesenchymal stem cells by multiple growth factors incorporated into nanosphere-coated microspheres. *Biomaterials* 32, 28-38 (2011).
Phinney, D.G. & Prockop, D.J. Concise review: Mesenchymal stem/multipotent stromal cells: The state of transdifferentiation and modes of tissue repair—Current views. *Stem Cells* 25, 2896-2902 (2007).
Poncin, G., et al. Characterization of spontaneous bone marrow recovery after sublethal total body irradiation: importance of the osteoblastic/adipocytic balance. *Plos One* 7, e30818 (2012).
Poon, Z., et al., "Bone Marrow Regeneration Promoted by Biophysical Sorted Osteoprogenitors from Mesenchyman Stromal Cells", *Stem Cells Translational Medicine*, 4(1): 56-65 (2015).
Raaijmakers, M.H., et al. Bone progenitor dysfunction induces myelodysplasia and secondary leukaemia. *Nature* 464, 852-857 (2010).
Ranganath, S.H., Levy, O., Inamdar, M.S. & Karp, J.M. Harnessing the mesenchymal stem cell secretome for the treatment of cardiovascular disease. *Cell Stem Cell* 10, 244-258 (2012).
Robey, P.G. & Termine, J.D. Human bone cells in vitro. *Calcif Tissue Int* 37, 453-460 (1985).
Sacchetti, B., et al., "Self-renewing osteoprogenitors in bone marrow sinusoids can organize a hematopoietic microenvironment", *Cell*, 131(2): 324-336 (2007).
Schallmoser, K., et al. Rapid large-scale expansion of functional mesenchymal stem cells from unmanipulated bone marrow without animal serum. *Tissue Engineering Part C—Methods* 14, 185-196 (2008).
Shirota, T. & Tavassoli, M. Cyclophosphamide-induced alterations of bone marrow endothelium: implications in homing of marrow cells after transplantation. *Experimental Hematology* 19, 369-373 (1991).
Taichman, R.S., Reilly, M.J. & Emerson, S.G. Human osteoblasts support human hematopoietic progenitor cells in vitro bone marrow cultures. *Blood* 87, 518-524 (1996).
Wang, X., et al., "Progenitors systemically transplanted into neonatal mice localize to areas of active bone formation in vivo: implications of cell therapy for skeletal diseases", *Stem Cells*, 24(8): 1869-1878 (2006).
Whitfield, M.J., et al., "Onset of heterogeneity in culture-expanded bone marrow stromal cells", *Stem Cell Research*, 11: 1365-1377 (2013).
Yang, X., Balakrishnan, I., Torok-Storb, B. & Pillai, M.M. Marrow Stromal Cell Infusion Rescues Hematopoiesis in Lethally Irradiated Mice despite Rapid Clearance after Infusion. *Adv Hematol* 2012, 142530 (2012).

Zeng, L., Yan, Z., Ding, S., Xu, K. & Wang, L. Endothelial injury, an intriguing effect of methotrexate and cyclophosphamide during hematopoietic stem cell transplantation in mice. *Transplant Proc* 40, 2670-2673 (2008).
Arpornmaeklong et al.; "Phenotypic Characterization, Osteoblastic Differentiation, and Bone Regeneration Capacity of Human Embryonic Stem Cell-Derived Mesenchymal Stem Cells;" Stem Cells and Development, vol. 18, No. 7, (2009); pp. 955-968.
Docheva et al.; "Researching into the cellular shape, volume and elasticity of mesenchymal stem cells, osteoblasts and osteosarcoma cells by atomic force microscopy;" J. Cell. Mol. Med. vol. 12, No. 2, (2008), pp. 537-552.
Lee et al.; "High-throughput cell cycle synchronization using inertial forces in spiral microchannels;" Lab Chip (2011); 11:1359-1367.
Shim et al.; "Alkaline Phosphatase Activity as a Predictive Marker of Osteogenesis in Human Bone Marrow-Derived Mesenchymal Stem Cells But Not Umbilical Cord Blood-Derived Mesenchymal Stem Cells;" $53^{rd}$ Annual Meeting of the Orthopaedic Research Society (Feb. 1, 2007); Poster No: 0465; 1 page.
Subramaniam et al.; "Bone Morphogenetic Proteins: Periodontal Regeneration;" N. Am. J. of Med. Sci., vol. 5, No. 3, Mar. 2013, pp. 161-168.
International Preliminary Report on Patentability and the Written Opinion of the International Searching Authority for International Application No. PCT/US2015/050604, entitled: "Microfluidic System and Method for Perfusion Bioreactor Cell Retention" dated Mar. 21, 2017.
International Preliminary Report on Patentability and the Written Opinion of the International Searching Authority for International Application No. PCT/US2015/050628, entitled: "System and Method for Inertial Focusing Microfiltration for Intra-Operative Blood Salvage Autotransfusion" dated Mar. 21, 2017.
Notice of Allowance dated Jun. 26, 2017 for U.S. Appl. No. 14/429,280, "Micro-Fluidic Device and Uses Thereof".
Notification of Transmittal of the International Search Report and the Written Opinion of the International Searching Authority, or the Declaration for International Application No. PCT/US2015/050604, entitled: "Microfluidic System and Method for Perfusion Bioreactor Cell Retention" dated Dec. 7, 2015.
Notification of Transmittal of the International Search Report and the Written Opinion of the International Searching Authority, or the Declaration for International Application No. PCT/US2015/050628, entitled: "System and Method for Inertial Focusing Microfiltration for Intra-Operative Blood Salvage Autotransfusion" dated Dec. 21, 2015.
Office Action dated May 5, 2017 for U.S. Appl. No. 14/429,280, "Micro-Fluidic Device and Uses Thereof".
Supplementary European Search Report for EP Application No. 15752783.9, "Biophysically Sorted Osteoprogenitors From Culture Expanded Bone Marrow Derived Mesenchymal Stromal Cells (MSCs)", dated Jun. 30, 2017.

* cited by examiner

H

I

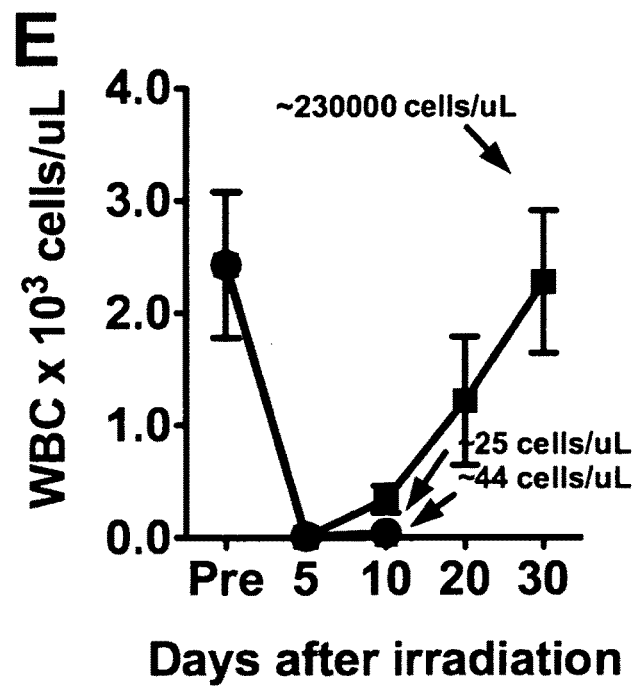
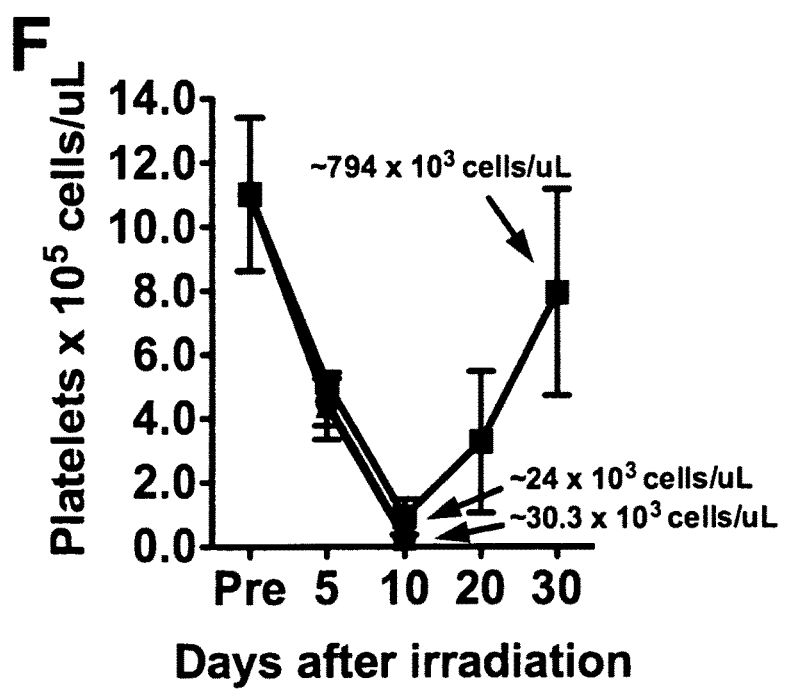
FIGS. 2E - F

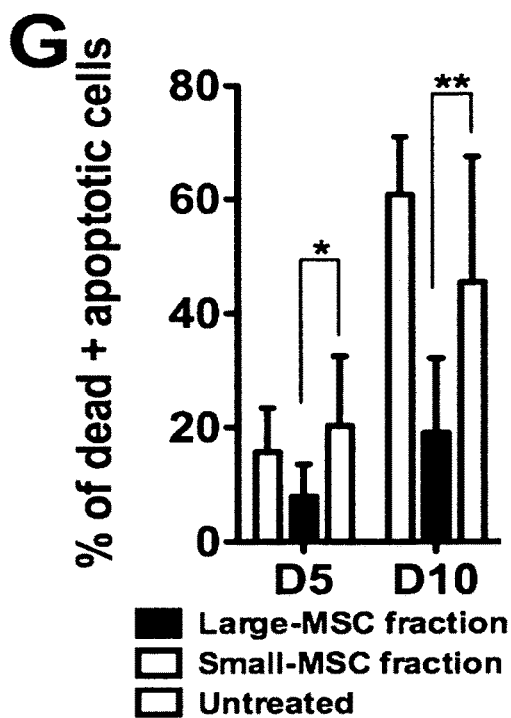
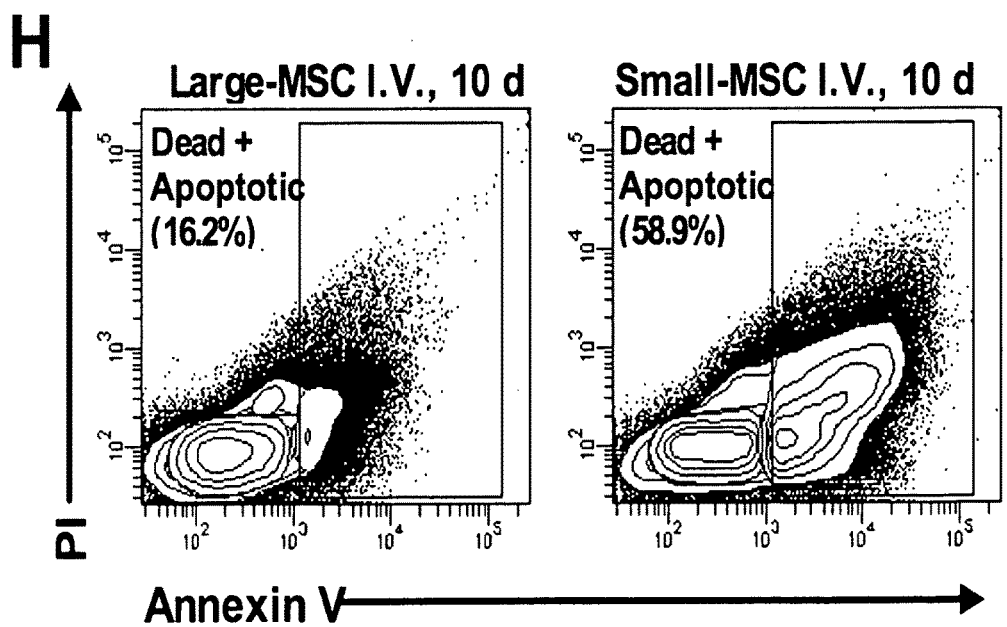
FIGS. 2G - H

A

Day 0:
Sublethal irraidation

Treatment 1:
MSC infusion on day 1
HSC infusion on day 7
Analysis on day 8

Treatment 2:
MSC + HSC co-infusion on day 1
Analysis on day 8

| Gene | Primer (5' to 3') | Accession Number | SEQ ID NO: |
|---|---|---|---|
| GAPDH forward | CAAGGCTGTGGGCAAGGT | NM_002046.4 | SEQ ID NO:1 |
| GAPDH reverse | GGAAGGCCATGCCAGTGA | | SEQ ID NO:2 |
| Runx2 forward | CGAATGGCAGCACGCTATTA | NM_001024630.3 | SEQ ID NO:3 |
| Runx2 reverse | TGGCTTCCATCAGCGTCAA | | SEQ ID NO:4 |
| Osteopontin forward | CGGGACCAGACTCGTCTCA | NM_000582.2 | SEQ ID NO:5 |
| Osteopontin reverse | TTCCTTGGTCGGCGTTTG | | SEQ ID NO:6 |
| Osteocalcin forward | TCCACAGCCTTTGTGTCCAA | NM_199173.4 | SEQ ID NO:7 |
| Osteocalcin reverse | GCGCCTGGGTCTCTTCACTA | | SEQ ID NO:8 |
| Pparg forward | TCAGGGCTGCCAGTTTCG | NM_138712.3 | SEQ ID NO:9 |
| Pparg reverse | GCTTTTGGCATACTCTGTGATCTC | | SEQ ID NO:10 |
| Sox9 forward | CCGGGCCCGCGTAT | NM_000346.3 | SEQ ID NO:11 |
| Sox9 reverse | TCCTGCTCGTCGGTCATCTT | | SEQ ID NO:12 |
| IL6 forward | AGGGCTCTTCGGCAAATGTA | NM_000600.3 | SEQ ID NO:13 |
| IL6 reverse | GAAGGAATGCCCATTAACAACAA | | SEQ ID NO:14 |
| IL8 forward | CACCGGAAGGAACCATCTCA | NM_000584.3 | SEQ ID NO:15 |
| IL8 reverse | AGAGCCACGGCCAGCTT | | SEQ ID NO:16 |
| VEGF-A forward | CGAGGGCCTGGAGTGTGT | NM_001204385.1 | SEQ ID NO:17 |
| VEGF-A reverse | CGCATAATCTGCATGGTGATG | | SEQ ID NO:18 |
| Bmp2 forward | AAAGGGCATCCTCTCCACAA | NM_001200.2 | SEQ ID NO:19 |
| Bmp2 reverse | AGGCGTTTCCGCTGTTTG | | SEQ ID NO:20 |
| FGF1 forward | GTTTAATCTGCCTCCAGGGAA TT | NM_001257212.1 | SEQ ID NO:21 |
| FGF1 reverse | AGTGGCCCCCGTTGCTA | | SEQ ID NO:22 |
| IGFBP2 forward | TGACAAGCATGGCCTGTACAA | NM_000597.2 | SEQ ID NO:23 |
| IGFBP2 reverse | CACGCTGCCCGTTCAGA | | SEQ ID NO:24 |
| ANGPTL2 forward | CCTCCCCCCACATTTTCAT | NM_012098.2 | SEQ ID NO:25 |
| ANGPTL2 reverse | GGATAAGTGGGTGATGGATGGT | | SEQ ID NO:26 |
| ANGPTL3 forward | CCAATGCAATCCCGGAAA | NM_014495.3 | SEQ ID NO:27 |
| ANGPTL3 reverse | TGAAGTGTCCTTTTGCTTTGTGA | | SEQ ID NO:28 |
| ANGPTL5 forward | TGGTCAATGGTCAGTCTGTGAAG | NM_178127.4 | SEQ ID NO:29 |
| ANGPTL5 reverse | AACCACCAGCCGGTCTTGT | | SEQ ID NO:30 |
| Nestin forward | AGCCCTGACCACTCCAGTTTAG | NM_006617.1 | SEQ ID NO:31 |
| Nestin reverse | CCCTCTATGGCTGTTTCTTTCTCT | | SEQ ID NO:32 |
| Ang1 forward | TCCAGGTTATCCCAGAGATTTAATG | NM_004673.3 | SEQ ID NO:33 |
| Ang1 reverse | GGGCTTTTGGTGGGAGAAGT | | SEQ ID NO:34 |
| EGF forward | TGTAAAAACACCCCTGGATCCTA | NM_001178131.1 | SEQ ID NO:35 |
| EGF reverse | CCCATCAGGAAGCAGAACAAA | | SEQ ID NO:36 |
| FGF2 forward | AATCAAAAGTTCGGCATGTAGCT | NM_002006.4 | SEQ ID NO:37 |
| FGF2 reverse | CTGAGCAGGGCAGATTTGCT | | SEQ ID NO:38 |
| MCP1 forward | CAAGCAGAAGTGGGTTCAGGAT | NM_002982.3 | SEQ ID NO:39 |
| MCP1 reverse | TCTTCGGAGTTTGGGTTTGC | | SEQ ID NO:40 |
| PDGFB forward | ATCGCCATCTTCTTCCCTTAACT | NM_033016.2 | SEQ ID NO:41 |
| PDGFB reverse | AGAGCGACCCCATCAGTCTCT | | SEQ ID NO:42 |

FIG. 13

| Passage 1 | Passage 2 | Passage 3 | Passage 4 | Passage 5 | Passage 6 |
|---|---|---|---|---|---|
| 1x Cryo-preserved vial ↓ 1x T175 flask | → 1x T175 flasks + 7x Cryo-preserved vials | → 2x T175 flasks + 2x Cryo-preserved vials | → 2x Triple flasks | → 8x Triple flasks | → Microfluidic sorting of MSC ↓ 1x Cryo-preserved bag ↓ Thaw and wash |

FIG. 17

| Passage 1 | Passage 2 | Passage 3 | Passage 4 | Passage 5 | Passage 6 |
|---|---|---|---|---|---|
| 1x Cryo-preserved vial ↓ 1x T175 flask | → 2x T175 flasks + 6x Cryo-preserved vials | → 5x T175 flasks + 3x Cryo-preserved vials | → 5x Triple flasks | → 20x Triple flasks | → Microfluidic sorting of MSC ↓ 1x Cryo-preserved bag ↓ Thaw and wash |

FIG. 18

BIOPHYSICALLY SORTED OSTEOPROGENITORS FROM CULTURE EXPANDED BONE MARROW DERIVED MESENCHYMAL STROMAL CELLS (MSCS)

RELATED APPLICATION

This application is the U.S. National Stage of International Application No. PCT/US2015/000029, filed Feb. 18, 2015, which designates the U.S., published in English, and claims the benefit of U.S. Provisional Application No. 61/941,081, filed Feb. 18, 2014. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: 44711020002SequenceListing.txt; created Aug. 16, 2016, 8 KB in size.

BACKGROUND OF THE INVENTION

Studies continue to show that most adult organ systems have a resident pool of dormant, tissue specific stem cells that can activate reparative mechanisms during periods of traumatic injury, but disease, age and extensive tissue damage are factors that cause the quantity and potency of these stem cell populations to be insufficient for wound healing and tissue recovery. These repair deficiencies can be supplemented through strategies to extract, expand and re-implant additional numbers of adult stem cells, such that they aid in regeneration to supplant damaged cells as well as rejuvenation to stimulate endogenous repair mechanisms.

Bone marrow derived mesenchymal stem/stromal cells (MSCs) are leading candidates for these applications due to their widespread availability and applicability for many indications. Since their discovery, MSC-based medical technology has undergone constant evolution to improve their potencies; however, the current clinical experience still indicates that the capacity to produce large quantities of cells ex vivo with uniform and relevant therapeutic properties is a critical unmet need for their advancement. In recent years, new mechanisms for MSC mediated regeneration have been identified, further necessitating a re-evaluation of the approaches taken to prepare culture expanded MSCs for therapy.

Accordingly, a need exists for populations of MSCs with more uniform properties and enhanced regenerative potential, as well as methods of making and using them.

SUMMARY OF THE INVENTION

The invention provides, inter alia, MSCs with more uniform properties and enhanced regenerative potential, as well as methods of making and using them. The invention is based, at least in part, on the discovery that large-MSCs have enhanced regenerative activity.

In one aspect, the invention provides methods of culturing an MSC-containing population cells to produce an MSC population with enhanced regenerative potential. The method can include culturing an MSC-containing population of cells in a culture medium, preferably to a confluence of 80% to 90%. Optionally, the MSC-containing population of cells can be trypsinized one or more times. The culturing and optional trypsinizing can be repeated so that the MSC-containing population of cells doubles at least four times, as measured from initial extraction of the MSC-containing population from a source, to thereby produce an MSC population with enhanced regenerative potential. Optionally, a portion of the MSC-containing population of cells can be cryopreserved in a cryopreservation medium after one or more population doublings.

In another aspect, the invention provides methods of producing an MSC population with enhanced regenerative potential. These methods entail biophysically sorting (e.g., using an MSC-dimensioned microfluidic device) an MSC-containing population of cells and collecting a large-MSC population of cells from the MSC-containing population, where the biophysical sorting has a throughput of at least about $10^3$ cells/minute. Preferably, the biophysically sorted MSC-containing population has been cultured according to the cell culture methods described herein, such as those summarized in the preceding paragraph.

In related aspects, the invention provides isolated populations of large-MSCs (e.g., produced by the methods provided by the invention or any other means known to the skilled artisan). In certain embodiments, these isolated populations of large-MSCs can be cryopreserved or otherwise made into cell banks. In related aspects, the invention also provides conditioned medium from such populations.

In another aspect, the invention comprises systems adapted for isolating large-MSCs. In certain embodiments, these systems include one or more devices adapted for biophysical sorting of large-MSCs (and where there is a plurality of devices—such as 2, 3, 4, 5, 6, 7, 8, 9, 10, or more—the devices may all be the same, or include a collection of different devices), where the device is in fluid communication with a reservoir with an MSC-containing population. These systems, in some embodiments, can include an injector that applies the fluid to the device under pressure.

In a further aspect, the invention provides methods of mediating tissue repair in a mammalian subject by applying a large-MSC population of cells, or a conditioned medium from a culture of large-MSCs, into the subject. Related aspects include a large-MSC population of cells, or a conditioned medium from a culture of large-MSCs, for use as a medicament; a large-MSC population of cells, or a conditioned medium from a culture of large-MSCs, for use in the treatment of tissue in need of repair; and the use of a large-MSC population of cells, or a conditioned medium from a culture of large-MSCs, for the manufacture of a medicament for treatment of tissue in need of repair.

In a further aspect, the invention provides methods of enhancing homing and engraftment of hematopoietic stem cells (HSCs) in the bone marrow of a mammalian subject by co-administering a large-MSC population of cells, or a conditioned medium from a culture of large-MSCs, and HSCs into the subject. Related aspects include a large-MSC population of cells, or a conditioned medium from a culture of large-MSCs, and HSCs for use as a medicament; a large-MSC population of cells, or a conditioned medium from a culture of large-MSCs, and HSCs for use in the treatment of tissue in need of repair; and the use of a large-MSC population of cells, or a conditioned medium from a culture of large-MSCs, and HSCs for the manufacture of a medicament for treatment of tissue in need of repair.

The methods described herein can be combined together. For example, the methods of culturing an MSC-containing population of cells can be performed to produce an MSC population with an enhanced regenerative potential (e.g., a large-MSC population). The large-MSC population can subsequently be biophysically sorted as described herein, and the biophysically sorted large-MSC population can be used in the methods of mediating tissue repair and methods of enhancing homing and engraftment of hematopoietic stem cells, as described in the preceding paragraphs. Further, a conditioned medium from the large-MSC population can also be collected for use in the methods of mediating tissue repair.

BRIEF DESCRIPTION OF THE DRAWINGS

FIG. 1A shows that during in vitro culture, early passage (PSG) MSCs are uniform in morphology and size, but a larger and flatter MSC subpopulation is generated after ~10 population doublings. The resultant MSC culture is heterogeneous in size and morphology, and also in other biophysical characteristics. Scale bar=100 µm. In FIG. 1B, a label-free microfluidic sorting approach is utilized for sorting out 1) a population of expanded MSCs that are enriched in the larger MSC osteoprogenitors (large-MSC fraction, left panel) and 2) a population of expanded MSCs that are depleted of the larger MSC osteoprogenitors (small-MSC fraction, right panel). These MSC fractions differ morphologically after plating on tissue culture plastic and the larger MSC osteoprogenitors are estimated to be enriched by >5 fold in the sorted large-MSC fraction compared to the unsorted MSCs at PSG 6. Scale bar=100 µm. In FIG. 1C, the suspended size distribution of sorted MSCs (PSG 6, n>500 cells counted from 4 donors) are: large-MSCs=21.9+/−5.3, small-MSCs=14.8+/−2.4, *P=0.0002. Data given as mean±sem. FIG. 1D shows recovery of large- and small-MSC fractions after microfluidic sorting of PSG 3, 6 and 9 MSCs for n>5 across 4 donors. No cells are present in the large-MSC fraction after sorting earlier passage MSCs, but the approximate large-MSC recovery is 40% and 60% at PSG 6 and 9, respectively. FIG. 1E shows a representative set of data for RTPCR analysis of the expression of differentiation markers for osteogenesis (Runx2, osteopontin (OPN), osteocalcin (OCN) and osterix (OSX)), adipogenesis (Pparg) and chondrogenesis (Sox9), as well as for nestin. These data are normalized to GAPDH. FIG. 1F shows that immunostaining of OPN and OCN (an early and late osteogenic marker, respectively) in sorted MSCs detects OPN in large-MSCs only but no OCN in any MSCs, suggesting that large-MSCs are osteoprogenitors. Scale bar=50 µm. In FIG. 1G, multilineage differentiation of sorted MSCs show high potentials for osteogenic and chondrogenic differentiation but no adipogenic differentiation in large-MSCs. Trilineage differentiation potential was observed in the small-MSCs. Osteogenic, chondrogenic and adipogenic formation were determined by alizarin red, alamar blue and oil-red-o assays, respectively, and are quantitatively shown in FIG. 1H. FIG. 1H shows representative spectroscopic analysis of the degree of osteogenic, chondrogenic and adipogenic formation in sorted and unsorted MSCs at PSG 6 for unsorted (grey), large- (black) and small-(white) MSCs. These data are normalized to values of the unsorted MSCs at the same passage. A higher level of osteogenic mineralization (~3.4×) but a lower level of adipogenic oil droplet formation (~5.8×) was observed in the large-vs small-MSC fraction. FIGS. 1I-1J show in vivo ectopic bone formation by sorted MSCs on PCL-TCP scaffolds after implantation in NOD/SCIDs for 4 weeks. The degree of mineralization is measured via systemic injection of a fluorescent bisphosphonate agent 16 h before the scaffolds are harvested and imaged (FIG. 1I) ex vivo. A significantly higher level of mineral bone formation, based on bisphosphonate staining, was found in scaffolds seeded with large-MSCs. (*P=0.0383; FIG. 1J, a bar graph) vs small-MSCs. All values are given in mean±sd unless otherwise stated. All MSCs were used at PSG 6 unless otherwise stated.

FIG. 2A shows survival curves of NOD/SCID mice after lethal irradiation (day 0) and the administration of the different treatments on day 1. Injection of unsorted MSCs at PSG 3, 6 and 9 resulted in mean survival times of 10.5, 12, and 17 days, respectively (n>5 mice per group). FIGS. 2D-2F show whole blood counts of NOD/SCIDs in FIG. 2B, showing full hematopoietic recovery over a 30 day period for the large-MSC treatment group. FIGS. 2G and 2H show live/dead FACS analysis of BM aspirates from treatment groups in FIG. 2B, showing significantly lower numbers of dead/apoptotic cells in the BM after large-MSC treatment. *P=0.0308 and **P=0.0231 for day 5 and day 10, respectively (n=8 femoral BM aspirates tested). FIGS. 2M and 2N show that EdU$^+$ cells in the large-MSC treatment group co-localize with murine CD31/VEGR2 vasculature and nestin$^+$ or CD146$^+$ stromal cells during recovery after lethal irradiation. Scale bars=100 µm. All values are given in mean±sd unless otherwise stated. >100,000 events are measured for FACS analysis. In FIGS. 2G and 20I: Black graphs=large-MSC fraction, white graphs=small-MSC fraction. All MSCs were used at PSG 6 unless otherwise stated.

FIG. 3A is a dorsal view of the in vivo biodistribution of systemically injected luciferase-transformed MSCs in sublethally irradiated NOD/SCIDs (3.0 Gy) over a period of 10 days. MSCs of both fractions initially accumulate in the lungs but redistribute over a 24 h period. No significant engraftment or extravasation of MSCs was found in the lungs after 24 h, with most of the remaining MSCs localized within the capillary lumen of the lung tissue ((i) vs (ii) in FIG. 3B). After their redistribution from the lungs, MSCs of both fractions also do not show any specific accumulation to the BM or any other tissue and are significantly cleared from the body after 10 days. Scale bar in FIG. 3B=100 µm. In FIG. 3C, FACS analysis of femoral BM aspirates at different time points after MSC injection shows an insignificant degree of homing of injected MSCs to the BM. On day 5, ~0.02% of the injected MSC dose (for both MSC fractions) was detected in the femoral BM and no MSCs were detected by day 20. n>4 femoral BM aspirates, 20,000 events analyzed, *P=0.9626. FIG. 3D shows survival of lethally irradiated NOD/SCIDs (n>5 mice) given regular injections (indicated by arrows) of conditioned media from the different MSC fractions. The median survival times are 29 days and 11 days for the large-MSC and small-MSC secretome therapy groups, respectively. In FIG. 3E, large- vs small-MSC fraction secretome analysis shows increased production (~3.8× on average) of soluble factors associated with angiogenesis, cell proliferation and wound healing (IL-6, IL-8, EGF, FGF1, VEGF, Ang-1, etc.). Secretome from 3 MSC donors were tested in triplicates. FIG. 3F shows relative proliferation rates of human umbilical vein endothelial cells (HUVECs) and human microvascular endothelial cells (HMVECs) after 48 h exposure to different MSC fraction secretome; cell proliferation was measured to be ~1.8× and ~2.5× higher in the large-vs small-MSC secretome for HUVEC and HMVEC, respectively. Rates were normalized to the small-MSC group (n=4 wells). FIG. 3G shows cell cycle analysis of HUVEC and HMVEC after exposure to different conditioned media for 48 h. G0=white bar; G1=light gray bar; G2/S/M=dark gray bar. *P=0.022 for G0 and **P=0.0098 for G2/S/M. FIG. 3H shows results of an in vitro 3D angiogenic sprouting assay of mCherry-transduced HUVECs in a fibrin gel (2.5 mg/mL) supplemented with different MSC secretome. Arrows indicate position of angiogenic sprouts from HUVEC loaded microcarrier beads. Scale bar=100 μm. FIG. 3I shows explanted femoral bones from lethally irradiated mice (5 days after) in a fibrin gel exposed to different MSC secretome. Red dotted line represents sectioned femoral head to expose the BM. After 10 days, capillary formation was visible from endogeneous cells in the BM in the large-MSC control group. FIG. 3J shows blood vessel density in the BM of lethally irradiated NOD/SCIDs in FIG. 3D on day 7 visualized by angiosense (a near IR in vivo imaging probe, dorsal view of mice). In comparison to the untreated group, the administration of MSC conditioned media led to increased angiogenesis in the BM, and the resultant vessel density was highest in groups given large-MSC conditioned media. All values are given in mean±sd unless otherwise stated. Black graphs=large-MSC fraction, white graphs=small-MSC fraction. All MSCs were used at PSG 6.

FIG. 4A shows experimental plans to evaluate HSC homing and engraftment to BM of MSC treated mice. FIG. 4B shows tomato-lectin staining of functional vessels in the BM of NSGs under treatment 1. Lectin was co-localized with several lumens in histological sections of BMs from large-MSC treatment groups. Scale bar=100 μm. FIG. 4C shows the number of $CD31^+$/Lectin stained vessel structures observed in histological sections taken from the femoral BM of various treated mice. Each point represents an average value obtained from 10 sections taken from the same mouse (n=6 mice in each group). Representative images are shown in FIG. 4A. FIG. 4D shows histological sections of BM24 h after human HSC injection in treatment 1, showing injected HSCs localizing around vessel-like structures expressing nestin and cxcl12. Scale bar=100 μm. FIG. 4E shows FACS quantification of the degree of HSC homing under treatment 1 on day 8. Each data point represents the number of injected HSCs detected in the combined femoral BM aspirate of one mouse (n=6 mice in each group). FIGS. 4F and 4G show endogenous recovery of $nestin^+$ stromal cells in the femoral BM after large- and small-MSC infusion. Representative FACS analysis of femoral BM aspirates after MSC treatment is shown in FIG. 4F. Percentages of $nestin^+$ cells in the BM detected by FACS on day 4 and 8 are shown in FIG. 4G. *P=0.3692 and **P=0.0103. These data show that the BM stromal elements are damaged after irradiation but recover most efficiently with large-MSC treatments. FIG. 4H shows mononuclear cell recovery after ficoll density centrifugation of femoral BM aspirates of mice under treatment 2. The highest levels of cell recovery are associated with large-MSC groups (*P=0.0059, P=0.0043, *P=0.0095). These results indicate that large-MSC therapy after myeloablative irradiation facilitates BM recovery and donor HSC engraftment (n=4-5 mice per group, data given in mean±std). In FIGS. 4I and 4J, femoral BM aspirates from FIG. 4H were cultured in triplicates in methylcellulose medium and the number of CFU-Cs (FIG. 4H, *P=0.0208, **P=0.0193) and CFU-GEMMs (FIG. 4I, *P=0.0314, **P=0.0187) were evaluated after 2 weeks. All values are given in mean±sd unless otherwise stated. Black graphs=large-MSC fraction, white graphs=small-MSC fraction. All MSCs were used at PSG 6. For all experiments in this figure, MSC dose=500K cells (I.V.) and HSC dose=100K cells (I.V.).

FIG. 5A is a dorsal view of the engraftment and repopulation kinetics visualized via bioluminescence from luciferase-transformed human HSCs over a period of 4 weeks. HSC dose was fixed among all groups tested at 100K per mice and MSCs were given as co-injections at doses of 500K per mice. The fastest kinetics were observed when large-MSCs were given as co-injections. FIG. 5B shows quantification of the bioluminescence from transformed HSCs in FIG. 5A. *P=0.0169 and 0.0339, P=0.0064 and 0.0107, *P=0.0073 and 0.0768 for large-MSC groups vs small-MSC and unsorted MSC groups, respectively, at weeks 2, 3 and 4 (n=5 mice each group). FIG. 5C shows CD45 chimerism in the peripheral blood of mice in FIG. 5A over 12 weeks. *P=0.0160 and 0.0196, P=0.0735 and 0.1364, *P=0.0704 and 0.2663 for large-MSC groups vs small-MSC and unsorted MSC groups, respectively, at weeks 4, 8 and 12 (n=5 mice each group). These results indicate that the HSC engraftment effect mediated by large-MSCs is strongest in the short-term (<4 weeks). FIGS. 5D and 5E show CD45 chimerism in the BM and peripheral blood, respectively, in myeloablated NSGs (3.0 Gy) given a dose escalation of HSCs for no MSC and large-MSC groups. All MSCs were delivered at a constant dose of 500K per mouse. For FIG. 5D, *P=0.0082, P=0.0110 and *P=0.8594. For FIG. 5E, *P=0.0045, P=0.0021 and *P=0.3128. These results indicate that large-MSC mediated effects are exerted most significantly at lower HSC doses (n=5 mice each group). FIG. 5F shows the frequency of human HSC-derived B cells, T cells and myeloid cells within the femoral BM 12 weeks after transplantation (n=5 mice). The co-injected MSCs did not affect the multilineage differentiation potential of transplanted HSCs and the engraftment enhancing effect of large-MSCs was not lineage restricted. All values are given in mean±sd unless otherwise stated. Orange graphs=large-MSC fraction, purple graphs=small-MSC fraction. All MSCs were used at PSG 6.

FIG. 13 is a primer list for RTPCR experiments used in this study.

In FIG. 15A, microfluidic sorting with a lab-made device results in two MSC fractions of different suspended diameters (FIG. 15B, large-MSCs=21.9+/−5.3, small-MSCs=14.8+/−2.4). FIG. 15C shows that large-MSCs can be continuously extracted from MSC cultures from after passage 4-5. FIG. 15D shows adherent morphology of large-vs small-MSCs. Large-MSCs are flat and irregular cells, but small-MSCs are spindle-like. In FIG. 15E, microarray analysis shows that only 8% of >40,000 analyzed genes are similarly expressed between large- vs small-MSCs despite having originated from the same early MSCs. FIG. 15F shows that large-MSCs have a secretome that is significantly different from that of small-MSCs. A higher level of regenerative factors is expressed at both the gene and protein levels. FIG. 15G shows gene expression studies evidencing that the large-MSCs fraction is an osteoprogenitor cell fraction expressing higher levels of osteogenic genes and lowered levels of genes associated with multipotency.

FIG. 17 is a workflow for MSC culture (small scale).

FIG. 18 is a workflow for MSC culture (large scale).

DETAILED DESCRIPTION OF THE INVENTION

Figures 1A, 1B, 1C:
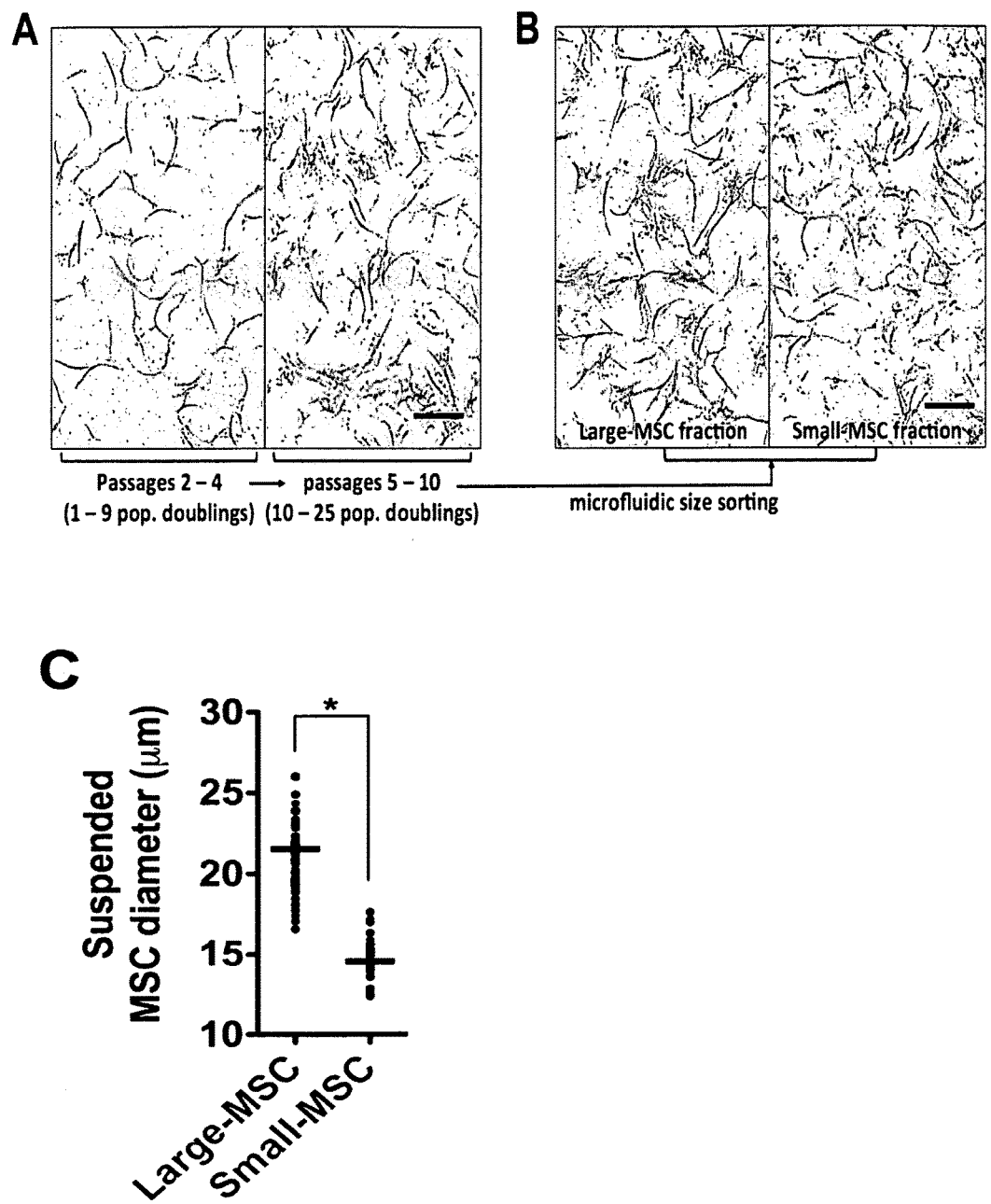
FIGS. 1A-1J show enrichment of mesenchymal stromal cell (MSC) osteoprogenitors using a label-free, microfluidic sorting approach.

The invention provides mesenchymal stem cell (MSC) populations (as well as conditioned medium from these cells) with enhanced regenerative potential, as well as methods of making and using these populations, such as therapeutic methods of mediating tissue repair or enhancing homing and engraftment of hematopoietic stem cells. These MSC populations can, in certain embodiments, be produced by biophysically sorting an MSC-containing population, e.g., at a throughput of at least $10^3$ cells/minute, and collecting a large-MSC population of cells.

"Biophysically sorting" is a process of isolating, e.g., from a heterogenous mixture, by bulk physical properties of a particle (for example, a cell), such as size, density, shape, rigidity, et cetera, which are directly detected. Biophysical sorting can be distinguished from, for example, sorting by flow cytometry using cell surface markers, which is based on detecting cells by virtue of the presence or absence of cell surface markers, such as proteins, using positive or negative selection that entails, for example, using detectably labeled antibodies for the markers—i.e., an indirect detection method. Numerous methods of biophysical sorting are known in the art, such as microfluidic devices, size exclusion filters, density columns, differential density centrifugation (e.g., using Ficoll; and related centrifugation techniques), et cetera. Of course, in some embodiments, biophysical sorting can be coupled to sorting based on cell surface markers. In particular embodiments, the biophysical sorting is with a microfluidic device, e.g., using MSC-dimensioned microfluidic device.

"MSC," "Mesenchymal Stromal Cell," and the like, refer to multipotent stromal stem cells, also known as mesenchymal stem cells, multipotent stromal cells, multipotent stem cells, and mesenchymal stromal/stem cells. Certain criteria for identifying MSCs are known in the art and are described in, for example, Dominici, et al., *Cytotherapy* 8(4): 315-317 (2006), which is incorporated by reference in its entirety. In some embodiments, MSCs are characterized by their ability to differentiate along adipocyte, chondroblast, and osteoblast lineages under appropriate conditions. MSCs may also be characterized by expression of one or more of the following cell-surface markers: CD44, CD74, CD90, CD105, CD140B, CD146 and CD166. In some more particular embodiments, the MSCs may be further characterized by also expressing one or more of: CD19, CD45, CD106, Nestin, Stro-1 or NG2. In other more particular embodiments, the MSCs may be further characterized by not expressing one or more of: CD19, CD45, CD106, Nestin, Stro-1 or NG2. Frequently, CD106, Nestin, Stro-1, and NG2 are markers for MSCs in vivo. Diminished expression of CD106, Nestin, Stro-1, and NG2 can be observed after culture expansion in vitro, typically after 1-2 cell passages (e.g., within approximately 5 population doublings). However, some cultured MSCs retain expression of Nestin, Stro-1 and NG2.

MSCs can be from any mammalian source, such as primates (e.g., humans or monkeys), cows, sheep, goats, horses, dogs, cats, rabbits, guinea pigs, rats, mice, or other bovine, ovine, equine, canine, feline, rodent or murine species. In more particular embodiments, the MSCs are from a primate, such as a human. In more particular embodiments, the human is an adult human. Any suitable tissue source can provide MSCs used in the invention, such as bone marrow, adipose tissue (fat), dental pulp, Wharton's jelly, perivascular space, umbilical cord, and placenta. In particular embodiments, the MSCs are derived from bone marrow. In certain embodiments, the MSCs, such as a mixed MSC population, are isolated by ficoll centrifugation from a tissue source and selected for adherence to plastic (such as tissue culture plastic). MSCs can, optionally, be culture expanded (e.g., on 2D or 3D (e.g., microcarrier) supports) after their isolation and before fractionation to small-MSC and large-MSC populations. The cells are preferably allowed to expand in culture for a sufficient time to allow large-MSCs to appear, which can vary from donor to donor and depending on the source of the cells. For example, large-MSCs typically appear within about 3-4 population doublings from bone marrow.

MSCs can be fractioned to small-MSC and large-MSC populations by any modality suitable to isolate these populations from a MSC-containing population, such as a mixed MSC population. Exemplary modalities for biophysical separation of large-MSCs include microfluidic devices, size exclusion filters, and density columns. In some embodiments, the modality is not a microfluidic device. In other embodiments, the modality is a microfluidic device. In more particular embodiments, devices and methods described in WO 2014/046621, Guan, et al., *Scientific Reports* 3:1475 (2013, 9 pages), US 2013/0130226 and Nivedita and Papautsky, *Biomicrofluidics* 7:054101-1-14 (2013), which are incorporated by reference in their entirety, can be adapted (e.g., by sizing the channel length, internal height/width aspect ratio, flow speed, pressure, media viscosity, channel shape (e.g., a rectangular or trapezoidal cross section)) for separating small-MSCs and large-MSCs in the form of an "MSC-dimensioned microfluidic device," in which a mixed MSC population can be applied to an inlet of the device and small-MSCs and large-MSCs can be separated at one or more outlets of the device by virtue of their different sizes, shapes, and stiffnesses when moving in fluid flow in the microfluidic device between the inlet and outlet of the device. In particular embodiments, the microfluidic device is a spiral microchannel with a trapezoidal cross-section (i.e., perpendicular to the direction of the fluid flow), with a channel width of about 600 μm (e.g., about: 500-700 μm, 550-650 μm, or 575-625 μm), an inner channel depth of about 80 μm (e.g., about: 70-90 μm, 75-85 μm) and an outer channel depth of about 130 μm (e.g., about: 110-150 μm, 120-140 μm, or 125-135 μm). The injection rate can be optimized for a given MSC-containing population and the particular device or modality used. In certain embodiments, the injection rate into the inlet of an MSC-dimensioned microfluidic device can be varied within about: 2.0-4.5 ml/minute (e.g., about: 2.0-2.5 ml/min, 2.5-3.5 ml/min, or 3.5-4.5 ml/min). In particular embodiments, the injection rate is >2.5 ml/min. In certain embodiments, the injection rate is about 2.5 to 4.0 ml/minute, preferably about 3.5 ml/minute. In general, the flow rates described herein are based on a 20 mL syringe (19.13 mm diameter) attached to a syringe pump with tubings that are 0.51 mm in internal diameter.

An "MSC-containing population" is a collection of cells that includes MSCs as well as other cells. The MSCs in an MSC-containing population can be a mixed MSC population or a fraction of small-MSCs or large-MSCs.

A "mixed MSC population" refers to a collection of MSCs that include both "large-MSCs" and "small-MSCs." The relative proportions of large-MSCs and small-MSCs in a mixed MSC population can vary.

"Large-MSCs" and the like are MSCs with a diameter of about 18-22 μm (e.g., 21.9+/−5.3 μm) and one or more of: a stiffer membrane, a low fluctuating nucleus, decreased adipogenic potential, and enhanced regenerative potential, relative to small-MSCs or a mixed MSC population. "Regenerative potential" of a MSC population encompasses one or more (i.e., 1, 2, 3, or all 4) of osteoprogenic activity (the ability to differentiate into bone producing cells quickly and robustly), homing and engraftment of hematopoietic stem cells (HSCs) during administration (either concurrently or sequentially) with MSCs, secretion of one or more of IL-6, IL-8, VEGF, BMP2, EGF, FGF1 and Ang-1 (e.g., 1, 2, 3, 4, 5, 6, or all 7 factors), and increased genetic/transcriptome level expression of osteogenic markers such as osteopontin, ALP, SPOCK2, and CCL2. A large-MSC population can be about 65, 70, 75, 80, 85, 90, 91, 92, 93, 94, 95, 96, 97, 98, 99%, or more large-MSCs, as a percentage of all MSCs or as a percentage of all cells.

"Throughput" refers to the amount of cells that a given modality (e.g., of biophysical sorting) can accept, e.g., by injection, and process in a given period of time. In some embodiments, the modalities for biophysical sorting used in the present have a throughput of at least about: $1\times10^3$, $5\times10^3$, $1\times10^4$, $5\times10^4$, $1\times10^5$, $5\times10^5$, $1\times10^6$, $5\times10^6$, or more, cells/minute. Preferably, these modalities maintain high cell viability (e.g., at least 80, 85, 90, 91, 92, 93, 94, 95, 96, 97, 98, 99%, or more, viability) following the sorting.

"Conditioned medium" is a medium, such as growth medium, that has been contacted with a cultured cell population (such as large-MSCs) for a sufficient time to collect secreted factors, such as proteins, such as cytokines and growth factors, from the cultured population of cells.

"Small-MSCs" and the like are MSCs with a diameter of about 12-16 μm (e.g., 14.8+/×2.4 μm) and one or more of: decreased osteoprogenic activity, increased adipogenic potential, decreased secretion of one or more of IL-6, IL-8, VEGF, BMP2, EGF, FGF1 and Ang-1, relative to large-MSCs or a mixed MSC population, and expression of one or more (e.g., 1, 2, 3, or all 4) of USP1, CCNL2, PODXL, CXCL12, or HMGN1. A small-MSC population can be about 65, 70, 75, 80, 85, 90, 91, 92, 93, 94, 95, 96, 97, 98, 99%, or more small-MSCs, as a percentage of all MSCs or as a percentage of all cells.

The invention also provides methods of mediating tissue repair (e.g., treating a condition characterized by a need for tissue repair, such as osteonecrosis, damaged vessels, or HSC transplantation following chemotherapy and/or radiotherapy) in a subject using an effective amount of large-MSCs or conditioned medium from these cells.

A "subject" refers to a mammal, including primates (e.g., humans or monkeys), cows, sheep, goats, horses, dogs, cats, rabbits, guinea pigs, rats, mice, or other bovine, ovine, equine, canine, feline, rodent or murine species. Examples of suitable subjects include, but are not limited to, human patients. While subjects may be of any stage of life and any age, e.g., neonate, infant, toddler, child, young adult, adult, or geriatric, in particular embodiments the subject is an adult, e.g., a human adult, i.e., about 18 years old, or older, e.g., about: 18-70 years old, 20-60 years old, 25-55 years old, 25-50 years old, 30-50 years old, or 25-65 years old, as well as greater than about: 30 years old, 40 years old, 50 years old, 60 years old, 70 years old, 80 years old or 90 years old.

As used herein, the terms "treat," "treating," or "treatment" mean to counteract a medical condition so that the medical condition is improved according to a clinically acceptable standard. Conditions to be treated by the methods provided by the invention include arthritis, treatment of nonunions, bone fractures, and osteochondral defects.

As used herein, a "therapeutically effective amount" is an amount sufficient to achieve the desired therapeutic or prophylactic effect under the conditions of administration, such as an amount sufficient to treat a given condition. The effectiveness of a therapy can be determined by one skilled in the art using standard measures and routine methods.

In certain embodiments, large-MSCs are administered at a dose of about: $1\times10^6$, $2\times10^6$, $5\times10^6$, $1\times10^7$, $2\times10^7$, $5\times10^7$, $1\times10^8$, $2\times10^8$, $5\times10^8$ cells/kg, or more. Effective dosages achieved in one animal may be converted for use in another animal, including humans, using conversion factors known in the art. See, e.g., Reagan-Shaw, et al., *FESEB J.* 22:659-61 (2008); Schein, et al., *Clin. Pharmacol. Ther.* 11: 3-40 (1970); and Freireich, et al., *Cancer Chemother. Reports* 50(4):219-244 (1966). For example, human equivalent dosing (HED) in mg/kg based on animal dosing may be given by the following equation: HED (mg/kg)=animal dose (mg/kg)×($Km^{animal}/Km^{human}$), where Km=weight/surface area (kg/m²). Exemplary conversion factors based on the above equation are shown in Table 1.

TABLE 1

| | From: | | | | |
| --- | --- | --- | --- | --- | --- |
| To: | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

The cell culture methods described herein can be employed to culture an MSC-containing population cells to produce an MSC population with enhanced regenerative potential (e.g., to enrich the cell population with large-MSCs). The MSC-containing population can be derived from bone marrow aspirates via ficoll density centrifugation and plastic adherence. An MSC-containing population of cells is cultured in a culture medium. Preferably, the MSC-containing cell population is cultured to a confluence of at least 80%, but less than 100%. Even more preferably, the MSC-containing cell population is cultured to a confluence of 80% to 90%. When cultured to a confluence of 80% to 90%, some parts of the flask will have greater than 90% confluence, and potentially even up to 100% confluence, in part due to the random manner in which MSC cells grown on surfaces.

Typically, the cells can be cultured for between 1 to 6 population doublings, though the cells can optionally be cultured for more than six population doublings. Every two population doublings roughly corresponds to passaging approximately once. After four population doublings, a small number of large-MSCs begin to form. These large-MSCs can be biophysically sorted for use in the therapeutic methods described herein.

Typically, the initial population of cells $P_0$ is the cells that have been extracted from a tissue source, such as bone marrow. When $P_0$ is defined as the extracted population, then four population doublings is usually sufficient to observe a small number of large-MSCs. However, if a cell culture is started from an MSC population that has already been grown out or cultured, then fewer than four population doublings are typically necessary in order to observe the formation of large-MSCs. In other words, the number of population doublings generally refers to the number of population doublings after the cells have been extracted from a tissue source.

Usually, the MSC cell population is cultured in cell culture flasks. Alternatively, the MSC cell population can be cultured in a bioreactor containing suspended 3-D spheroids. Cell confluence can be more difficult to establish in a bioreactor, though the number of population doublings is still measurable.

Optionally, the MSC-containing population of cells can be trypsinized after doubling the population. Trypsinization is performed in order to lift or detach the suspended cells from the culture flasks, particularly at lower numbers of population doubling.

The culturing and optional trypsinization can be repeated so that the MSC-containing population of cells achieves a desired number of population doublings. Typically, four population doublings is adequate to produce an MSC population with enhanced regenerative potential. Sometimes, more population doublings may be required, such as six to twelve population doublings, or sometimes even more.

Preferably, the culture medium contains Dulbecco's Modified Eagle's Medium and fetal bovine serum. Preferably, the Dulbecco's Modified Eagle's Medium is low glucose. High glucose has been observed to decrease the overall cell expansion, and hence lower glucose is generally preferred. Preferably, the culture medium contains about 10% fetal bovine serum.

Starting with about 1000-1500 MSCs/cm$^2$, the typical culture time for culturing in flasks to about 80% to about 90% confluence is about 7-10 days. Growth rates have been observed to decrease as cells are expanded, so subsequent cell passages or population doublings may take longer to reach 80-90% confluence. Generally, the cells are not grown for longer than two weeks in the same flask. When culturing in a bioreactor, the MSC-containing population of cells can continue expanding in the same reactor for about 2-3 weeks because it is a scaled up batch process.

Optionally, a portion of the MSC-containing population of cells can be cryopreserved in a cryopreservation medium after performing one or more population doublings. Preferably, the cryopreservation can occur after about four to about six population doublings, which roughly corresponds to about two or three passages. Alternatively, or in addition, the cryopreservation can occur after substantially more population doublings, such as about twelve population doublings, which roughly corresponds to about six passages. The cryopreservation medium can include Dulbecco's Modified Eagle's Medium, fetal bovine serum, and dimethyl sulfoxide. Preferably, the cryopreservation medium consists essentially of 70% Dulbecco's Modified Eagle's Medium Low Glucose, 20% fetal bovine serum, and 10% dimethyl sulfoxide. The cryopreserved MSC-containing population of cells can be thawed at a later date. Preferably, the cryopreserved cells are washed with saline after being thawed. Preferably, the saline is supplemented with human serum albumin. Even more preferably, the saline is supplemented with about 1% human serum albumin.

The cell culture methods can be combined with the biophysical sorting methods. In other words, the cell culture methods can be performed to increase the amount of MSC-containing cells, which can subsequently be sorted by the biophysical methods described herein. The sorted MSCs can be further used in the therapeutic methods described herein.

A description of example embodiments of the invention follows.

EXEMPLIFICATION

Materials and Methods

Mice.

NOD/SCIDs and NOD/SCID/gamma (NSG) mice were from the Jackson Laboratory and bred in the animal facility at the National University of Singapore. All animal experimentation was performed in accordance with the guidelines set forth by the IACUC of the National University of Singapore. 8-12 week old mice were used in our studies. Mice that received total body irradiation (RS 2000 Biological Research Irradiator) were allowed to recover for 24 h after the procedure before further experimentation. Cells were systemically injected via the tail vein. For 5-ethynyl-2'-deoxyuridine (EdU) experiments, ~200 μg of EdU was injected i.p. 24 h before euthanizing and harvesting of relevant tissues. Tomato-lectin was injected 30 minutes before mice euthanasia.

Cell Culture.

Bone marrow (BM) derived MSCs and HSCs were obtained from a commercial source (Lonza). MSCs in the first culture passage were isolated from a healthy donor derived BM aspirate via ficoll density centrifugation and plastic adherence. The MSCs were then culture expanded from passage 2 until passage 9 for this study at cell seeding densities of 1000 MSCs/cm$^2$. MSCs were cultured in each passage until 90% confluence or for a maximum of 7 days. All MSCs were maintained in low glucose DMEM supplemented with 10% FBS and 5% Penn/Strep (Invitrogen). HSCs were cultured for 7 days in HPGM (Lonza) supplemented with SCF, TPO and Flt-3 ligands (100 ng/mL each). MSC secretome was collected by incubating equal numbers of MSCs (70% confluence) in serum free DMEM for the indicated amount of time. This supernatant was then filtered through a 0.45 μm syringe filter before use. This supernatant is further concentrated using a 3 kDA MWCO Amicon Ultra centrifugal filter to volumes appropriate for in vivo injection.

MSC Microfluidic Sorting.

Trypsinized MSCs were resuspended in media and sorted into the large- and small-MSC fractions using a microfluidic device. A sorting throughput of 3 million MSCs per minute was used in our experiments. Sorted MSCs maintained a high viability of >95% as determined via live dead staining. All subsequent assays were performed on freshly sorted cells.

Antibodies, Staining and Flow Cytometry.

Unless otherwise stated, all antibodies used in this study were purchased from R&D Systems. β2-microglobulin antibody was from Millipore. Annexin V (Alexa 488) and PI (Invitrogen) were used in apoptosis and viability assays. EdU staining was performed using the Click-iT imaging kits (Invitrogen). Cell cycle analysis on FACS was performed using Ki-67 and 7-AAD co-stained cells. Adherent cells or histological sections were fixed in 4% paraformaldehyde, permeabilized as needed with Triton X-100 and blocked with 1% BSA before staining. For flow cytometry, prepared cells were blocked with 1% BSA before staining. Flow cytometry analyses were performed using a LSRII system (BD Biosciences).

Quantitative RT-PCR Analysis.

Total RNA was prepared from MSCs using QIAGEN RNeasy Mini Kit and was used without modification in subsequent PCR analyses. The relative amount of each transcript was determined by real-time RT-PCR using the ABI StepOnePlus instrument and the Express One-Step SYBR GreenER Kit (Invitrogen), according to the manufacturer's instructions. For primer sequences, see FIG. 13. The $2^{-ddCt}$ method was used to analyze the results using GAPDH as the housekeeping gene. RTPCR was performed in triplicate and thermal cycle conditions were 50° C. for 2 min, 95° C. for 10 min, then 50 cycles at 95° C. for 15 sec and 60° C. for 1 min.

In Vivo Bioluminescence and Fluorescence Imaging.

To track the luciferase-transformed cells, D-luciferin (Xenogen) was injected intraperitoneally at a dose of 150 mg luciferin/kg, 10 minutes before imaging. Bioluminescence images were collected on a Xenogen IVIS Spectrum Imaging System (Xenogen) and the Living Image software was used to acquire and analyze the results. Mice were anesthetized with isoflurane during the image acquisition process.

For fluorescence imaging of MSC mineralization, OsteoSense 800 (EX: 745 nm, EM: 800 nm) was injected via the tail vein 24 h before the ectopic bone scaffolds were extracted and imaged. For fluorescence imaging of angiogenesis, AngioSense 750 (EX: 750 nm, EM: 780 nm) was injected via the tail vein 24 h before the mice were imaged under anesthesia.

HSC Biodistribution.

HSCs were labeled with Xenolight (Xenogen) as per the manufacturer's instructions and injected into sublethally irradiated NSG mice with or without MSCs as co-injection. After 24 h, indicated tissues were removed, weighed and macerated in well plates. The Xenolight signal in HSCs was quantified using the IVIS Spectrum imaging system and ROI tools in the living image software. Biodistribution was calculated as the percentage of recovered fluorescence per mg tissue.

MSC Trilineage Differentiation Assay and Quantification.

For adipogenic induction, MSCs were plated at $2\times10^4$ cells/$cm^2$ and cultured in adipogenic differentiation medium (DMEM supplemented with 5 µg/ml insulin, $10^{-6}$ dexamethasone, and $0.6\times10^{-4}$ indomethacin) for up to 3 weeks, with medium exchanges three times per week. To visually detect cytoplasmic lipid accumulation, cultures were fixed in 4% paraformaldehyde for 20 min and stained with 0.3% Oil Red O (Sigma-Aldrich) in 0.6% isopropanol for 1 h. The content of Oil Red O in samples was quantified by extraction with 100% isopropanol for 5 min followed by spectrophotometry quantification at 510 nm, as described in Sekiya, I., et al., *Stem Cells* 20, 530-541 (2002). For osteogenic induction, MSCs were plated at $2\times10^4$ and cultured in osteogenic differentiation medium (DMEM supplemented with 10 mM (β-glycerophosphate, $10^{-8}$ M dexamethasone, and 0.2 mM ascorbic acid) for up to 14 days, with medium changes three times per week. Extracellular accumulation of calcium was assessed by Alizarin Red S staining. The stained monolayer was extracted with 10% acetic acid (v/v) and neutralized with 10% (v/v) ammonium hydroxide followed by colorimetric quantification at 405 nm, as described in Gregory, C. A., Gunn, W. G., Peister, A. & Prockop, D. J., Analytical Biochemistry 329, 77-84 (2004). For chondrogenic differentiation, MSCs were pelleted and cultured in chondrogenic differentiation medium (DMEM supplemented with 0.1 µM dexamethasone, 0.17 mM ascorbic acid, 1.0 mM sodium pyruvate, 0.35 mM L-proline, 1% insulin-transferrin sodium-selenite (Themo Fischer Scientific, Singapore), 1.25 mg/ml bovine serum albumin, 5.33 µg/ml linoleic acid, and 0.01 µg/ml transforming growth factor-β) for 28 days with medium changed three times per week. The micromass pellets were formalin fixed, paraffin embedded, and sectioned in 10 µm slices. Thereafter, they were dewaxed and rehydrated before Alcian Blue (Sigma-Aldrich) staining. Cells were then rinsed three times with distilled water and the amount of cell-associated dye was measured at 620 nm, after extraction with 6 M guanidine-HCl (Sigma-Aldrich), as described in Nishigaki, F., et al., *European Journal of Pharmacology* 437, 123-128 (2002).

MSC Bone Ectopic Assay.

Equal numbers of MSCs (300K cells per 125 $mm^3$ volume of scaffold) were loaded onto Polycaprolactone-tricalcium phosphate (PCL-TCP) 3D bioactive scaffolds (Osteopore International) in a fibrin gel (Sigma-Aldrich). The scaffolds were treated with 5M NaOH for 3 h to enhance hydrophilicity and washed thoroughly with PBS thrice prior to ethanol sterilization. Scaffolds were then conditioned in osteogenic differentiation medium for 1 week before implantation. The cumulative fluorescent signal from each scaffold was quantified with ROI tools in the living image software.

Chimerism.

The level of human HSC engraftment was analyzed with chimerism in the hematopoietic system and was quantified as follows: % $CD45^+$ human cells/(% $CD45^+$ human cells+% CD45+ mouse cells).

Histology and Tissue Processing for Analysis.

For histology, harvested tissue samples were frozen in the Tissue Tek O.C.T compound and cryo-sectioned before staining and analysis.

For isolation of BM cells, whole BM tissue was flushed from femurs and passed through a 70 µm nylon sieve to first break up cell clumps. The dispersed cells were then centrifuged and treated with RBC lysing solution (Sigma-Aldrich) for 5 minutes at room temperature to remove the RBCs. The remaining BM cells were re-centrifuged and resuspended in the appropriate buffer for analysis.

For isolation of the mononuclear fraction, whole BM tissue flushed from femurs was first passed through a 70 µm to break up cell clumps, resuspended in PBS and applied to Ficoll-Paque (GE healthcare) for density centrifugation at 400× g for 45 min at 20° C. The mononuclear cells were then recovered and transferred to colony forming units in culture (CFU-C) assays in human growth factor supported methycellulose media (R&D systems).

RBC lysing solution (Sigma-Aldrich) was added to blood samples and allowed to incubate for 5 minutes at room temperature. The lysed RBCs were removed by centrifugation and the remaining cell pellet was resuspended in the appropriate buffer for analysis.

In Vitro Human Colony Forming Cell Assay.

HSCs or mononuclear cells were suspended in complete methylcellulose media as per the manufacturer's instructions (R&D systems). The cultures were left to incubate at 37° C. and 5% $CO_2$. Colonies were scored after 14 days.

Retroviral Vectors and Viral Production.

Human MSCs in the second passage and human HSCs in the first passage were transduced with a firefly luciferase gene in order to investigate their real-time biodistribution after systemic injection. The firefly luciferase gene was introduced retrovirally using the Phoenix-AMPHO packaging cell line producing the pMSCV-puro-Firefly luciferase viral supernatant. Transduced cells were selected for by the addition of 2 µg/ml of puromycin in the respective growth media for 3 days.

HUVEC Sprouting on Bead Assay.

RFP-transduced HUVEC cells were cultured on Cytodex microcarrier beads (Sigma-Aldrich) and suspended within a fibrin gel (2.5 mg/mL) matrix, as described in Ghajar, C. M., et al., *Exp Cell Res* 316, 813-825 (2010). The concentrated secretome collected from MSCs was used as media and replaced every 2 days. RFP-HUVECs were observed under a fluorescent microscope for angiogenic sprouting from the microcarrier bead surface.

Femoral Explants.

Whole femurs from lethally irradiated mice were harvested from mice 7 days after and the femoral head was sectioned to expose part of the BM tissue. These femurs were then embedded in a collagen gel (1.5 mg/mL) and exposed to a concentrated secretome from the different MSCs over a period of 14 days. The concentrated secretome-media was replaced every 4 days.

Luminex and ELISA Assays.

The Bio-Plex Pro Human Cytokine Kit (Biorad) and elisa (R&D Systems) were used in combination to survey the secretome of MSCs. MSC-conditioned media was used in these assays as per the manufacturer's instructions and the final detected analyte concentration was reported.

Cell Culture Protocol.

The following protocol can be used to generate a large-MSC population. FIG. 17 shows a workflow for a smaller-scale MSC culture. FIG. 18 shows a workflow for larger-scale MSC culture. Some of the steps are optional. For example, if long term storage of MSCs is not desired, then cryopreservation need not be performed. Additionally, trypsinization after each population doubling is also optional.

Step 1: Culture of MSCs. The complete media used is Dulbecco's Modified Eagle's Medium (DMEM), preferably Dulbecco's Modified Eagle's Medium Low Glucose (DMEM-LG) supplemented with 10% fetal bovine serum (FBS). MSCs are derived from bone marrow aspirate and grown out to about 90% confluence in a T175 at $P_0$. After cells reach 80-90% confluence, they are trypsinized and stored in batches of ~1 million cells/vial for $P_1$ culture. One vial of cryopreserved MSCs ($P_1$) is thawed and washed before placing the cells in a T175 flask with a culture volume of 30 ml. Subsequent media change is performed at every 3-4 days until the cells reach 80-90% confluence. For trypsinization, the MSC layer is washed with 15 ml of saline followed by a 5 minutes incubation at 37° C. with 5 ml of trypsin (1000× dilution with PBS-EDTA buffer). After all the cells have detached, 19 ml of saline is added and the cell suspension is centrifuged at 500 g for 5 minutes, 20° C. After trypsinization, for passage 2-3, a portion of cells is cryopreserved in cryovials while another portion of cells is placed in culture for further expansion (1000-1500 cells/$cm^2$); for passage 4-5, the cells are passaged into triple flasks for further expansion (1000-1500 cells/$cm^2$).

Step 2: Isolation of osteoprogenitor MSCs after culture. Isolation of MSCs is carried out after trypsinization of cells at passage 6. Cells are resuspended in MSC media at concentration of up to $1 \times 10^6$ cells/ml. The cells are transferred to 20 ml syringes and injected through the microfluidic-sorting device at a speed of 3.5 ml/min with the use of a syringe pump. The desired subpopulation cells is collected at the outlet and cryopreserved.

Step 3: Cryopreservation of MSCs. The MSCs are cryopreserved in cryopreservation media that consists of 70% DMEM, preferably DMEM-LG, 20% FBS and 10% dimethyl sulfoxide (DMSO). The cells are cryopreserved in either cryovials (for passage 2, 3) or in cryobags (for passage 6) at a concentration of $1-5 \times 10^6$ cells/ml. Cryopreservation is performed using a controlled rate freezer.

Step 4: Thawing and washing of MSCs before fresh infusion of cells. This process is performed to simulate the actual infusion of cells for the clinical trial. The MSCs are thawed using a 37° C. waterbath and transferred to a 600 ml transfer bag. The cells are washed twice with saline supplemented with 1% human serum albumin (HSA) for centrifugation at 1000 g, 5 mins, 20° C. The cells are resuspended in, saline supplemented with 1% HSA at a concentration of $0.5-1.0 \times 10^6$ cells/ml.

Discussion

Since their discovery and demonstration of clonal multilineage differentiation potential, bone marrow (BM) derived multipotent mesenchymal stromal cells (MSCs) have generated considerable interest within the biomedical community as leading candidates for cell-based tissue regenerative therapies, with the implicit idea that they function as self-renewing stem cells that replace damaged tissue. However, retrospective clinical and laboratory data show little evidence of a therapeutic effect being mediated by engraftment, assimilation and terminal differentiation of administered MSCs into resident cells of the defective tissue. Even in cases where MSCs were reported to have engrafted or functionally assimilated as part of the host tissue, not only was their frequency in host tissue exceedingly low, but the cells that did engraft also failed to persist in the presumed site of activity relative to the observed recovery period. On the other hand, studies documenting the secretome of cultured MSCs indicate that a multitude of beneficial factors relevant to tissue repair are produced, which further demonstrated efficacies for tissue repair. Therefore, despite initial ideas about the therapeutic mechanisms of MSCs, it is now widely accepted that these cells do not function primarily as "building blocks" for tissue regeneration but rather as "cellular factories" that secrete factors to facilitate tissue recovery on many potential levels, including the stimulation of endogenous stem/progenitor cells, cell proliferation and angiogenesis, as well as the suppression of inflammation and cell death.

Strategically, this paradigm shift has important consequences for MSC development as regenerative therapies. First is the implication that their potency may not be reliably predicted by their 'stemness,' as defined by their ability to self-renew or undergo multilineage differentiation, but critically determined by their tissue or microenvironment of origin. It has been established that MSCs derived from adipose tissue, umbilical cord and BM have different gene expression profiles even though they possess the same capabilities for multipotent differentiation. The secretome of these MSCs could therefore vary greatly depending on the biologic relationship between the MSCs and their tissue of origin, and must be verified preclinically before their use as a therapeutic. Second, and related to the preceding point, is the possibility that relevant therapeutic factors may only be present or enhanced in the secretome of the lineage-committed progenies derived from previously uncommitted MSCs. Uncommitted MSCs play out a therapeutic role in vivo by developing into progenitors that have biological properties more advantageous for performing the necessary reparative actions. Because the natural process of recovery is actually mediated by mesenchymal progenitor cells further along in their level of commitment, these cells could potentially be more effective in delivering a therapeutic punch versus uncommitted MSCs.

Recent investigations of the physiological roles of MSCs and their progenitors within the marrow have provided insight for their different possible therapeutic values. Within the BM, literature observations have alluded to a connection between MSCs with high osteogenic activity and the capabilities for microenvironmental repair as well as HSC support, which are both critical for BM homeostasis. For example, genetic pulse-chase experiments have showed that osteoblastic MSCs responsible for repairing bone tissue injury are transient, non-proliferative cells that require replenishment from a pool of uncommitted MSCs precursors. Similarly, other studies investigating the effects of irradiation or similar myeloablative procedures demonstrate that during BM recovery, the surviving perivascular MSCs highly expand and undergo a reversible and transient shift towards a state of higher osteogenic activity. This was indicated by an increased expression of osteoblastic differentiation markers, such as alkaline phosphatase, osteopontin, osteocalcin and runx2 during the recovery period, which subsequently returned to ambient levels in fully regenerated BMs. Conversely, adipogenic MSC activity, which is often thought to be antagonistic to osteogenicity, has typically been associated with myelosuppression and decreased hematopoiesis. In further support of the hematopoietic supporting capabilities of osteogenic MSCs, it has been determined that naïve HSCs and mature osteoblasts constitute at least one of many stem cell niches residing in the marrow. Under ambient conditions, these endosteal HSC niches maintain a functional hematopoietic system and signaling information derived from osteoblasts, via secreted growth factors and integrin binding, are critical for this effort. It has also been shown that genetic alterations to osteoblasts within these environments can be an initiating lesion for a multistep progression to hematologic cancers.

The means to produce therapeutically relevant numbers of MSCs that are manipulated towards an osteoprogenitor state could therefore have significant impact for applications in BM or hematopoietic repair. Osteoblasts or pre-osteoblasts cannot be isolated from bone BM aspirates, because they adhere too strongly to bone and require enzymatic treatment for their extraction. MSCs found in typical bone marrow aspirates are predominately found in the perivascular BM space, and have the ability to generate osteoprogenitor intermediates and, eventually, osteoblasts that line the bone surface in vivo. This capability for osteogenic commitment is retained ex vivo, but it occurs in an uncontrolled and stochastic manner during culture expansion. Immunophenotyping approaches for identifying osteoprogenitor MSCs, such that they can be purified from the larger population of culture expanded cells for therapeutic applications, are a possible strategy, but no unique surface marker has been discovered that can make such an approach efficient, and those that are expressed by MSCs constitutively are not useful indicators of this lineage commitment process. Several physical cell properties (cell size, membrane compliance and nucleus fluctuations) were identified as predictive of the phenotype, biology and differentiation potency of MSCs, such that knowledge of these biophysical cell differences could be exploited for label-free sorting of progenitors from other MSC types. These biophysically different MSC populations were indistinguishable via typical immunohistochemical markers. Osteoprogenitor MSCs can be conveniently distinguished and isolated from other MSC types as cells with a larger diameter (both adherent and suspended), but they also possess a stiffer membrane and a low fluctuating nucleus.

Herein, to translate these findings to clinical relevance, we utilized biophysical, label-free, microfluidic sorting to enrich culture expanded MSCs with osteoprogenitors and subsequently examined this unique MSC subpopulation for applications in BM regeneration and hematopoietic transplants. We find that osteoprogenitor MSCs are potent "cell factories" that can mediate rapid regeneration of myeloablated BMs, which fosters a conducive environment for enhanced donor hematopoietic stem cells (HSCs) homing and engraftment kinetics. Although our work primarily investigates the use of these cells for BM tissue repair, other medical indications treatable with tissue regeneration could also benefit from the application of these sorted cells.

Results

Label-Free, High-Throughput Sorting of Large-MSC Osteoprogenitors

Figure 1D:
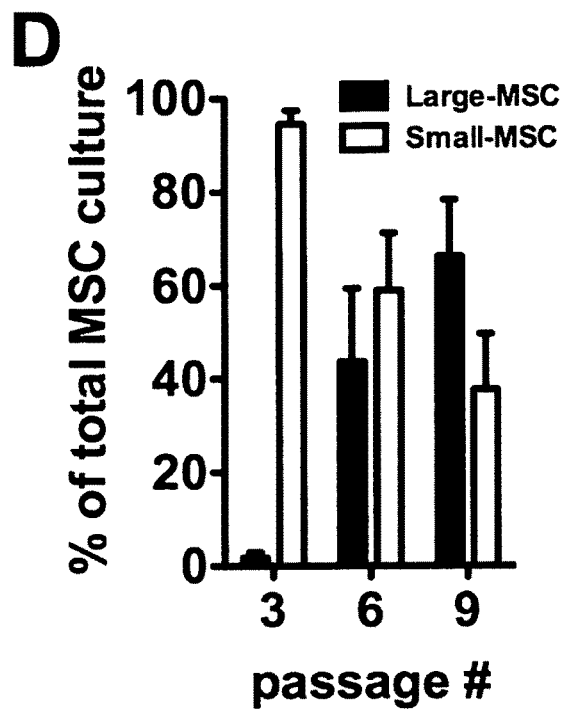
Figure 6:
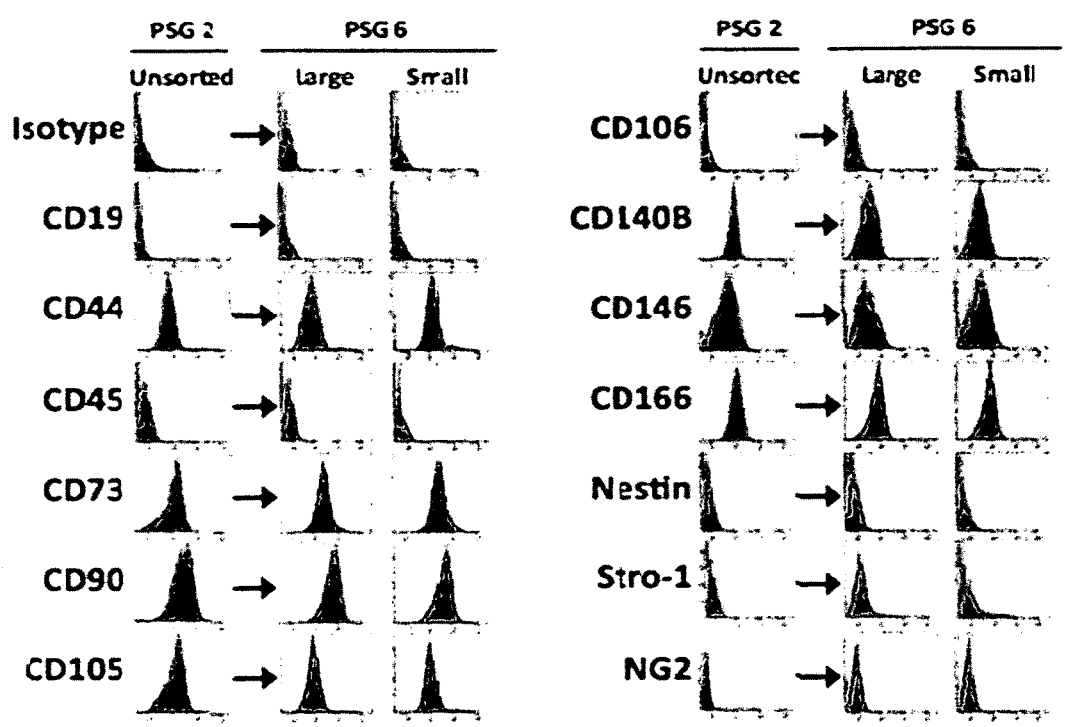
FIG. 6 shows representative FACS histograms of mesenchymal stromal cells (MSCs) in this study at passage 2 (PSG 2) and for sorted large- and small-MSC fractions at passage 6 (PSG 6). No significant differences were observed for all tested MSC surface markers that could be used to identify large-MSCs from total cultures.
Figures 7A, 7B:
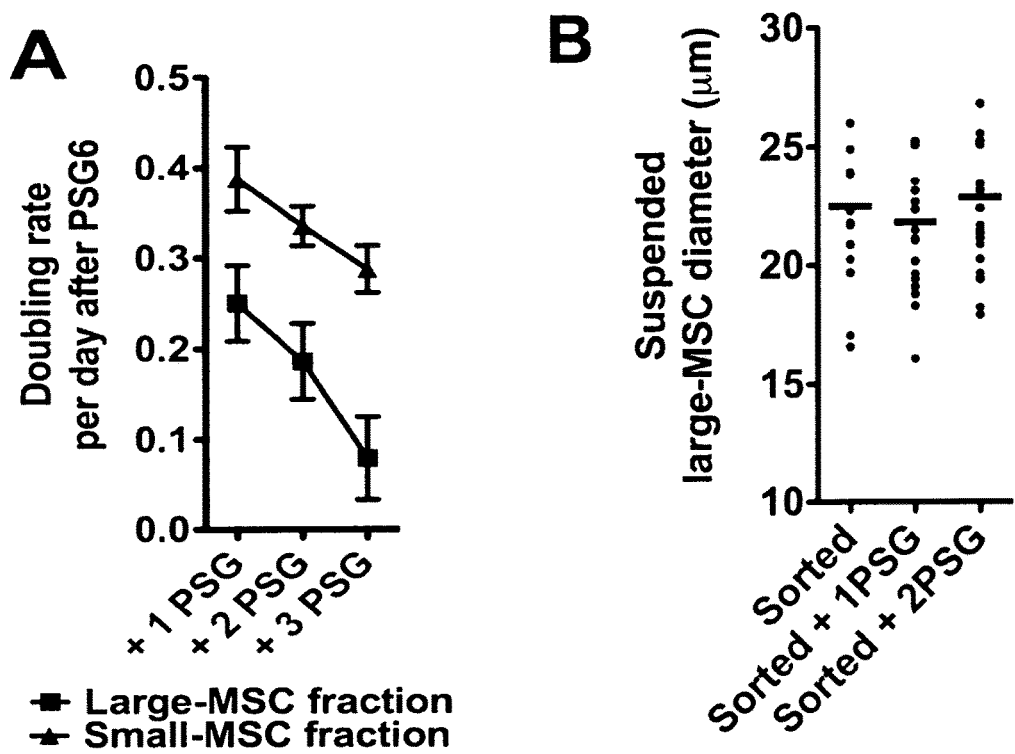
FIG. 7A shows proliferation of large- and small-MSC fraction cells after microfluidic sorting at PSG 6. Large-MSCs are a less proliferative fraction of cells.
FIG. 7B shows the average suspended cell diameter of the large-MSC fraction cells during passaging after sorting at PSG 6. Cells in this fraction remained large and did not revert to a smaller size.

Our study was conducted using MSCs isolated from BM aspirates via ficoll density centrifugation and plastic adherence; this process is designated as the first passage (PSG) of MSC culture. MSCs were further culture expanded using conventional protocols (see *Materials and Methods* section) over a maximum of 9 PSGs. At PSG 2, MSCs were uniform in morphology and size and also expressed surface markers CD44, CD74, CD90, CD105, CD140B, CD146 and CD166 but not CD19, CD45, CD106, Nestin, Stro-1 or NG2 (FIG. 6). As previously described, we observed an increasing number of larger and flatter cells within the expanded MSCs over long-term culture, which formed a significant subpopulation within whole MSC cultures by PSGs 5-6 (FIG. 1A). To examine their therapeutic use, we utilized an inertial microfluidic sorter to perform high throughput size sorting of suspended MSCs into two outlet streams, one of which contains a population of MSCs enriched with the large-MSC osteoprogenitors (large-MSC fraction), while the other MSC stream (small-MSC fraction) is depleted of the large-MSC osteoprogenitors (FIG. 1B). A sorting throughput of up to ~3 million cells per minute was tested to give consistent size fractionation of MSCs with high viability (>95%). Extensive device testing with MSCs derived from 7 donors shows that the sorted fractions across PSGs 5-7 are consistent in size distribution (large-MSCs=21.9+/−5, small-MSCS=14.8+/−2.4, FIG. 1C) and microscopic examination of the morphology of adhered cell fractions confirmed that a significantly greater number of large, flat and irregularly shaped cells are found in the large-MSC fraction but are not present in the small-MSC fraction (FIG. 1B). At PSG 6, a >5 fold enrichment (via visual inspection) of MSC osteoprogenitors in large-MSC fraction cultures versus unfractionated cultures was achieved after microfluidic sorting. FIG. 1D shows the extent recovery of each MSC fraction after microfluidic sorting across the typical culture life of MSCs; the increasing large-MSC fraction recovery over later passages, together with their lack of proliferation capacity, as well as the consistency of cell size and morphology compared to the small-MSC fraction after sorting (FIGS. 7A and 7B), suggests that large-MSCs are generated from cells within the small-MSC fraction and stay as large, flat cells which accumulate in whole MSC cultures with increased passaging.

Figure 1E:
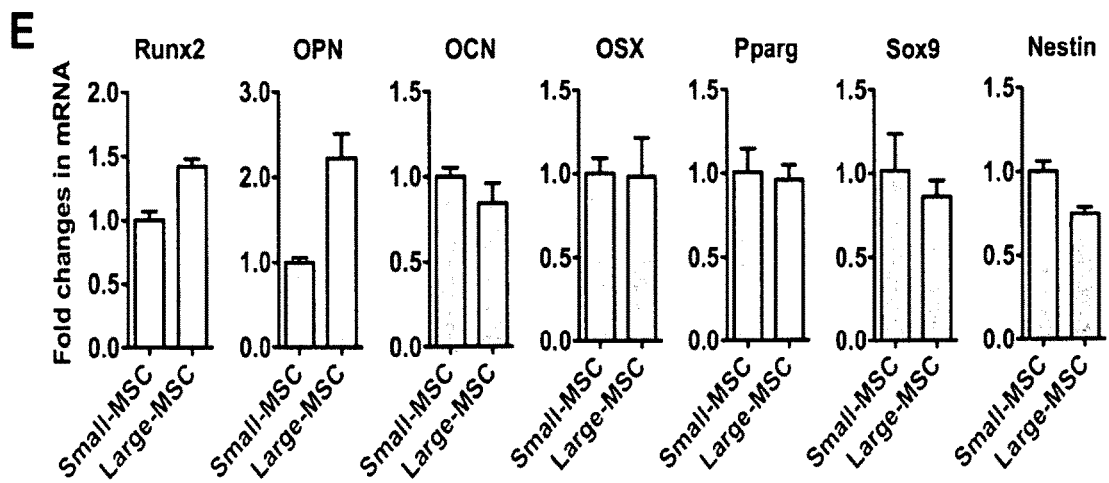
Figure 1F:
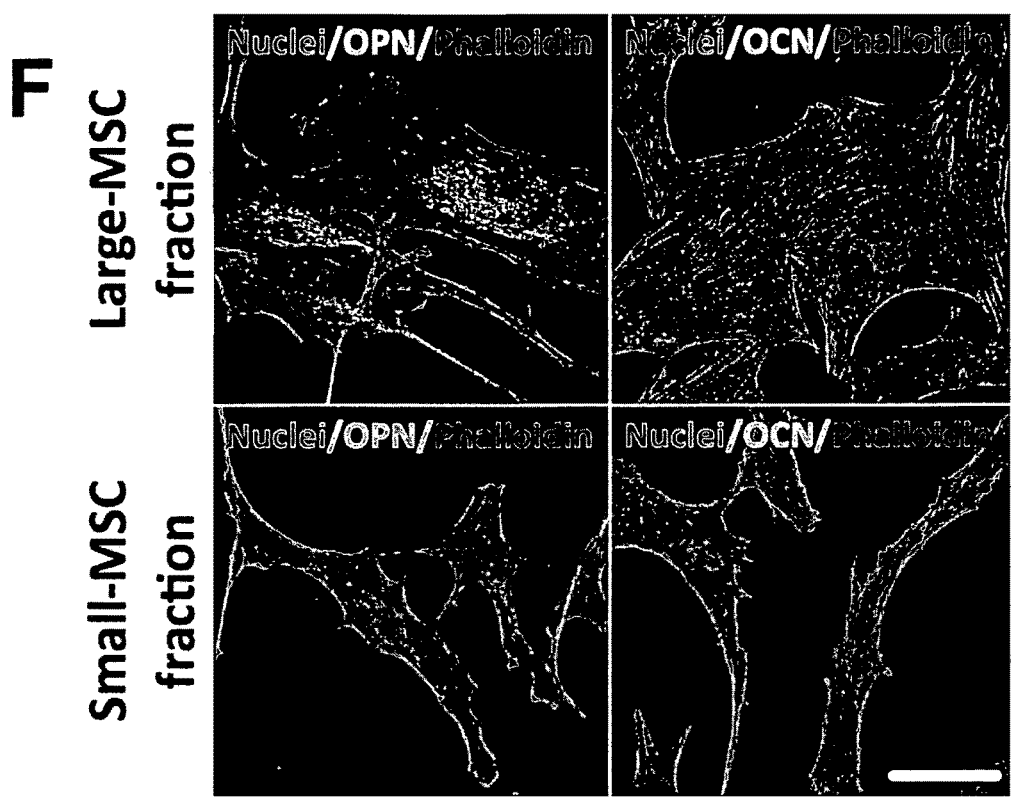
Figure 1G:
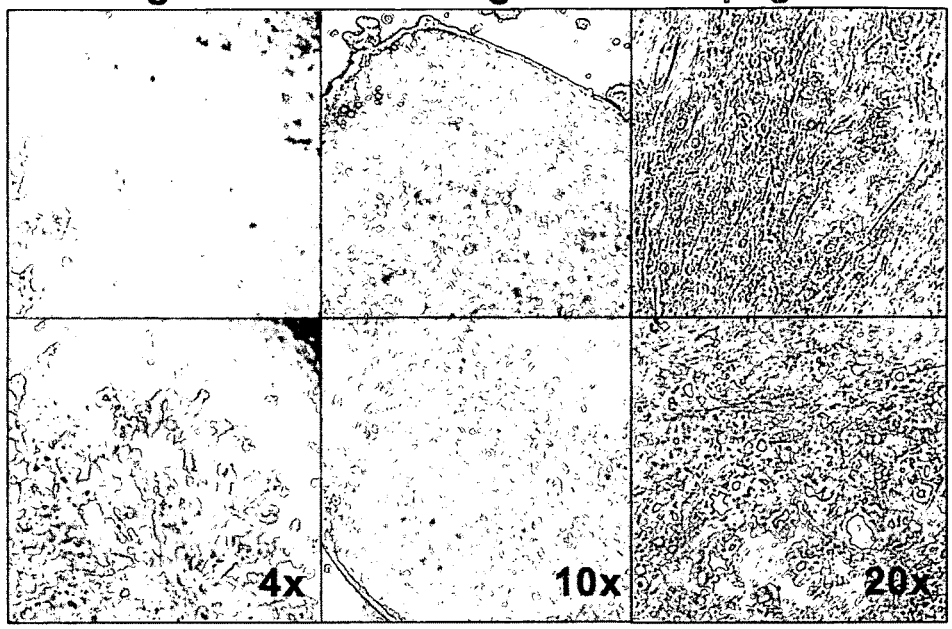
Figure 1H:
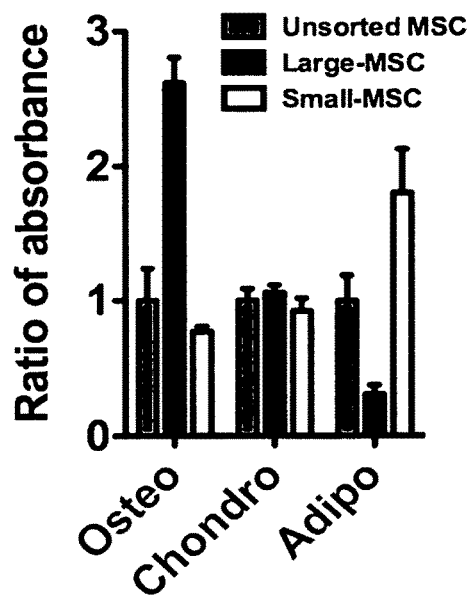
Figure 1I:
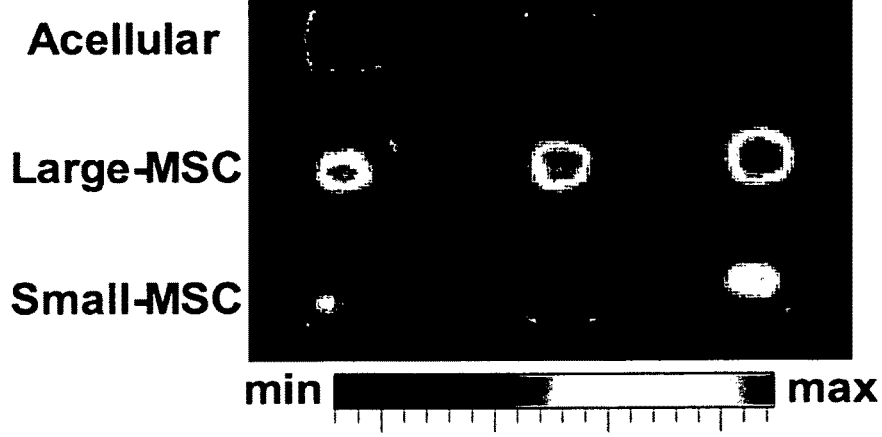
Figure 1J:
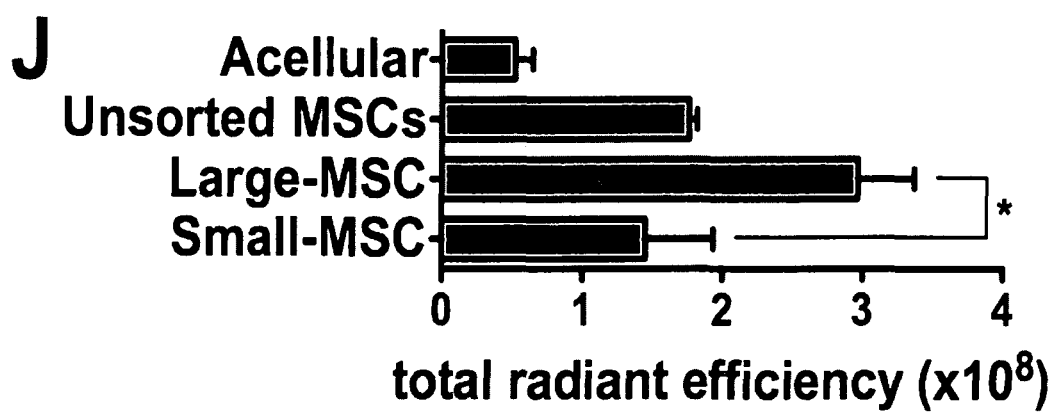
Figure 7C:
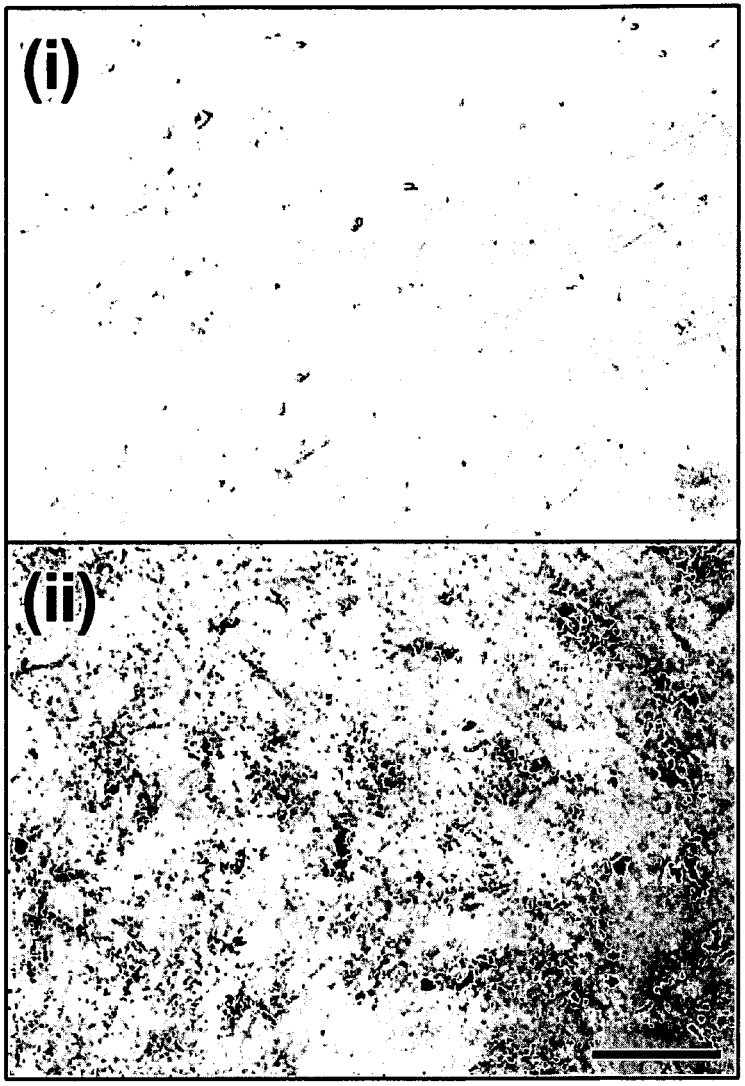
FIG. 7C shows bright field images of adherent large-MSCs (i) and MSCs under chemical osteogenic induction to osteoblasts (ii) after 2 weeks in culture. Large-MSCs are not fully committed osteoblasts and do not mineralize under ambient conditions. Scale bars=200 µm. All values are given in mean sd unless otherwise stated.

The Large-MSC Fraction has Bulk Properties of a Lineage-Restricted MSC Osteoprogenitor Phenotype Experimental evidence for the osteoprogenic nature of the large-MSC fraction sorted via the microfluidic device described herein comes from genetic and functional assays. First, RTPCR analysis showed an increased expression of early osteogenic transcripts (osteopontin and runx2) in the large- vs small-MSC fraction but no differences in late osteogenic (osteocalcin), adipogenic (pparg) or chondrogenic (sox9) transcript expression (FIG. 1E). Antibody staining detected a significant level of osteopontin only in cells from the large-MSC fraction, and osteocalcin was not detected in either MSC fraction (FIG. 1F). In vitro tri-lineage assays comparing the differentiation potential of these fractionated MSCs demonstrated functional differences between these MSC fractions. A higher level of mineralization (~3.4×) but a lower level of oil droplet formation (~5.8×) was observed in the large- vs small-MSC fraction (FIGS. 1G and 1H), while chondrogenic differentiation potential was identical in both MSC fractions. In vivo, large-MSC fraction cells seeded onto osteoinductive scaffolds produced a greater extent of bone mineralization (~2× higher via fluorescent bisphosphonate staining, FIGS. 1I and 1J) compared to those seeded with the small-MSC fraction. Although cells in the large-MSC fraction show a greater propensity for osteogenic differentiation, they do not mineralize in culture as osteoblasts or MSCs under chemical osteogenic induction do (FIG. 7C).

Together, these observations demonstrate the increased osteogenic but diminished adipogenic phenotype of the large-MSC fraction compared to the other small-MSC fraction; however, the cells within the large-MSC fraction are not fully committed osteoblasts, and do not express late markers of osteogenic commitment (osteocalcin) or deposit minerals spontaneously in adherent culture. In contrast, the small-MSC fraction consists of MSCs with an uncommitted phenotype and tri-lineage differentiation capabilities. Despite the different functional phenotypes, cells of both large- and small-MSC fractions present a similar surface immunophenotypic profile that is consistent with MSCs from an early passage (FIG. 6).

The Large-MSC Fraction is a Potent Cell Population for Regeneration

Figure 2A:
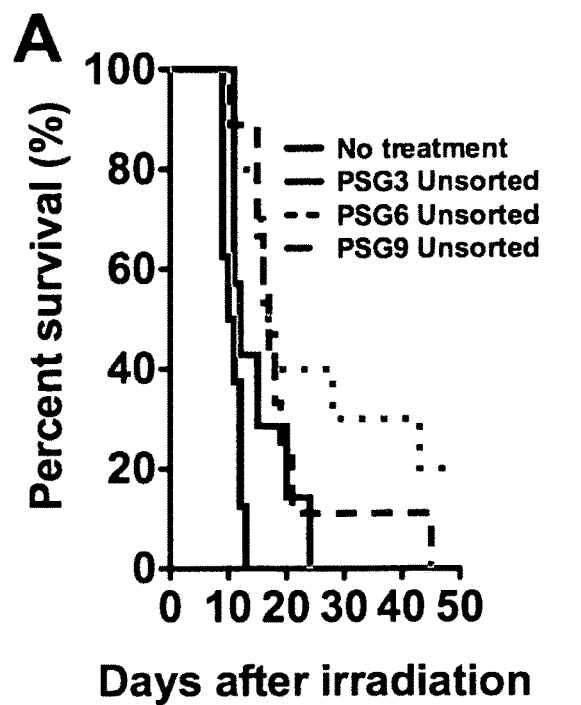
FIGS. 2A-2N show comparisons of bone marrow (BM) regenerative efficacies of systemically infused MSCs (PSG 6, for >4 donors) which demonstrate enhanced capabilities of the large-MSC fraction for rescuing BM damage in lethally irradiated NOD/SCIDs (5.0 Gy).
Figure 2B:
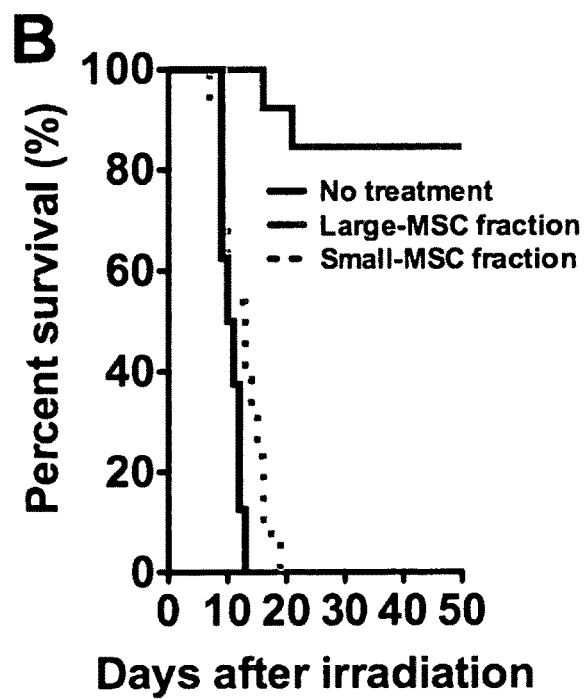
FIG. 2B shows survival of lethally irradiated (5.0 Gy) NOD/SCID mice given no treatment, large-MSCs and small-MSCs on day 1. Mean survival times are 17 days, >50 days and 13 days, respectively (n>10 mice per group, MSC dose: 20×10$^6$ cells/Kg).
Figure 2C:
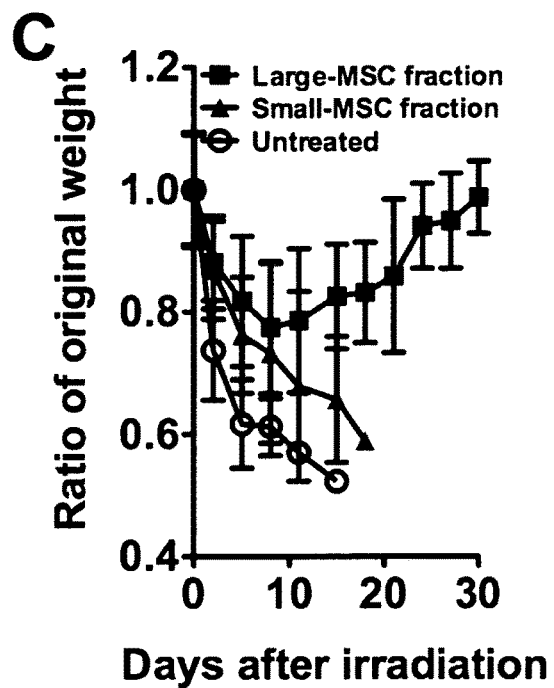
FIG. 2C shows weight change of NOD/SCIDs in FIG. 2B over a period of 30 days after irradiation.
Figure 2D:
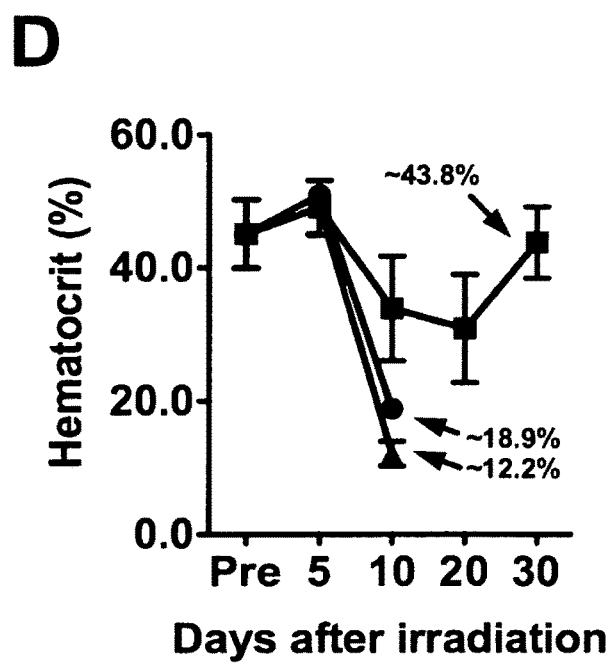
Figure 2I:
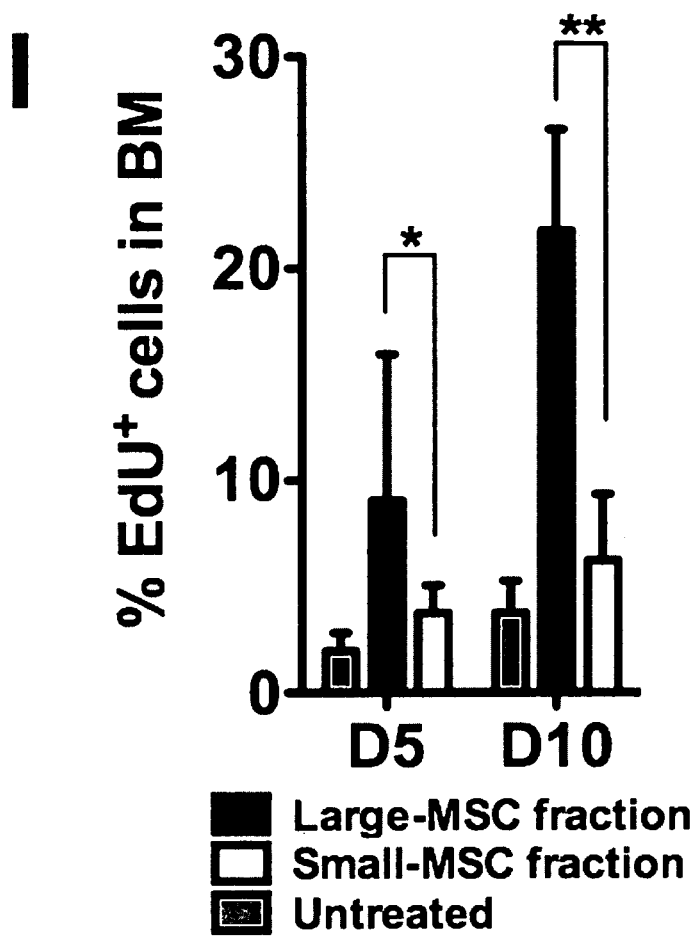
FIGS. 2I and 2J show the percentage of EdU$^+$ cells in the BM aspirate of treatment groups in FIG. 2B, showing increased cell proliferation for the large-MSC group. *P=0.3263 and **P=0.0245 for day 5 and 10, respectively (n=4 BM aspirates tested).
Figure 2J:
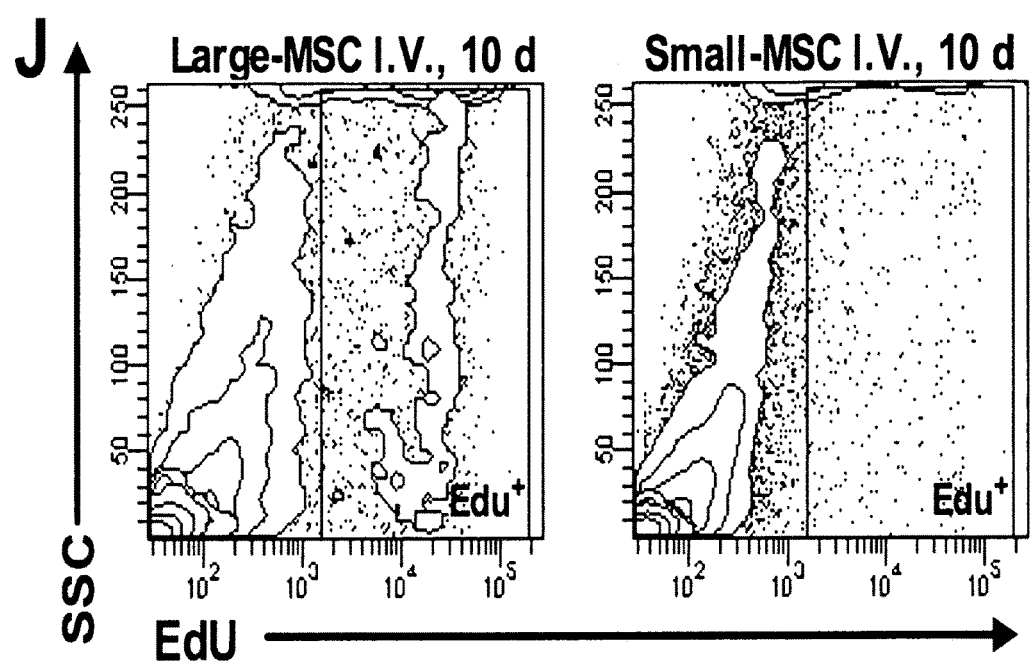

Systemically, MSC administration has been demonstrated as therapy to rescue BM damage in lethally irradiated mice; thus, a lethally irradiated (5.0 Gy) NOD/SCID injury model was used to evaluate the BM regenerative properties of different MSCs. At this dose of radiation, damage is primarily dealt to BM tissue and defects in the hematopoietic system occur subsequently as a result of BM injury. Untreated irradiated mice (n=7) succumbed quickly to radiation damage (median survival=10.5 days, FIG. 2A) and experienced rapid weight loss (~40%, FIG. 2C), as well as white blood cell (WBC), red blood cell (RBC) and platelet depletion within 5 to 10 days after irradiation (FIGS. 2D to 2F). In parallel, histological and FACS analyses revealed a severe loss of cellularity and vascular structural integrity as well as a high percentage of dead or apoptotic cells (>60%) with minimal cell proliferation activity (<5%) in the BM by day 10 (FIGS. 2G to 2J and 8A).

In initial experiments (FIG. 2A), unsorted MSCs at passages 3, 6 and 9 (n=7-10 each), were systemically administered 24 h after irradiation at dosages of 20-25×$10^6$ cells/kg. Overall, we found modest improvements in median survival times (12 days, 17 days and 17 days for passage 3, 6 and 9 MSCs, respectively) and reduced weight loss in MSC-infused mice compared to non-infused mice (~30% vs ~40% loss, respectively, within 5 days, data not shown), indicating that MSC infusions can alleviate acute ionizing-radiation lethality. Notably, 10-20% of mice in the treatment groups injected with MSCs from late cultures (PSG 6 and PSG 9) showed recovery of body weight after ~10-15 days and survived beyond 50 days, while none of the mice infused with MSC from early cultures (PSG 3) survived beyond day 25. These results suggest that the large-MSC osteoprogenitors that develop in later, but not in earlier, cultures may have properties that are beneficial towards BM regeneration. To test this hypothesis, we next evaluated the efficacy of osteoprogenitor-enriched large-MSC fractions against other MSC cell populations and found that, compared to unsorted MSCs or the small-MSC fraction of the same passage (PSG 6), patient donor and dose, irradiated mice infused with the large-MSC fraction showed dramatically improved recovery and survival (FIGS. 2B and 2C). The median survival times were 17 days, >50 days and 13 days for treatment groups given unfractionated MSCs (n=10), large-MSC fraction cells (n=13) and small-MSC fraction cells (n=13), respectively. More than 80% of the irradiated mice infused with the large-MSC fraction survived beyond 50 days and showed rapid recovery of body weight after ~15 days (FIG. 2C). In contrast, infusions of the small-MSC fraction had a negligible impact on the recovery of lethally irradiated mice and there were no survivors in this treatment group beyond day 20. Further escalation of the small-MSC dose to 50×$10^6$ cells/kg did not result in an improvement in survival (data not shown).

Figure 2K:
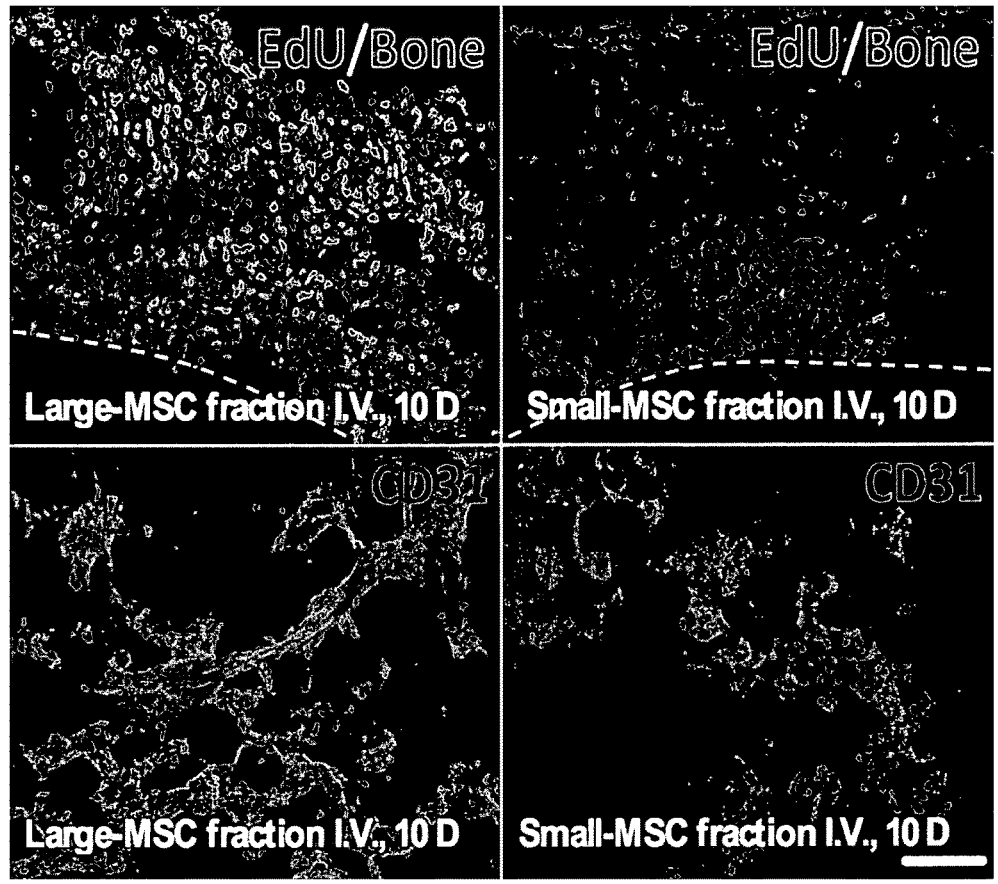
FIG. 2K shows representative histological sections of the BM after 10 days for large- and small-MSC treatment groups. BM from the large-MSC treatment group is highly cellularized and contains more EdU$^+$ cells and CD31$^+$ vessel structures. Dotted lines indicate location of mineral bone and scale bar=100 µm.
Figure 2L:
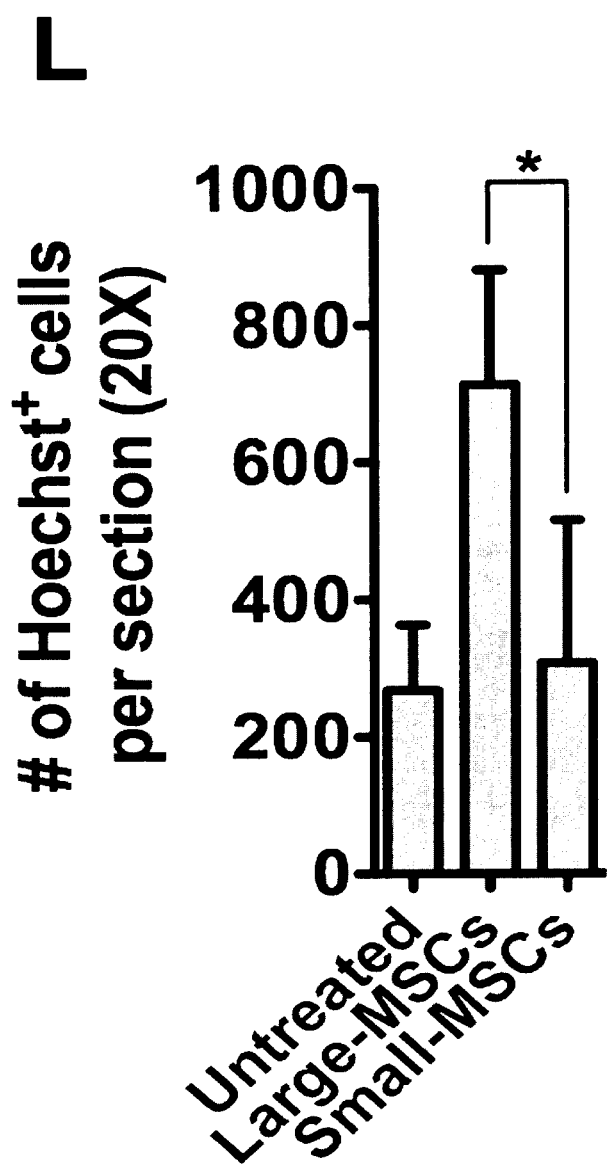
FIG. 2L shows quantification of the degree of BM cellularity from histological sections. *P=0.0378, n=15 sections analyzed from 3 different mice.
Figure 8A:
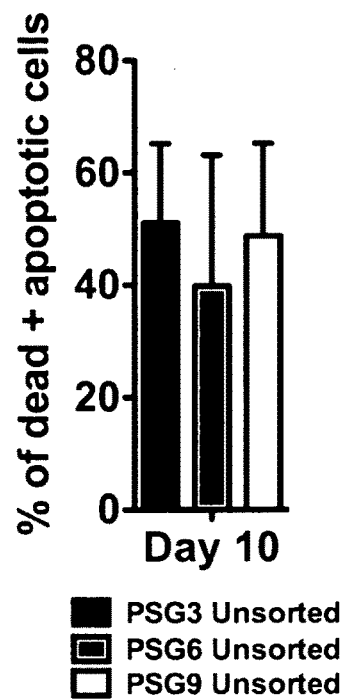
FIG. 8A shows FACS measurement of the number of dead and apoptotic cells in the femoral BMs of a separate set of experimental groups similar to FIG. 2A (n=4 mice per group).
Figure 8B:
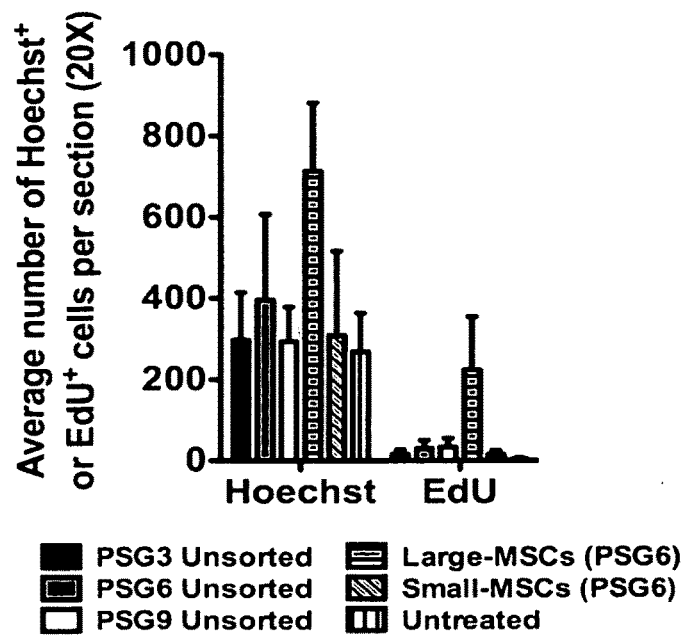
FIG. 8B shows quantification of the cellularity of histological femoral sections taken from experimental groups on day 10. n=15 sections analyzed from 3 different mice.
Figure 8C:
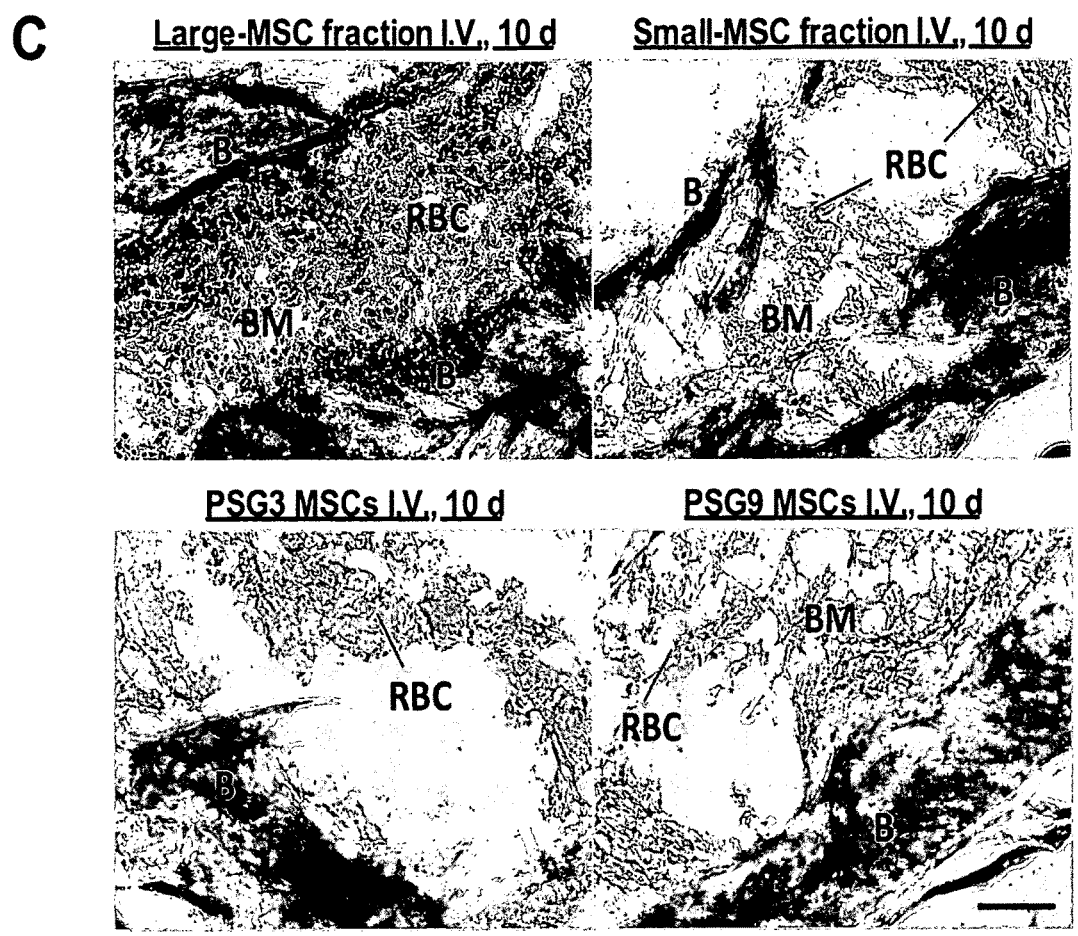
FIG. 8C shows representative H&E stains of femoral BMs sections on day 10. Femurs of large-MSC treated mice were highly cellularized and flushed with RBCs compared to other treatment groups. RBC=red blood cell, BM=bone marrow, B=bone. Scale bars=200 µm. All values are given in mean±sd unless otherwise stated.

Peripheral blood counts for WBCs, RBCs and platelets dropped sharply after myeloablative irradiation. Significant decreases in hematocrit and platelet levels were obvious by day 10 and corroborated with survival and weight loss data, indicating that anemia and thrombocytopenia are likely reasons for death. In the surviving large-MSC treatment group, endogenous hematopoietic recovery was observed after 10 days and peripheral blood counts were restored to original levels after ~30 days (FIGS. 2D to 2F). Irradiation induces significant damage and cell death in the BM and accelerated regeneration of BM tissue with subsequent endogenous hematopoietic reconstitution may be responsible for the improved survival rate in the large-MSC treatment group. Compared to other treatment groups, FACS analysis of cells in the BM of large-MSC treated mice show a much lower rate of cell death (FIGS. 2G, 2H, and 9A) and a higher rate of cell proliferation (FIGS. 2I to 2J) over a 10 day period. Analysis of BM tissue sections obtained from these experiments further confirms a degree of cellularity and EdU staining that was significantly higher after administration of large- vs other MSC or untreated groups. Representative histological sections and analyses are shown in FIGS. 2K and 2L, as well as in FIGS. 8B and 8C.

Figure 2M:
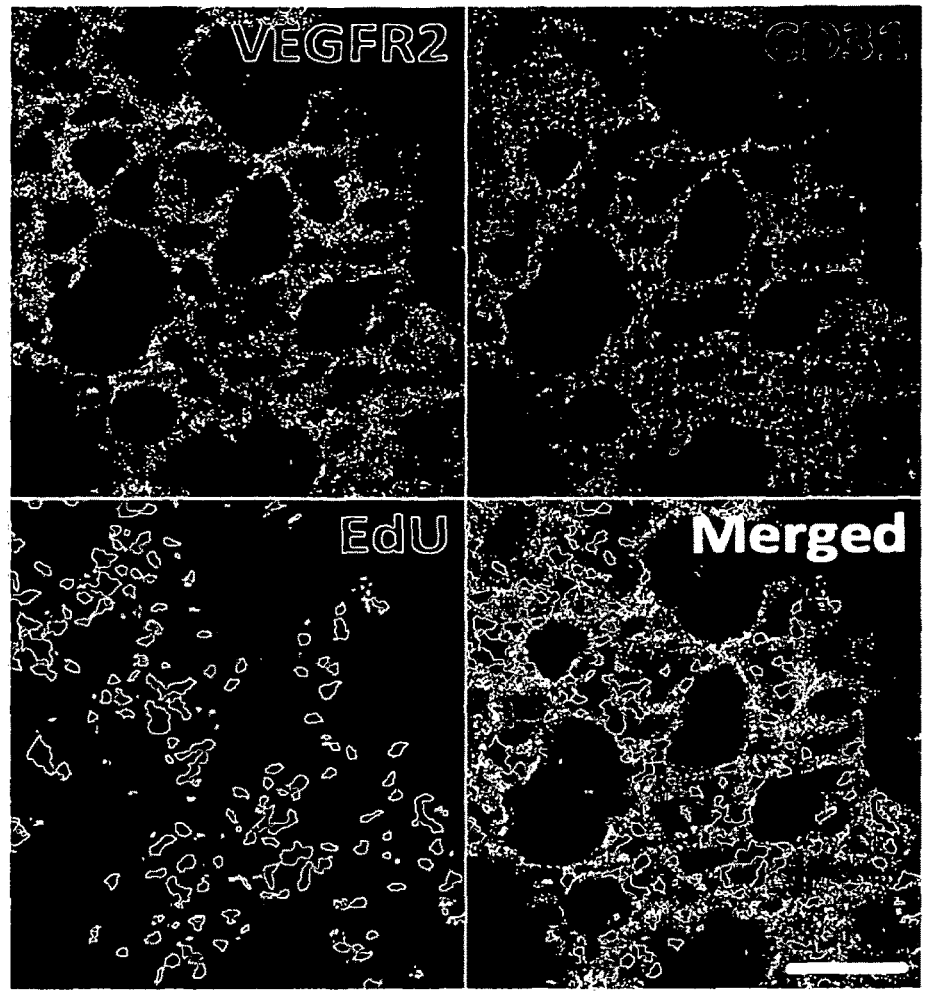
Figure 2N:
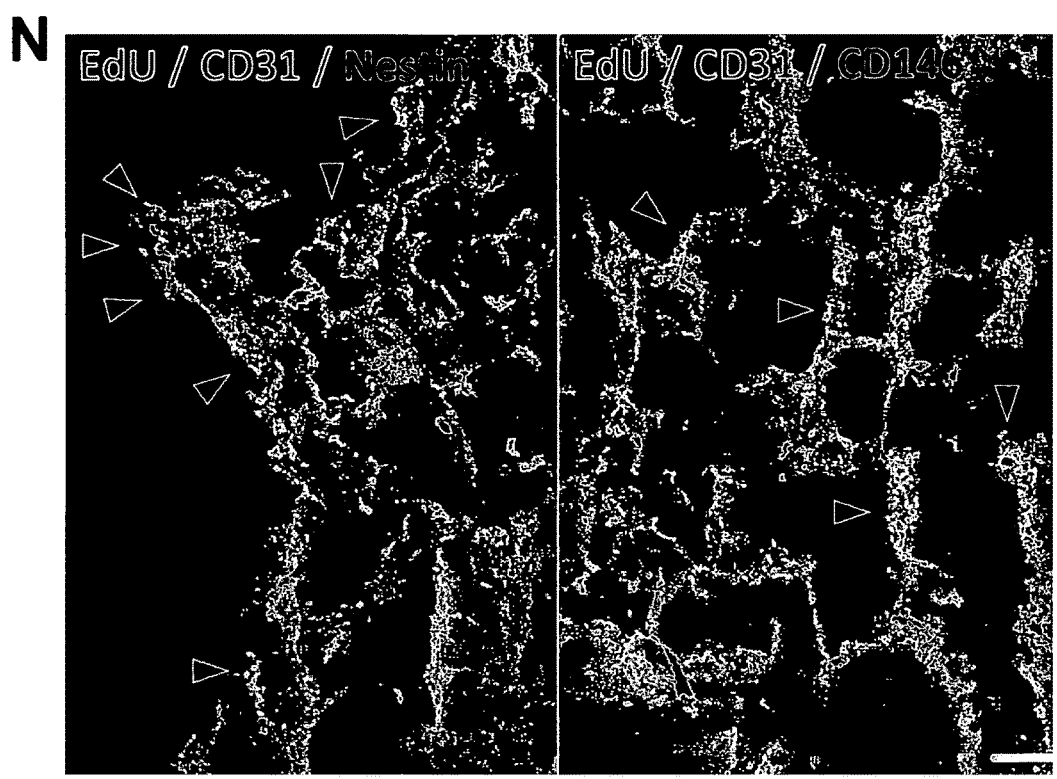

The majority of EdU$^+$ cells were found located in the space spanning across the BM, and not lining the cortical bone (FIG. 2K), indicating that tissue damage and regeneration is confined to the BM vascular and extravascular compartments. When left untreated, the BM vasculature becomes highly regressed as a result of irradiation damage (data not shown), but the administration of large-MSCs led to the greatest extent of vascularization of the BM space by day 10 (FIG. 2K). Further examination showed co-localization of EdU with VEGFR2$^+$/CD31$^+$ endothelial cells of the vasculature (FIG. 2M) as well as nestin$^+$ and CD146$^+$ stromal cells in the perivascular space (FIG. 2N), corresponding to regeneration of the HSC vascular and perivascular niches, respectively. Together, these results demonstrate the potency of large-MSCs for regeneration of BM tissue, including the vasculature and important stem cell niche environments after injury inflicted by irradiation.

MSCs from Both Fractions do not Significantly Engraft within the BM

Figures 3A, 3B:
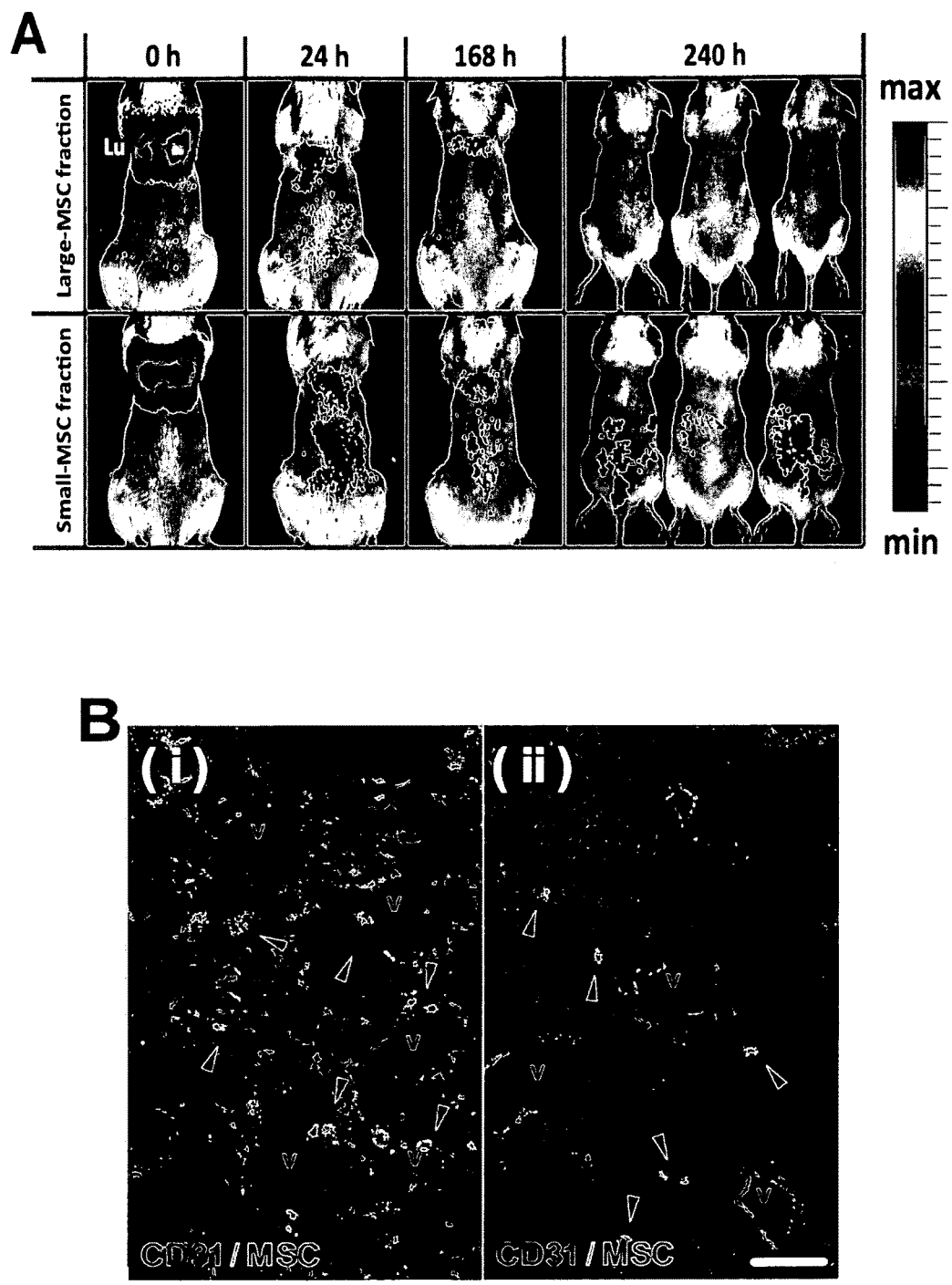
FIGS. 3A-3J show that large-MSCs are efficient "cell-factories" that mediate tissue repair via secreted factors.
Figure 3C:
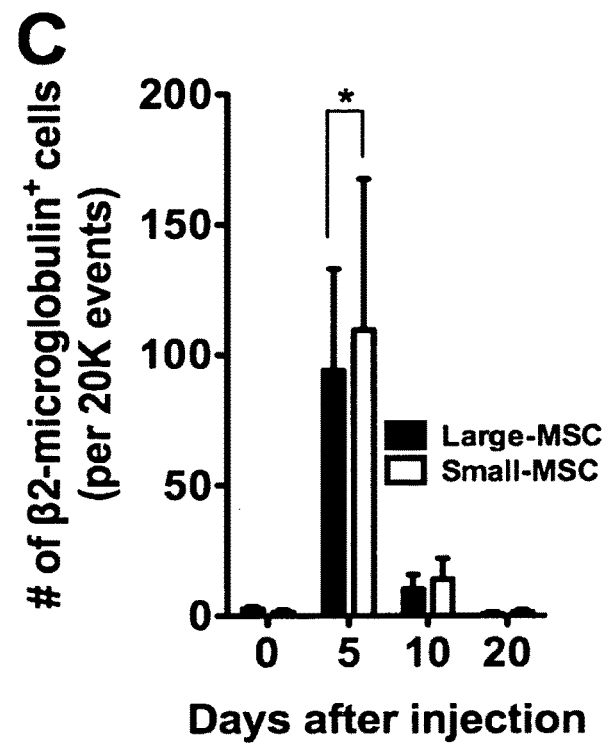
Figure 9A:
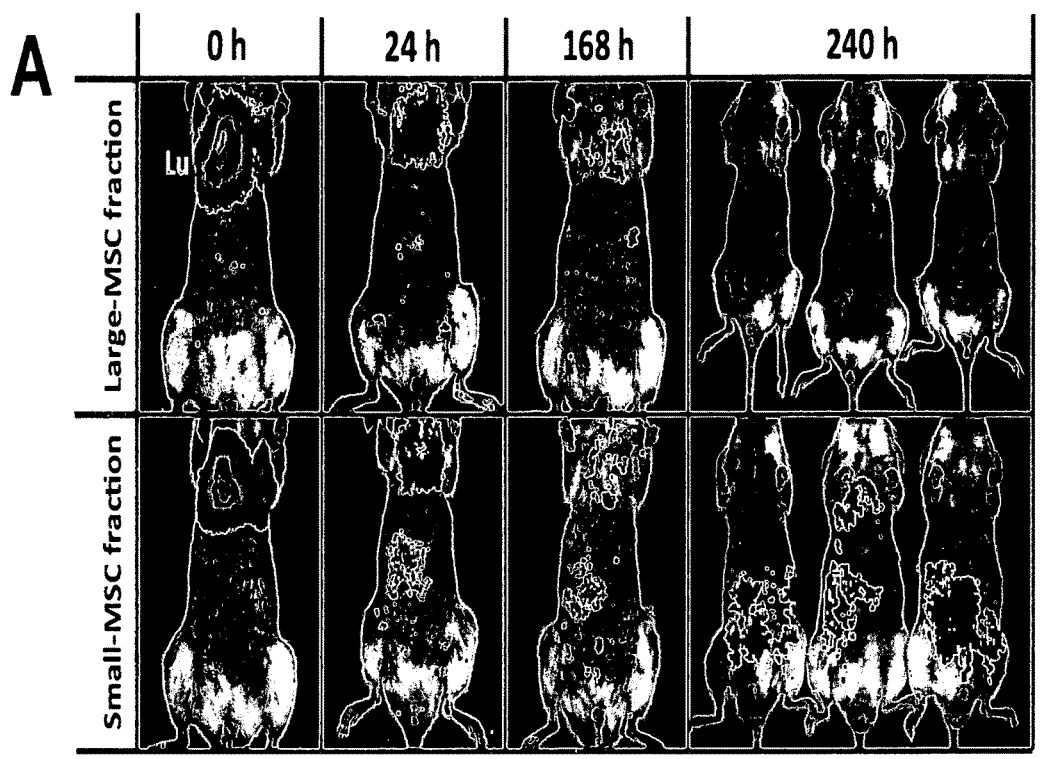
FIG. 9A is a ventral view of biodistribution of luciferase-transformed MSCs from both large- and small-MSC fractions. The MSCs were injected via the tail vein into sublethally irradiated NOD/SCIDs (3.0 Gy). Dorsal view is shown in FIG. 3A.
Figure 9B:
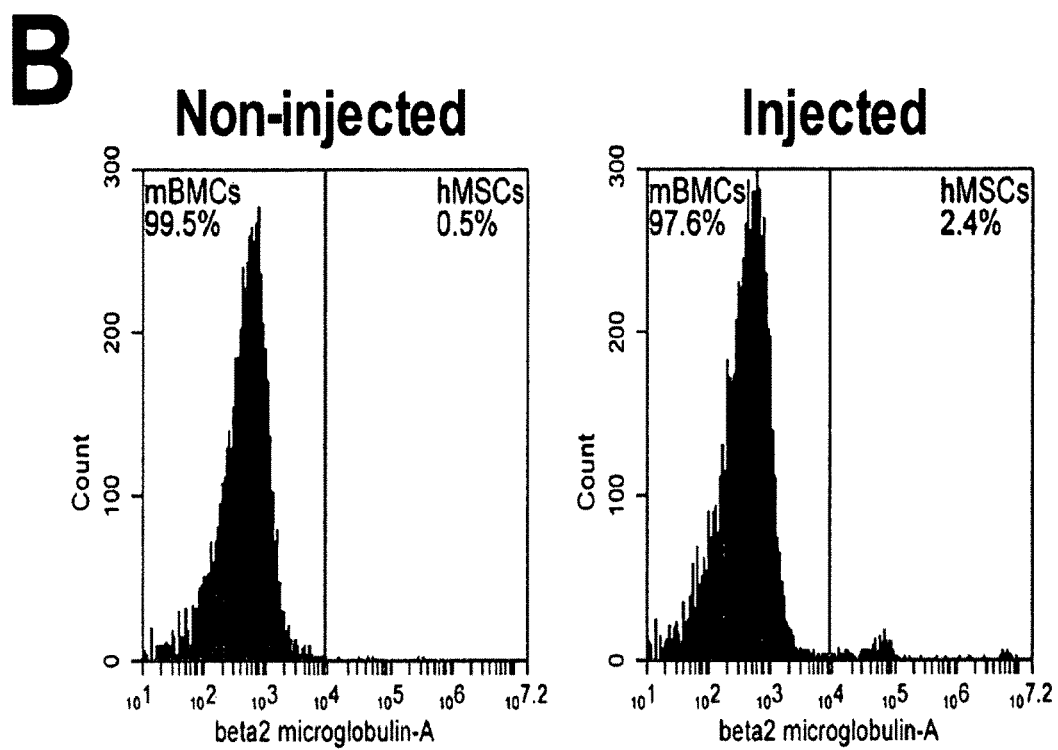
FIG. 9B shows representative FACS histograms of the femoral bone marrow aspirate showing low injected MSC presence (<~5% of analyzed cells). The injected human MSCs are detected via human specific staining for (β2-microglobulin.
Figure 9C:
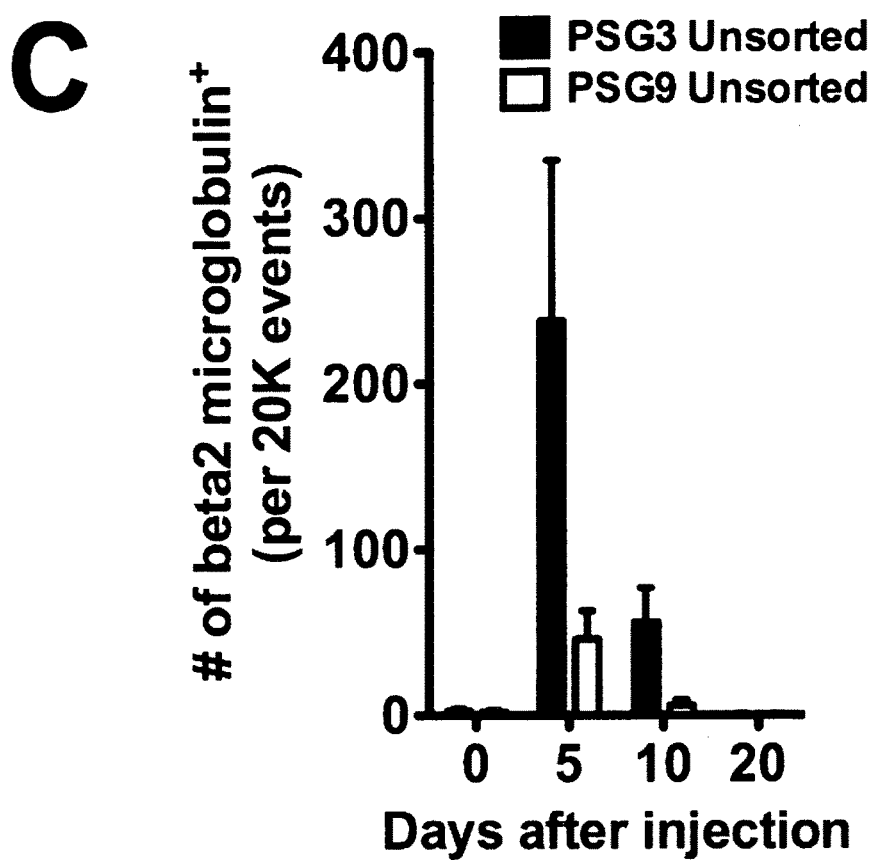
FIG. 9C shows FACS analysis of the BM for injected human MSC presence after PSG 3 and PSG 9 MSCs were injected (n=3 mice). MSCs were detected with human specific β2-microglobulin. All values are given in mean±sd unless otherwise stated.

To understand our observations, we first examined the biodistribution of MSCs via bioluminescence imaging of injected luciferase-transformed MSCs in order to determine if MSC engraftment within injured BMs played any therapeutic role. No changes were found in the immunohistochemistry or tri-lineage differentiation capability of MSCs after transformation (data not shown), and the bioluminescent signal was constitutively and equally expressed in both MSC fractions (data not shown). In vivo bioluminescence analysis of transformed MSCs shows a near-linear relationship between MSC number and bioluminescent signal, with a lower detection limit of $10^2$-$10^3$ cells after subcutaneous injection (data not shown). In order to observe long-term biodistribution of injected MSCs and also to provide BM injury stimulus for MSC homing, a sublethally irradiated mouse model (3.0 Gy) was used in these experiments, which demonstrated survival rates above 95% for up to 30 days even without treatment. Immediately after tail vein injection into sublethally irradiated mice, MSCs of both fractions accumulated in the pulmonary capillary beds, where they underwent a gradual redistribution to the rest of the body within 24 h (FIGS. 3A and 9A). Over this period of distribution, the MSC bioluminescent signal did not localize specifically to any organ or body part and longer-term imaging showed no distinct differences in the overall biodistribution patterns of both MSC fractions. All bioluminescent signals were lost from mice by day 10-15. We additionally evaluated histological sections of the lung tissue 24 h after MSC injection to determine if MSCs engrafted within the lung after tail vein injection. Human specific staining for β2-microglobulin in these lung sections show that the majority of the MSCs were found within vessel lumens, but a small amount were extravasated in the lung tissue (FIG. 3B). No MSCs were found in the lungs after 2 weeks, corroborating with bioluminescent tracking observations. FACS examination of whole BM aspirates further shows that regardless of MSC passage or sorted fraction, only a small number of human MSCs, typically between 0.02 to 0.2% of the injected dose and less than 5% of total BM cells analyzed, home to the BM by day 5, and they are further diminished in the BM after day 10. (FIGS. 3C, 9B, and 9C). Longer-term studies of the lungs, liver, BM and spleen 30 days after injection showed less than 0.001% of injected human MSCs remaining in the host tissue. Therefore, the short residence times and low levels of accumulation indicate that human MSC engraftment and direct involvement in the processes of regeneration inside the BM are unlikely scenarios to account for our previous observations; these observations are in agreement with other studies documenting the therapeutic mechanisms of MSCs in other injury models.

Figure 3D:
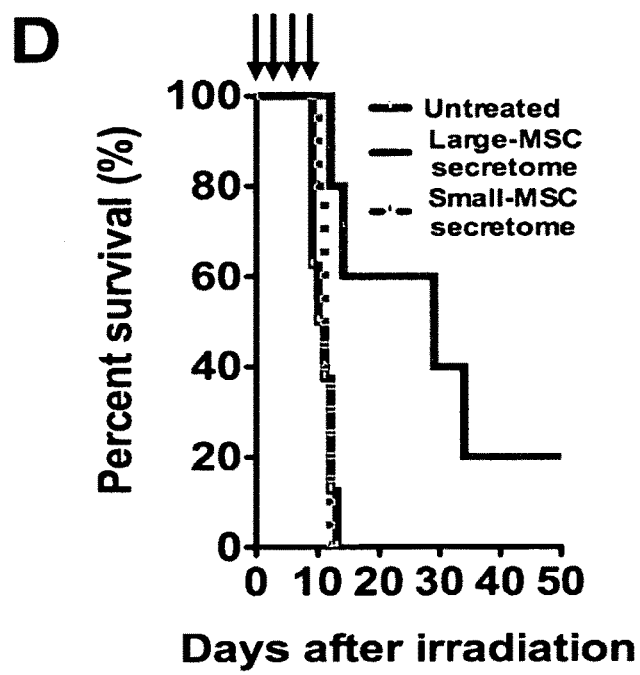
Figure 3E:
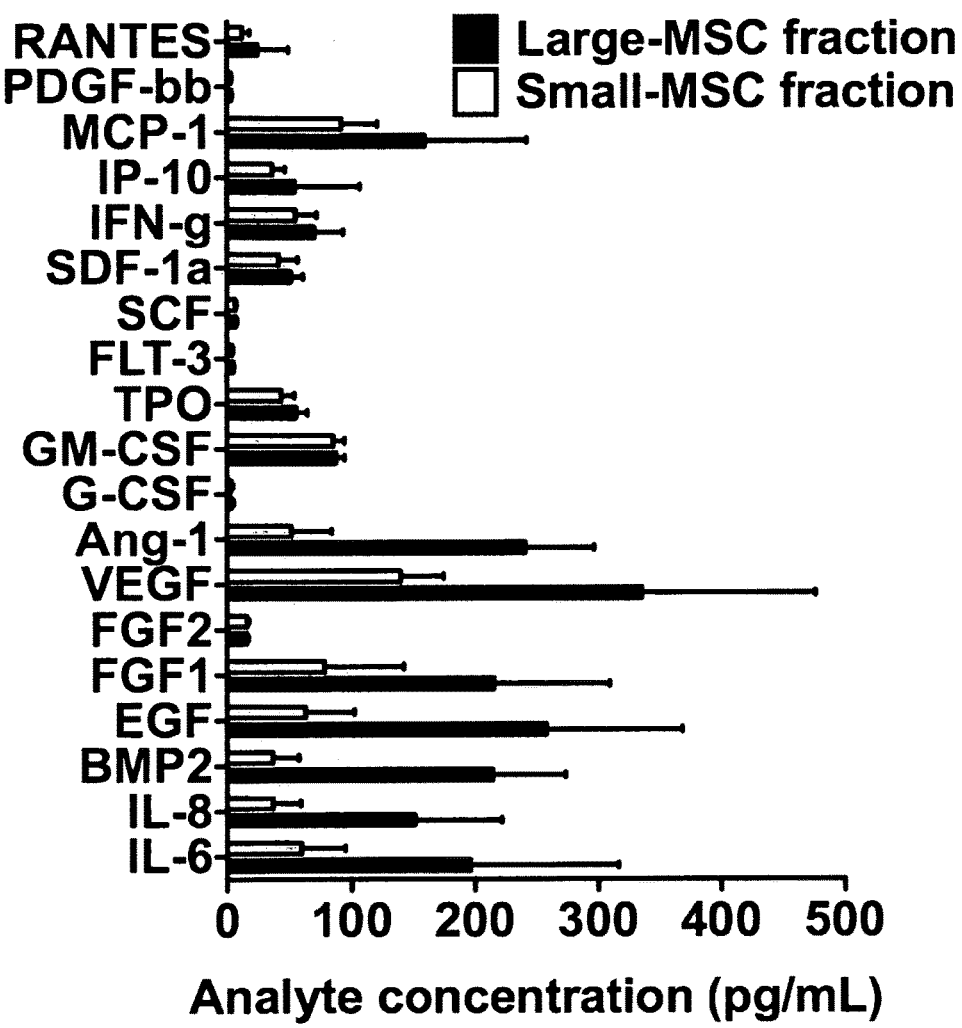
Figure 10A:
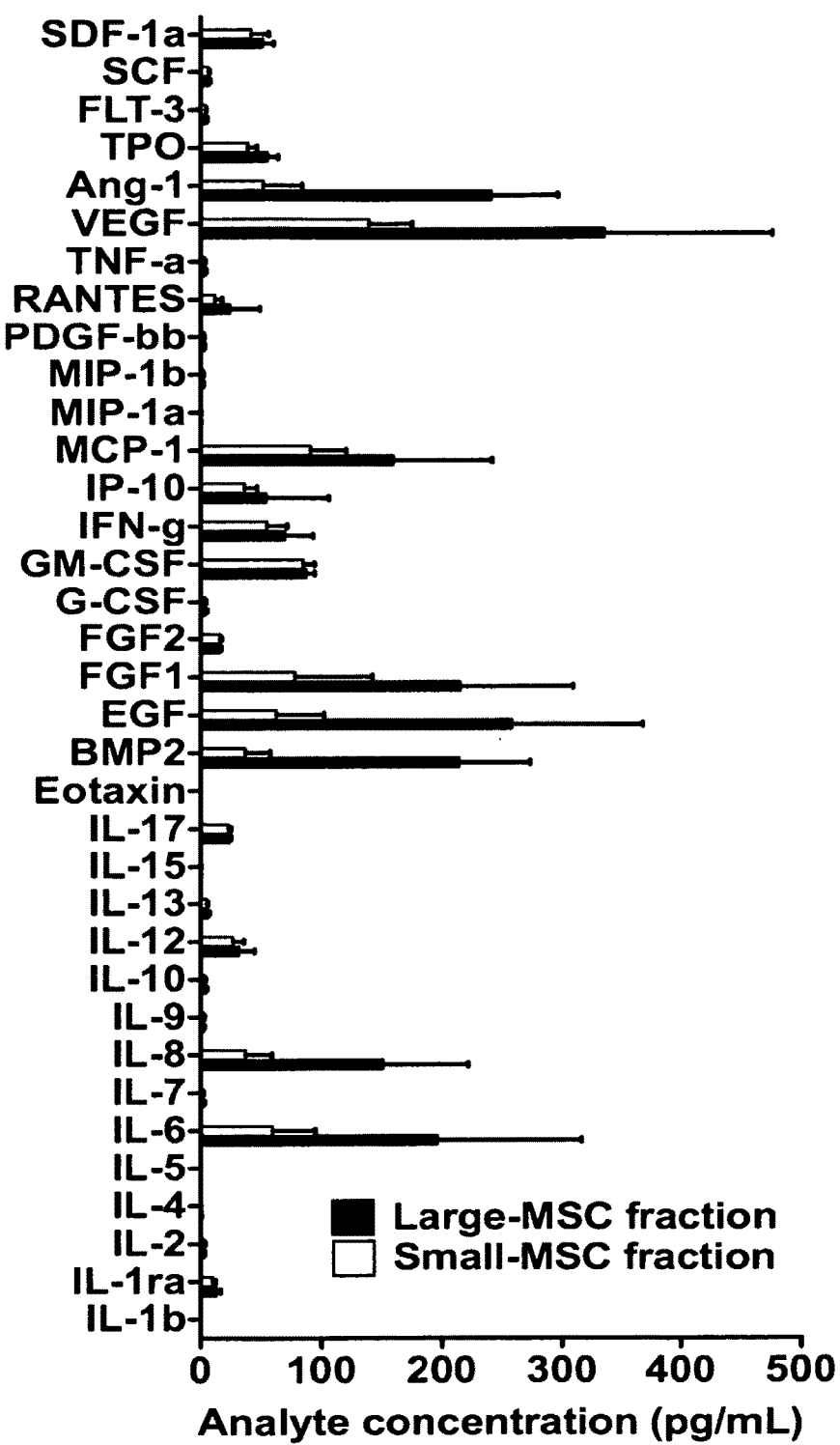
FIGS. 10A and 10B show some of the contents of secretomes of MSCs from the large- and small-MSC fractions, as well as for MSCs at PSG 3, 6 and 9, respectively.
Figure 10B:
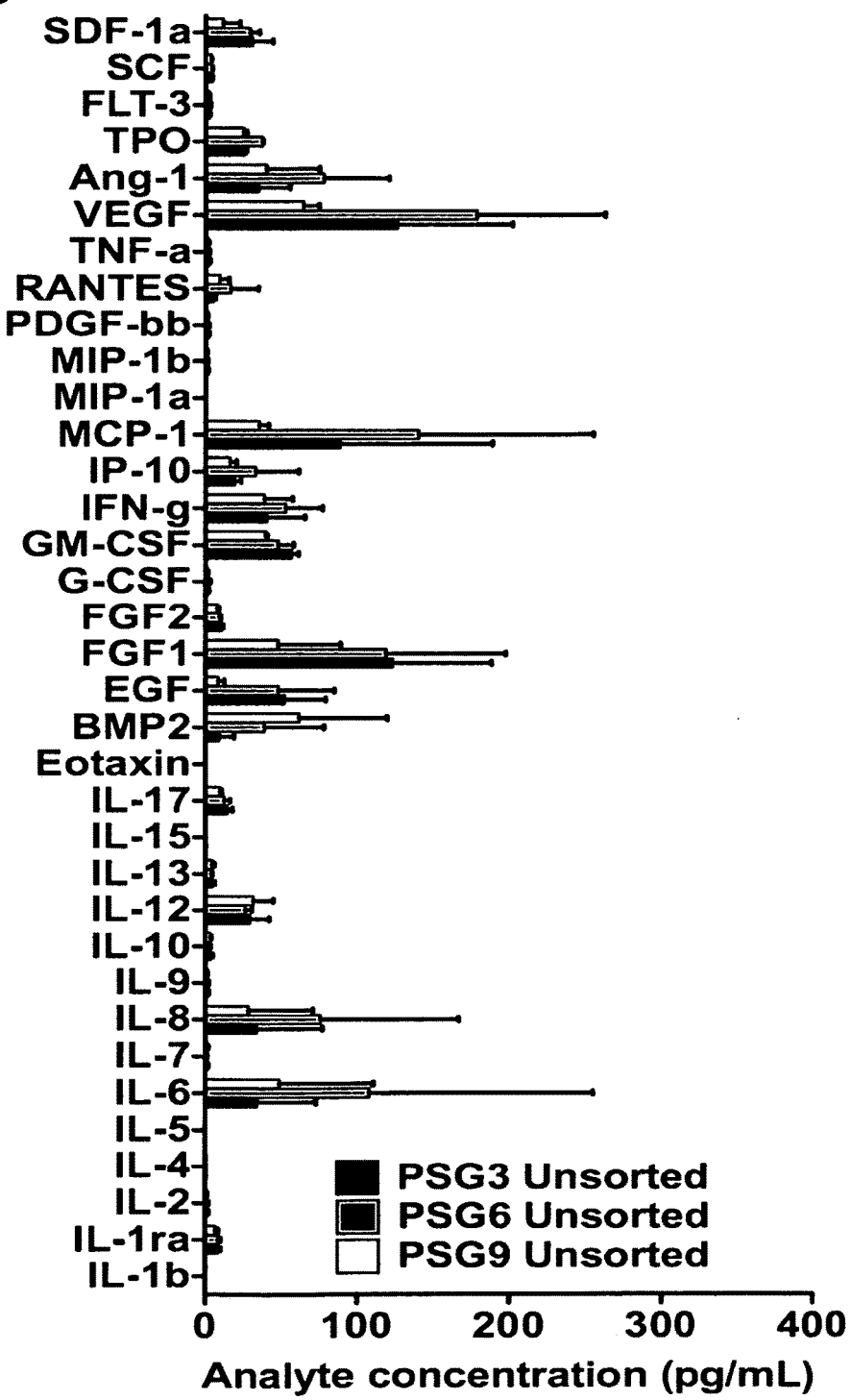
Figure 10C:
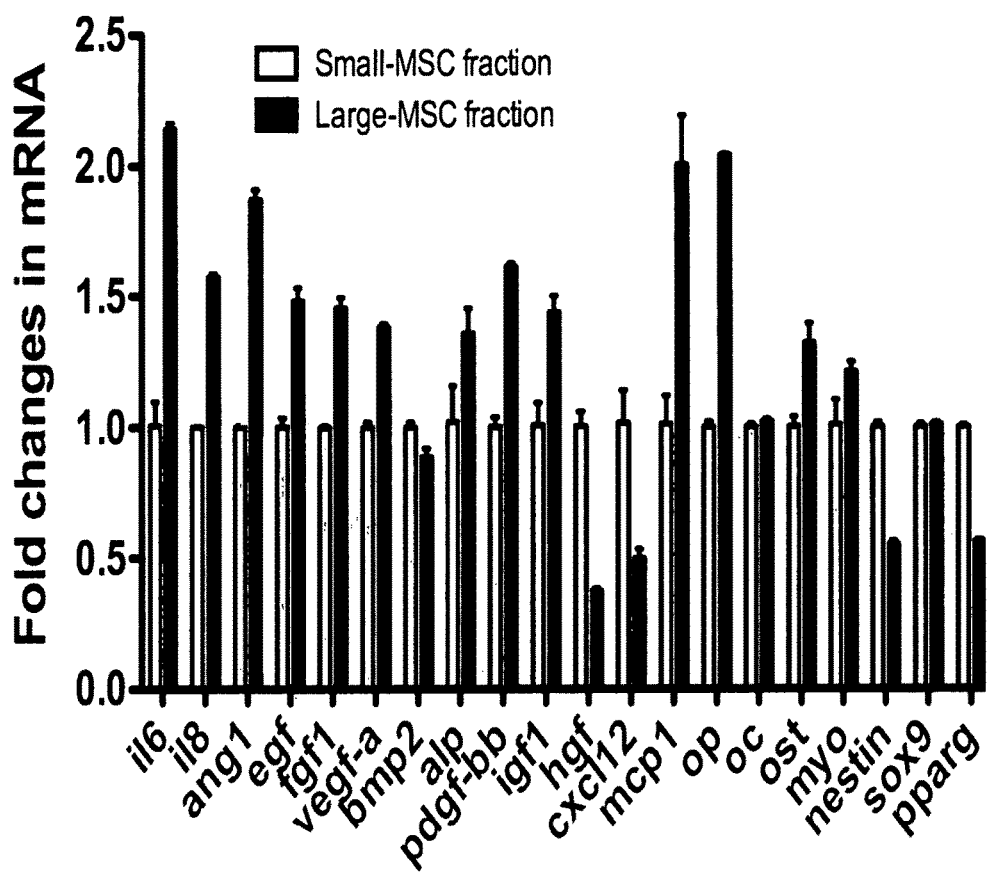
FIG. 10C shows representative RTPCR analysis of the transcripts for secreted proteins tested to be different between the large- and small-MSC fractions. A strong correlation between transcript and protein expression was found. Secretome samples from 3 MSC donors were tested in triplicates. All values are given in mean±sd unless otherwise stated.
Figure 11:
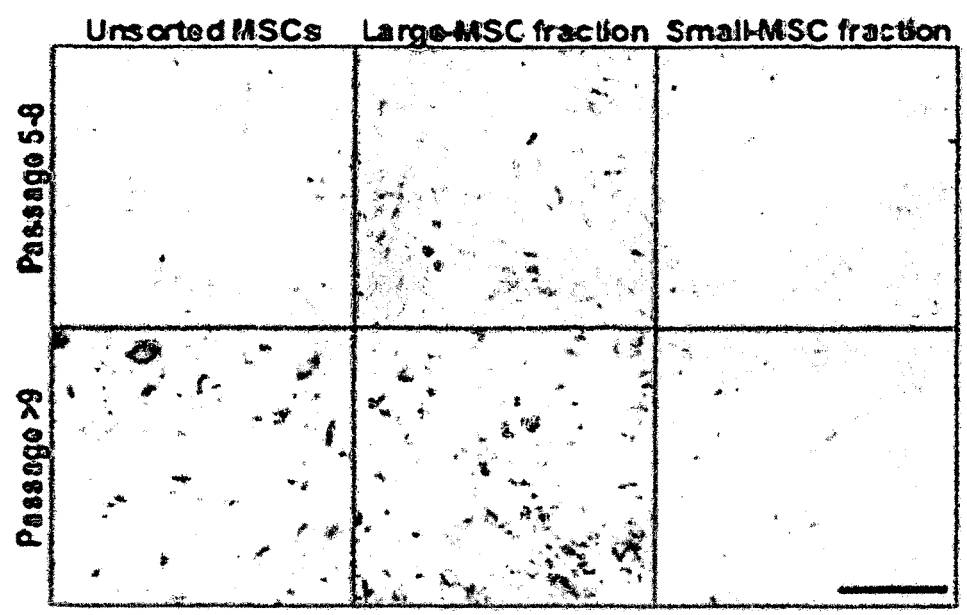
In FIG. 11, beta gal staining for MSCs shows that the cells in the large-MSC fraction approach senescence faster (by PSG 8-9) than the small-MSC fraction.

Large-MSCs Function More Potently as "Cellular Factories" Than Small-MSCs to Mediate Tissue Repair An increasing amount of experimental evidence indicates that MSC-derived regenerative effects are mediated primarily via secreted factors. See Keating, A. Mesenchymal stromal cells: new directions. *Cell Stem Cell* 10, 709-716 (2012); Ranganath, S. H., Levy, O., Inamdar, M. S. & Karp, J. M. Harnessing the mesenchymal stem cell secretome for the treatment of cardiovascular disease. *Cell Stem Cell* 10, 244-258 (2012). It was therefore examined if the efficacies observed with whole cell infusions could be reproduced with secreted factors from MSCs. An identical quantity of the MSCs ($25 \times 10^6$ cells/Kg) that is typically given in an injected cell dose was used to produce a concentrated secretome in serum-free media, which was administered in four intravenous injections to irradiated mice every 48 h after lethal irradiation. Although injections of concentrated large-MSC secretome did not fully recapitulate the results observed with whole cell injections, they imparted a significant survival benefit compared to untreated mice (FIG. 3D), while the secretome from small-MSCs had a negligible effect on mice survival. The median survival times for the secretome therapy groups are 29 days and 11 days for the large-MSC and small-MSC secretome groups, respectively, compared to the >50 days and 13 days for the large-MSC and small-MSC fraction cell therapies, respectively. We next examined if there are differences in the expression of growth factors and cytokines between the two MSC fractions that can account for our observations. Both transcript and secreted protein levels of regenerative factors such as IL-6, IL-8, VEGF, BMP2, EGF, FGF1 and Ang-1 were found up-regulated in the large- vs small-MSC fraction (FIGS. 3E and 10C). Additional data for other analyzed proteins, as well as comparisons of the secretome for unsorted MSCs at different passages, are shown in FIGS. 10A and 10B. Despite the increased prevalence of large-MSCs in later passages (after PSGs 8/9, FIG. 1D), we found that the quantity of protein secreted in later MSC passages is significantly decreased. MSC senescence sets in after PSGs 8/9 (~20-25 population doublings), which could negatively affect the ability of MSCs to function as "cellular factories" that can produce sustained levels of therapeutic factors (FIG. 11).

Figure 3F:
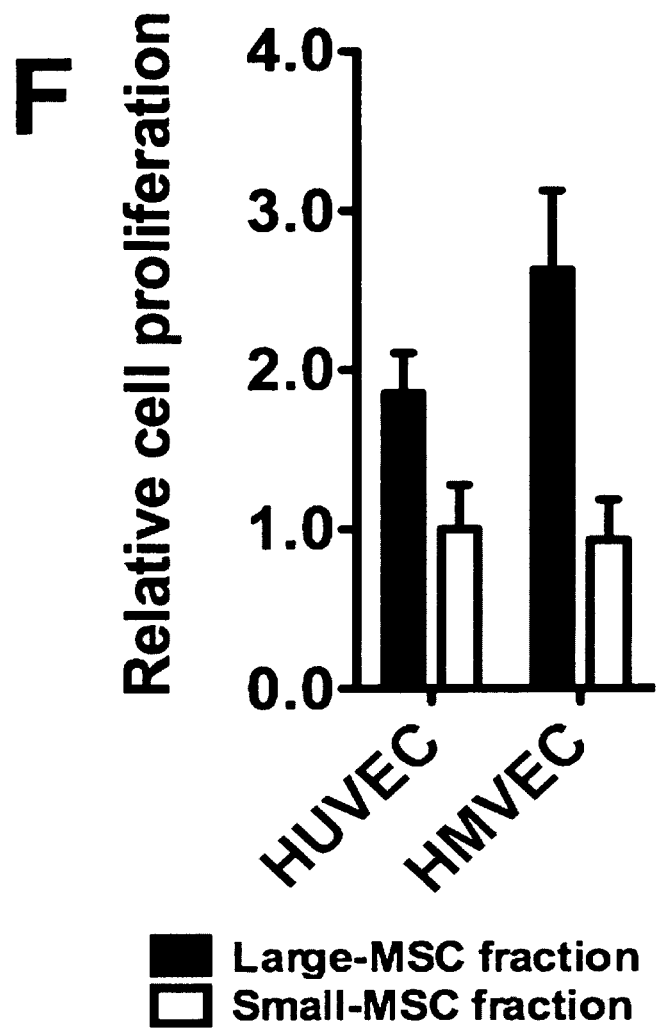
Figure 3G:
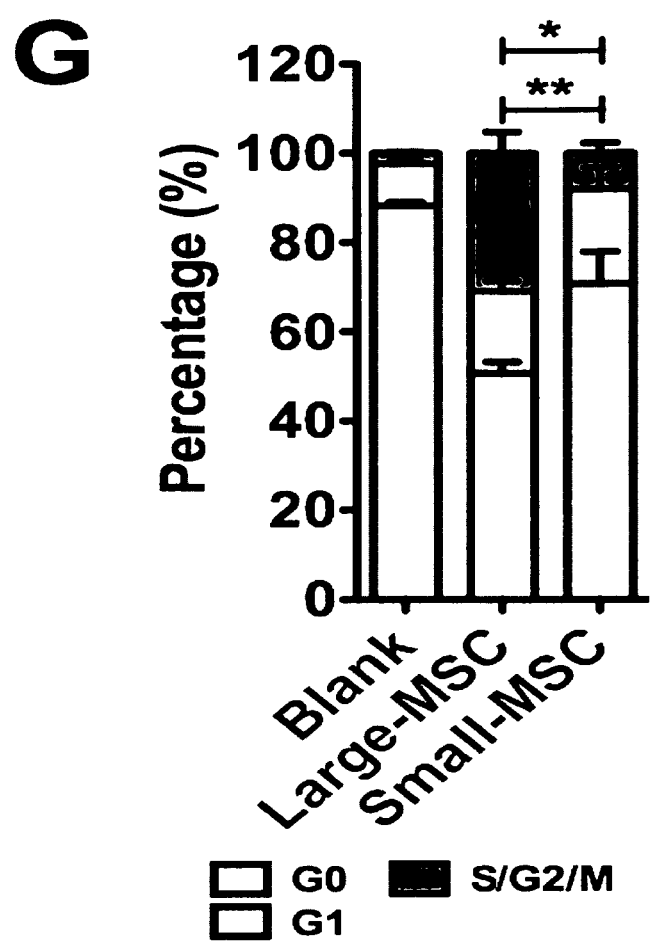
Figure 3H:
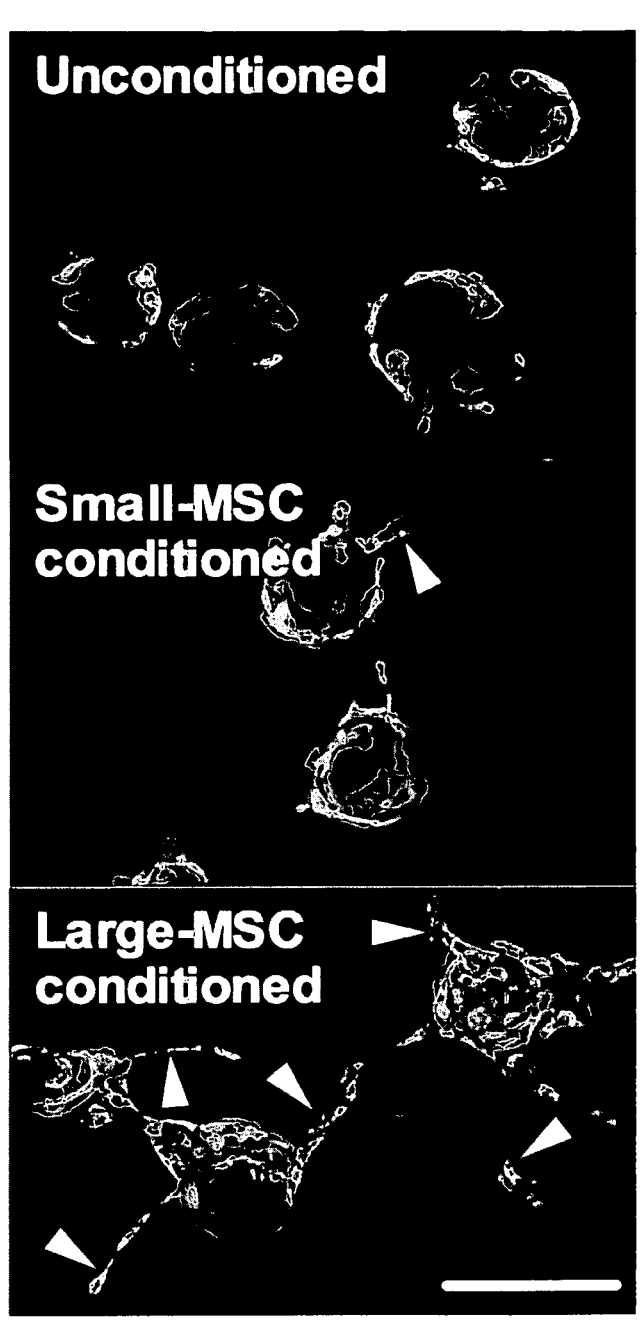
Figure 3I:
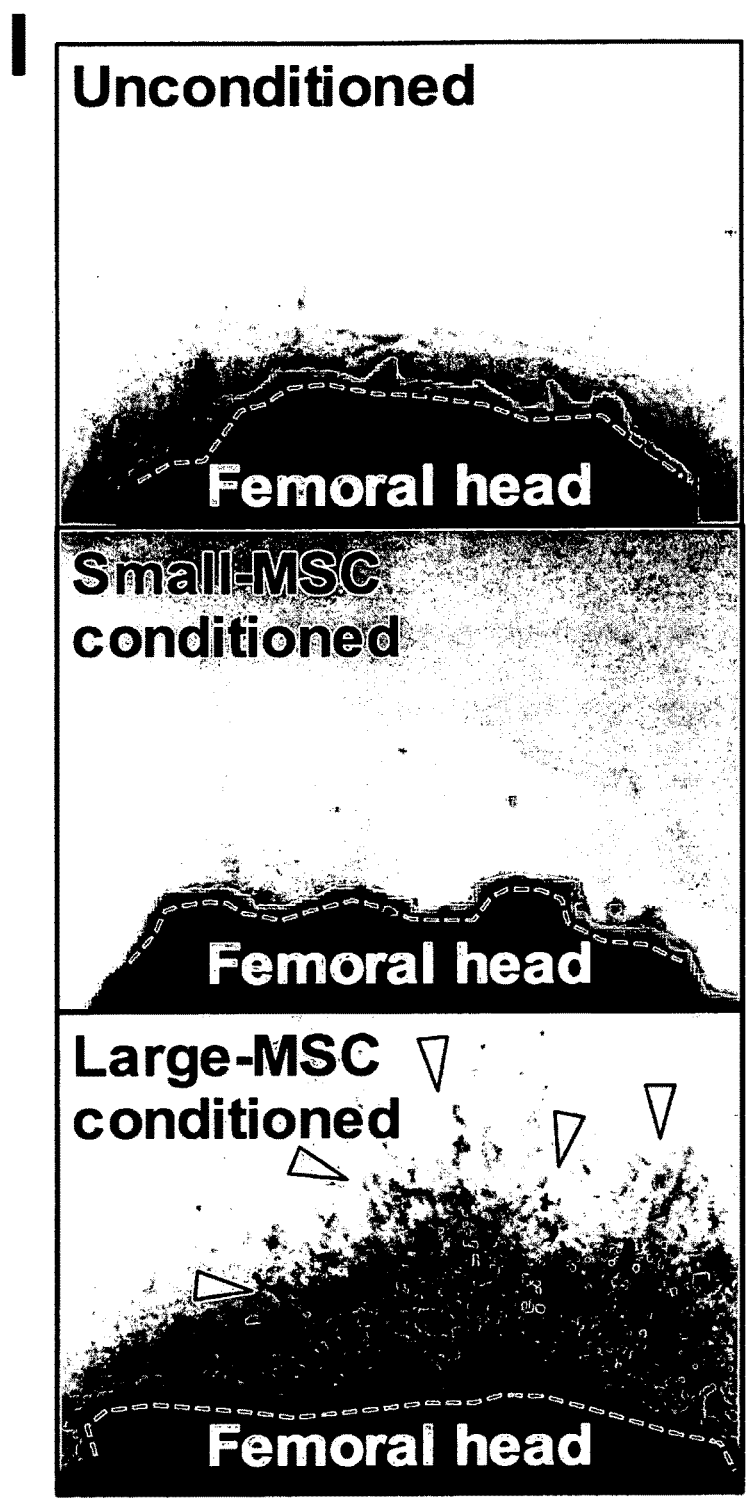
Figure 3J:
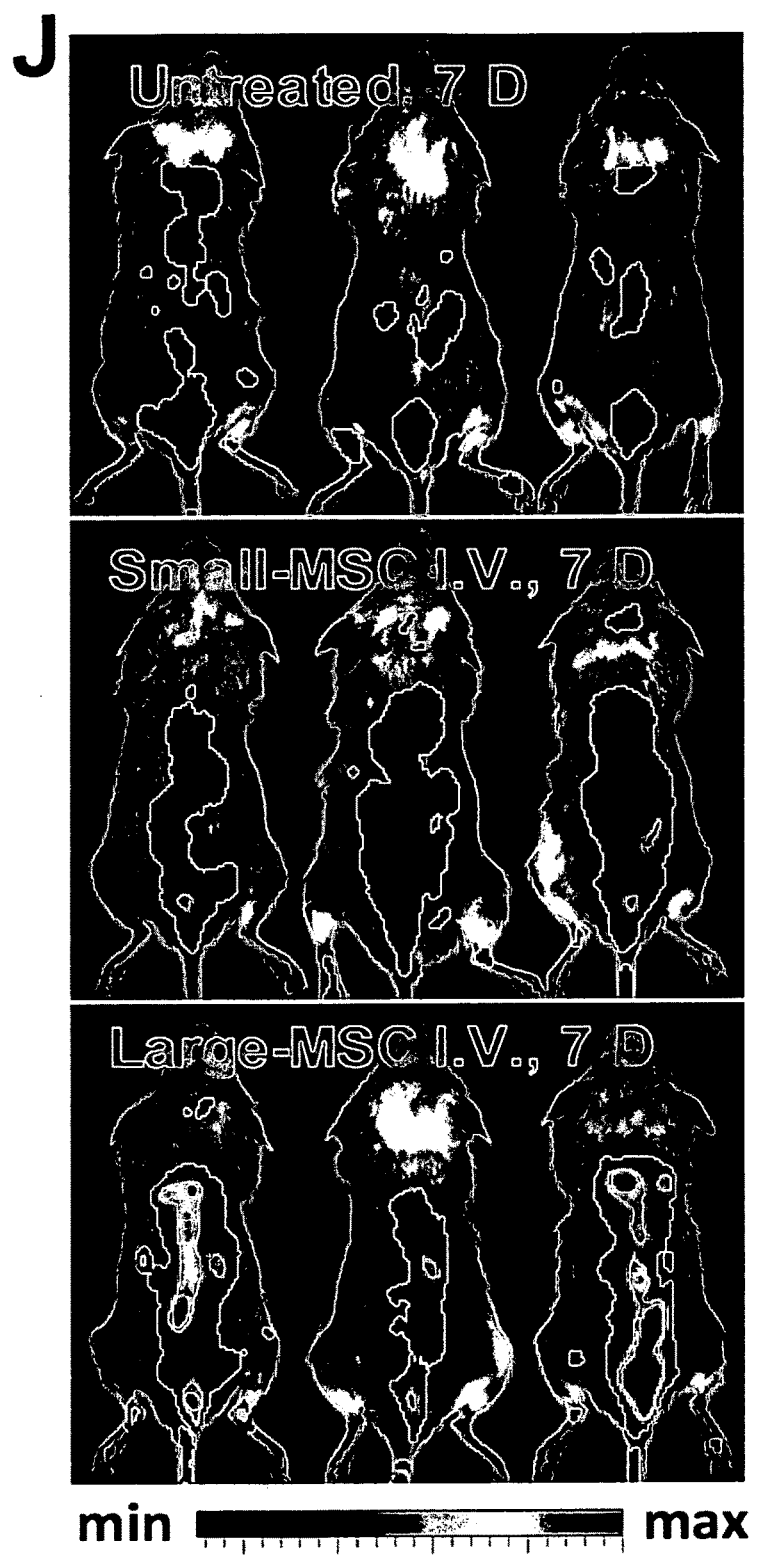

Because the endothelial cell proliferation and angiogenesis were observed in in vivo BM repair (FIGS. 2K to 2M), we sought to investigate the contribution of the different MSC secretome towards these processes. HUVECs and HMVECs cultured in the presence of the large-MSC conditioned media proliferated at higher rates (~1.8× and ~2.5×, respectively, FIG. 3F) to those cultured in media conditioned with small-MSC cells. HUVECs were approximately ~50% in G0, ~% in G1 and ~32% in G2/M 48 h after introduction of the large-MSC secretome, but remained largely in the G0 and G1 phase (>70% and >25%, respectively) with small-MSC and unconditioned media (FIG. 3G). Endothelial sprout formation was also enhanced in the presence of the large-MSC secretome (FIG. 3H), but not in unconditioned media or the small-MSC secretome. Finally, a pro-angiogenic effect was also observed with the use of large-MSC secretome on explanted irradiated (5.0 Gy) femur bone tissue. After 5-10 days of incubation with large-MSC secretome, endothelial sprouts could be seen emerging from the severed ends of explanted femoral head explants, but no significant small vessels were formed in other treatment groups (FIG. 3I). In vivo, the secretome from the large-MSCs also led to the greatest degree of angiogenesis in the BM of lethally irradiated mice, as evidenced by whole body imaging using angiosense, a fluorescent angeiogenic probe (FIG. 3J). Whereas barely detectable levels of the angiogenic probe were found in untreated mice, the spinal column of mice given MSCs showed accumulation of the fluorescent probe, with the highest levels in large-MSC treatment groups.

Increased Donor HSC Homing with Large-MSC Co-Injections

Figure 4A:
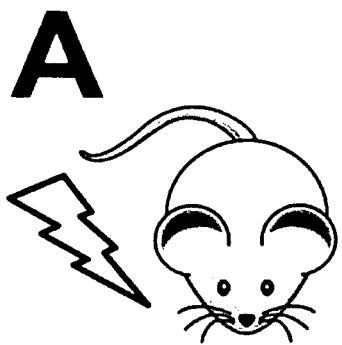
FIGS. 4A-4J show that large-MSCs foster a favorable BM environment for human hematopoietic stem cell (HSC) homing after irradiative (3.0 Gy) myeloablation.
Figure 4B:
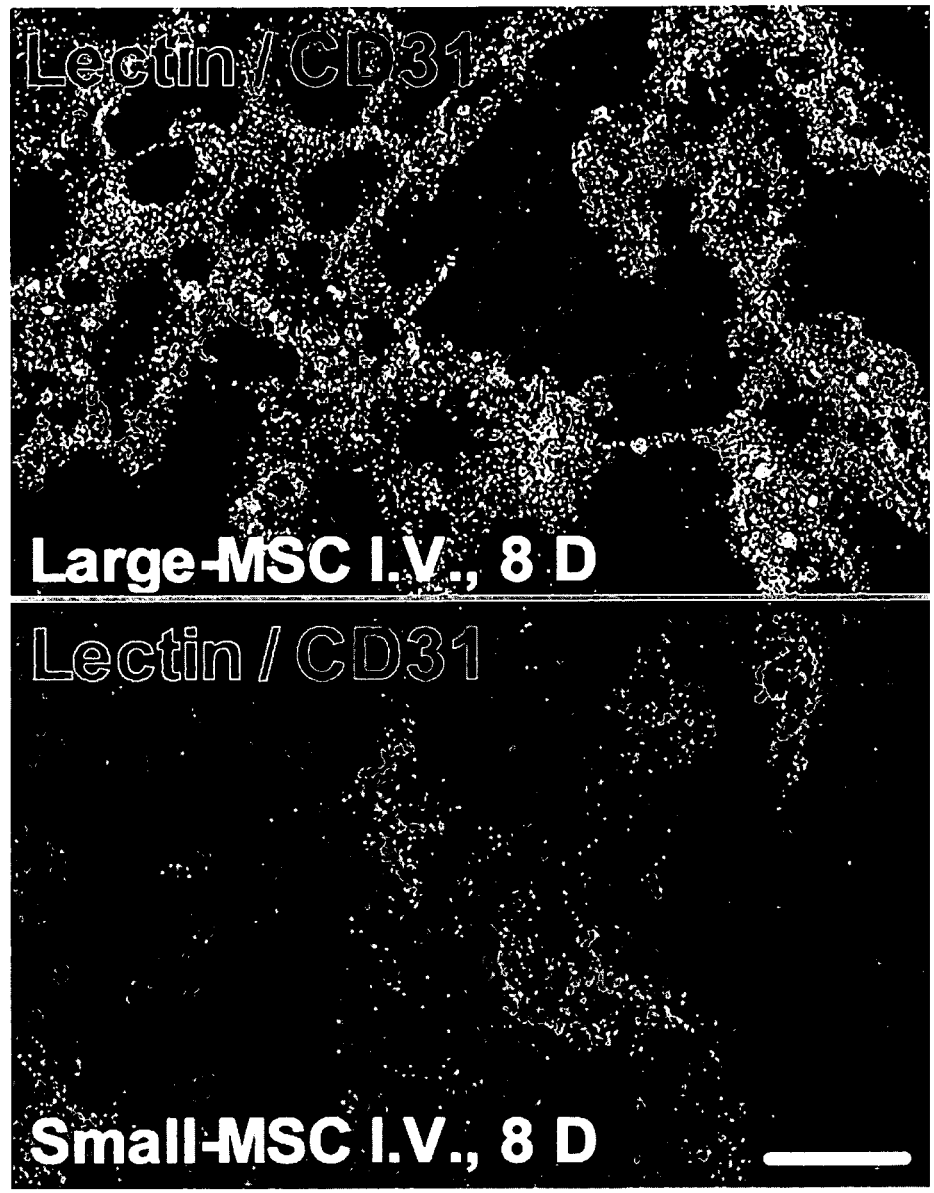
Figure 4C:
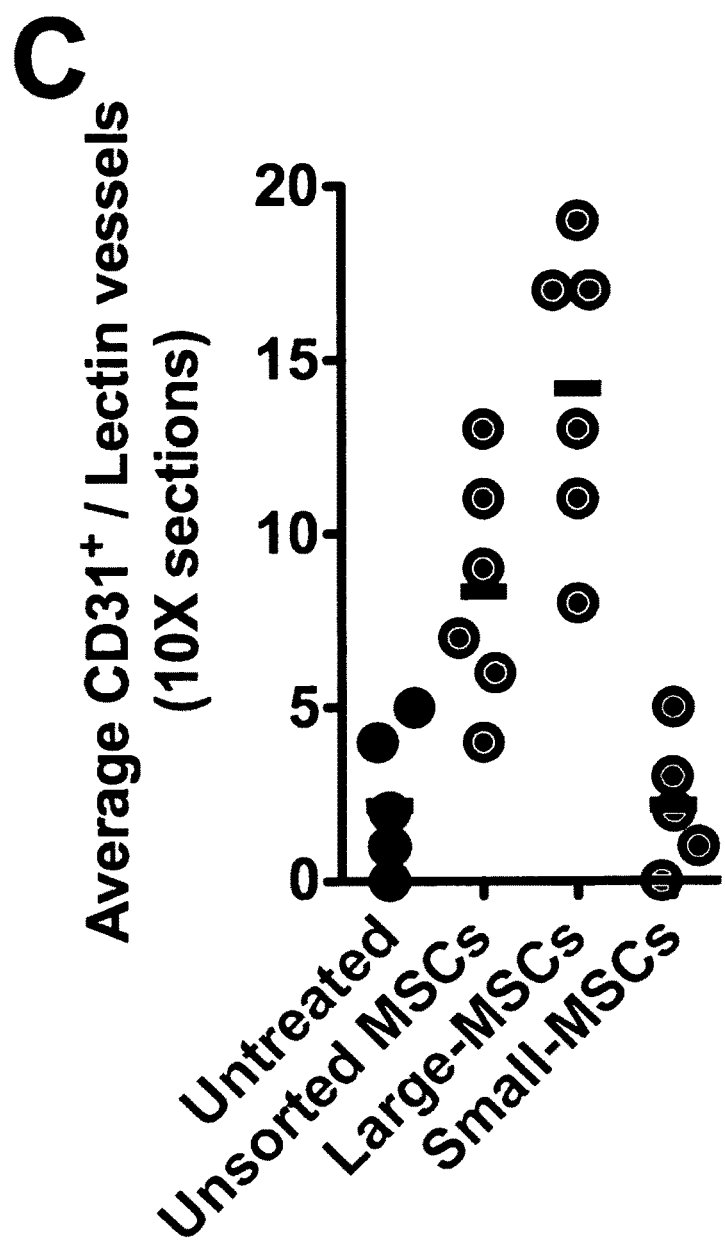
Figure 4D:
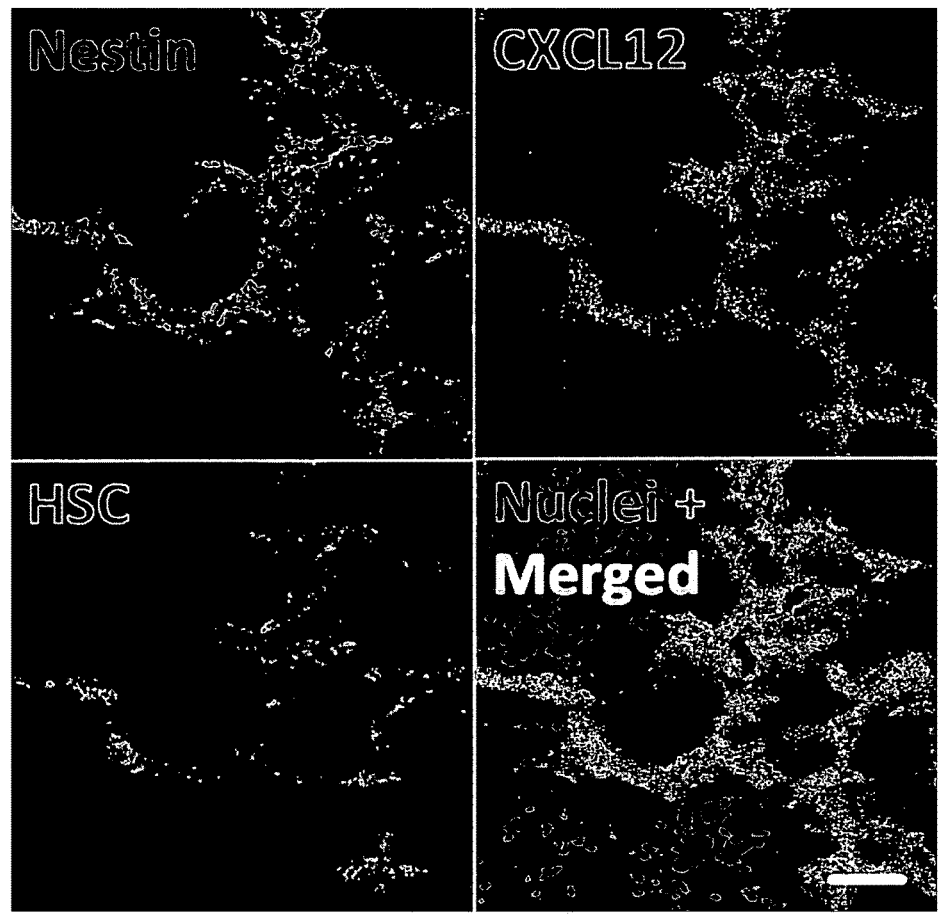
Figure 4E:
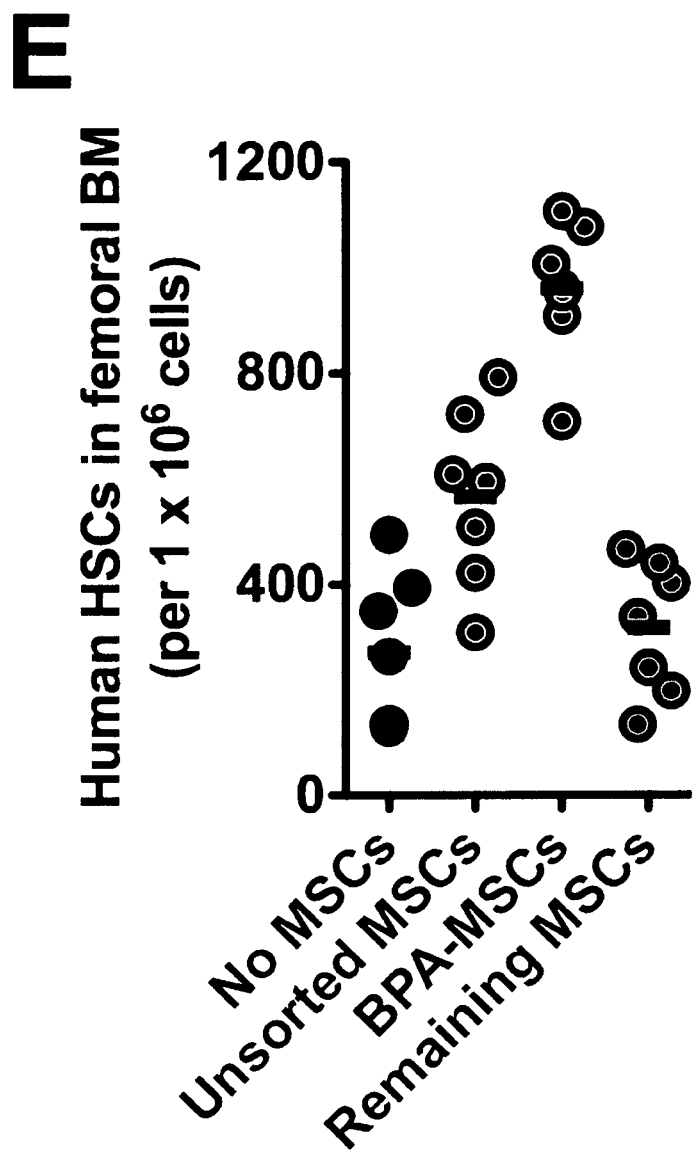

Systemically infused MSCs show potential as therapy for applications in hematopoietic stem cell transplantation (HSCT), as they can promote HSC engraftment and accelerate hematological recovery. To investigate if these effects can be attributed to BM regeneration via injected MSCs, we first examined the ability of donor HSCs to home to the BM after different MSC fractions are used to regenerate the damaged myeloablated BM. The NOD/SCID/gamma (NSG) mouse model was used in these experiments to facilitate long-term examination of a xenograft hematopoietic system. Human $CD34^+$ BM HSCs were culture expanded for a week in the presence of hematopoietic growth factors (SCF, Flt-3 and TPO at 100 ng/mL each) for a week before use. These HSC expansion conditions gave ~4 fold increase in HSC numbers while significantly preserving the number of $CD34^+Lin^-$ HSCs (data not shown). Each expanded HSC product was used in a set of comparative studies with different MSCs and was delivered without further purification as a mixture of stem/progenitor HSCs. 24 h after irradiative myeloablation (3.0 Gy), mice were randomized into different groups (n>4) and given the following MSC injections: 1) unsorted MSCs (PSG 6), 2) large-MSCs (PSG 6) and 3) small-MSCs (PSG 6) at dosages of $20 \times 10^6$ cells/Kg, together with a no-MSC treatment group that was given saline; then, 6 days after MSC treatment, HSCs (100K cells) were administered and allow to distribute in vivo for 24 h before analysis (on day 8) (Treatment 1 in FIG. 4A). FIGS. 4B to 4E show the histological assessment of BM tissue 24 h after HSC injection into the MSC-treated mice. Staining for functional BM vessels with tomato-lectin revealed the highest number of $CD31^+lectin^+$ vessel structures in large-MSC treatment group (FIGS. 4B and 4C), which would facilitate access of injected HSCs to the BM. Histological verification of fluorescently labeled donor HSC homing to the BM was therefore most evident in the large-MSC treatment group, where they were found co-localized with $nestin^+cxcl12^+$ BM cells in luminal vessel structures (FIG. 4D). The degree of donor HSC homing to the BM after the 24 h distribution period in different MSC-fraction conditioned mice was evaluated by FACS analysis. These measurements show a 2-3 fold increase in donor HSC homing to large-MSC conditioned BMs vs other MSC groups (FIG. 4E), indicating the importance of BM tissue conditions for HSC homing.

Figure 4F:
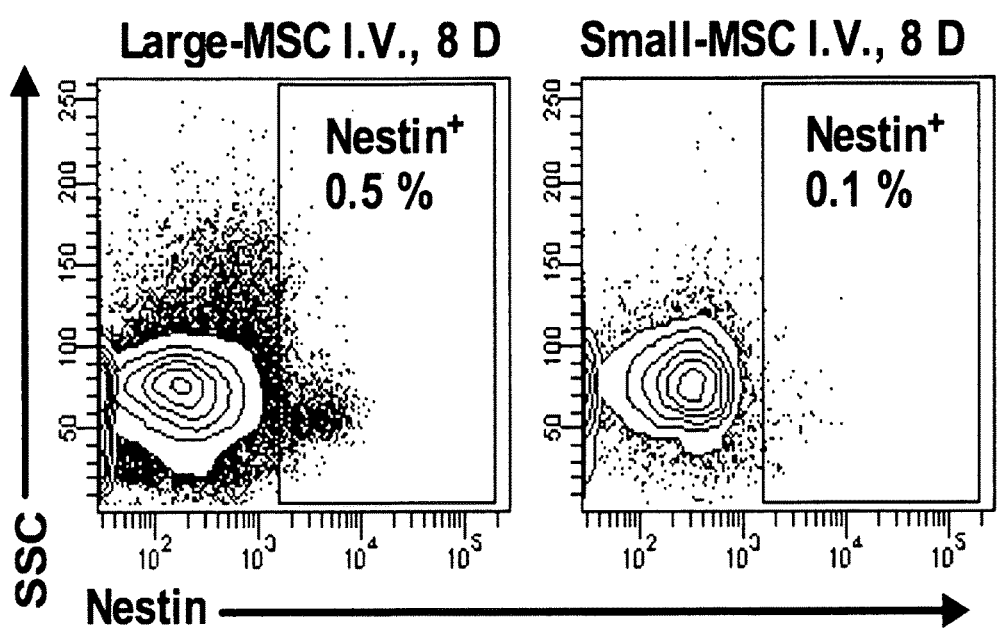
Figure 4G:
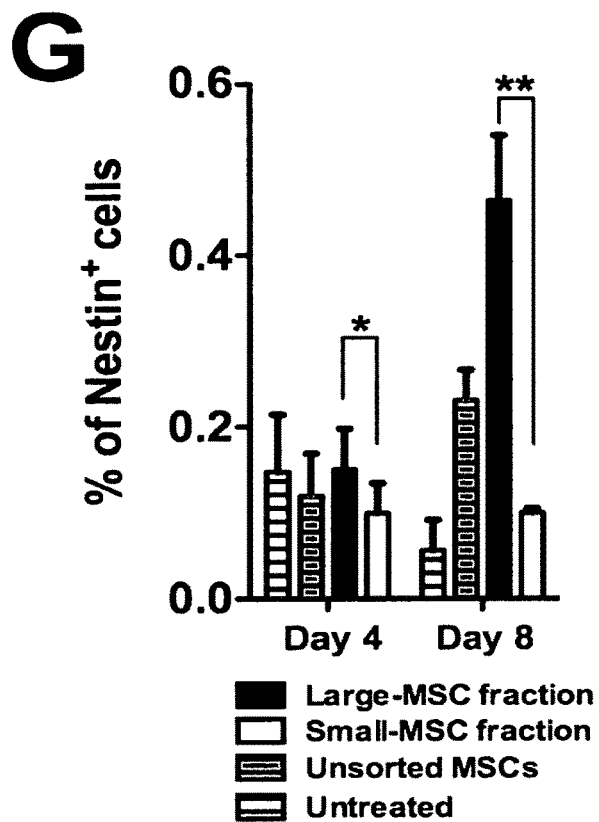

Both cxcl12- and nestin-expressing cells in the BM have been demonstrated in several studies to be critical components of the vascular and perivascular HSC niches that are necessary for HSC homing. Indeed, measurements of the nestin$^+$ stromal cell population in the BM of large-MSC treated mice showed a steady increase between days 4 and 8 (FIGS. 4F and 4G) but not in other treatment groups. Together, these results suggest that efficient regeneration of functional BM vasculature and cellular HSC niche components in the vascular tissue component after myeloablative injury fosters a conducive BM environment for HSC homing and accumulation.

Figure 4H:
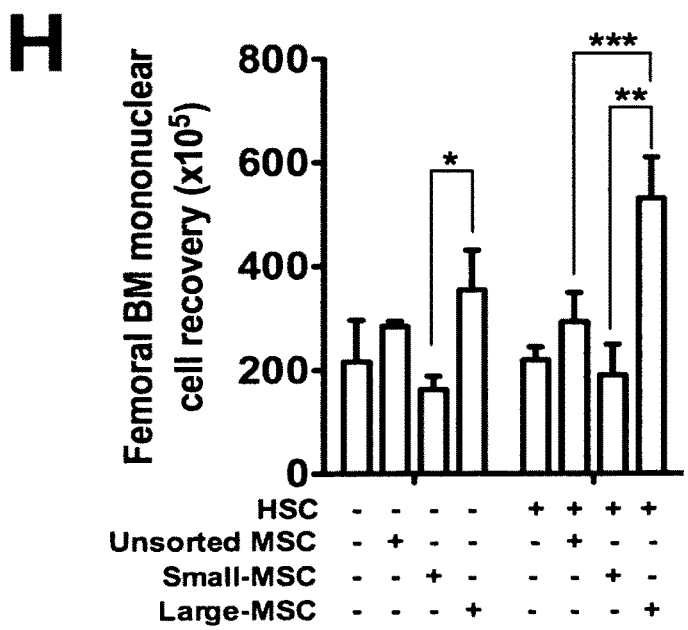
Figure 4I:
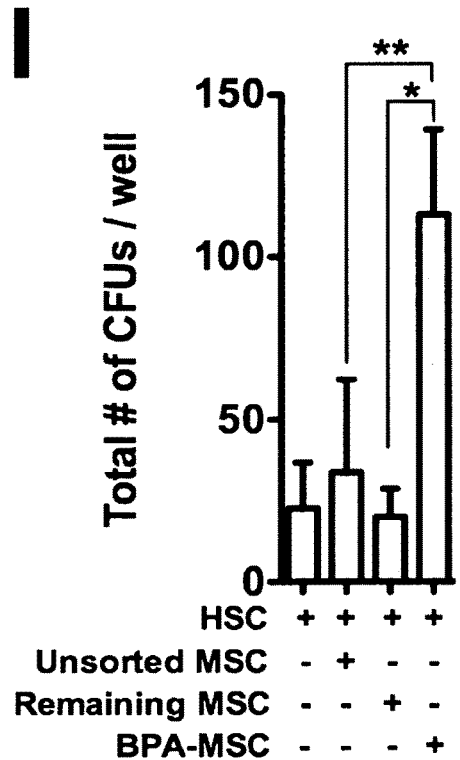
Figure 4J:
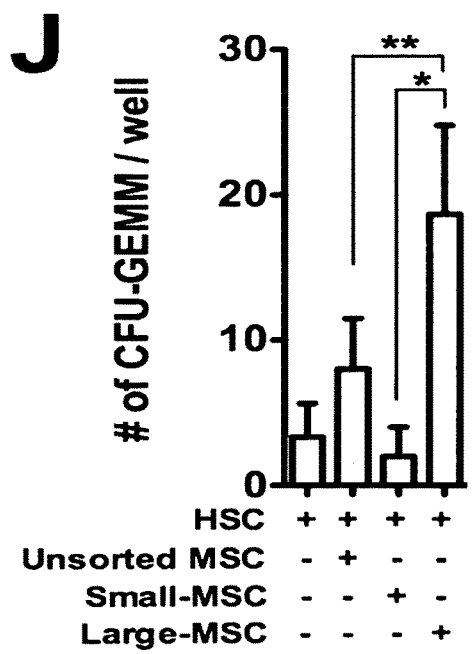

The ability of different MSC-treated BMs to support donor human HSC repopulation potentials (Treatment 2 in FIG. 4A) was investigated. HSCs and MSCs were given as a co-infusion 24 h after irradiative myeloablative conditioning (3.0 Gy), and human HSC colony-forming units in culture (CFUs) were evaluated 7 days after (on day 8) donor HSC engraftment in BMs. Co-administration of MSCs did not affect the general biodistribution patterns of donor HSCs (data not shown). After extraction of femoral BMs, the mononuclear cell faction recovered from all large-MSC treated mice groups (large-MSCs and large-MSC+HSC co-infusions) were significantly higher than those from other treatment groups (FIG. 4H); this was evidence of the enhanced homing, engraftment and survivability of donor HSCs in large-MSC conditioned BMs. Human specific HSC CFU assays in methycellulose were performed using equal numbers of recovered mononuclear cells, and the results are shown in FIGS. 4I and 4J. The highest numbers of total CFUs and multifunctional CFU-GEMMs were found in cultures containing cells from the large-MSC group, demonstrating the ability of these mice in sustaining donor HSC repopulation potentials. Together, these results showed that large-MSC mediated regeneration of BM tissue after irradiative myeloablation created a supportive BM tissue environment for donor HSCs to home, engraft, survive and maintain their repopulation potentials most effectively.

No Difference in Direct HSC Stimulation by Different MSC Fractions

Figures 12A, 12B:
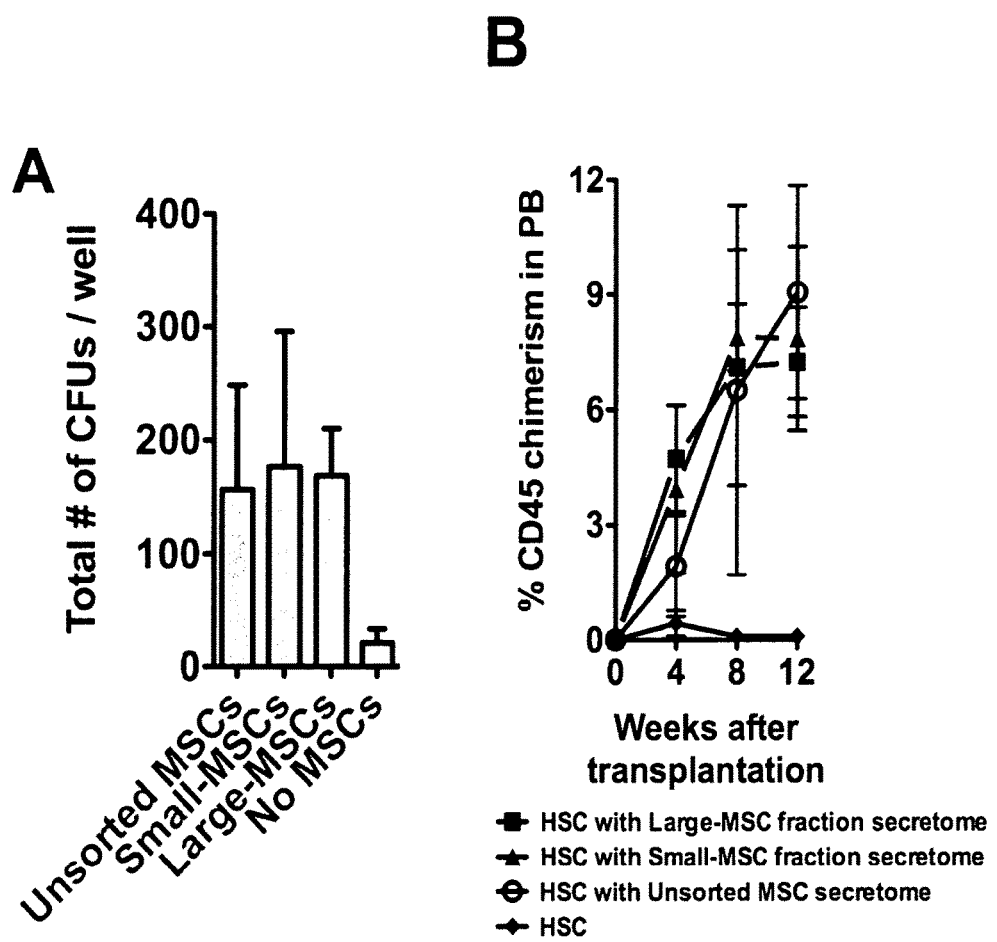
FIG. 12A is a bar graph summarizing the results of a CFU assay in methylcellulose for HSCs exposed to different MSCs as feeder layers under non-contact conditions for a period of 7 days. After 14 days, the numbers of colonies formed were counted from triplicate wells.
FIG. 12B shows human CD45 engraftment in sublethally irradiated NSG mice after non-contact conditioning in FIG. 12A. The secretome from MSC fractions did not differentially affect the engraftment and repopulation potential of the injected HSCs (n=3 mice).
Figure 12C:
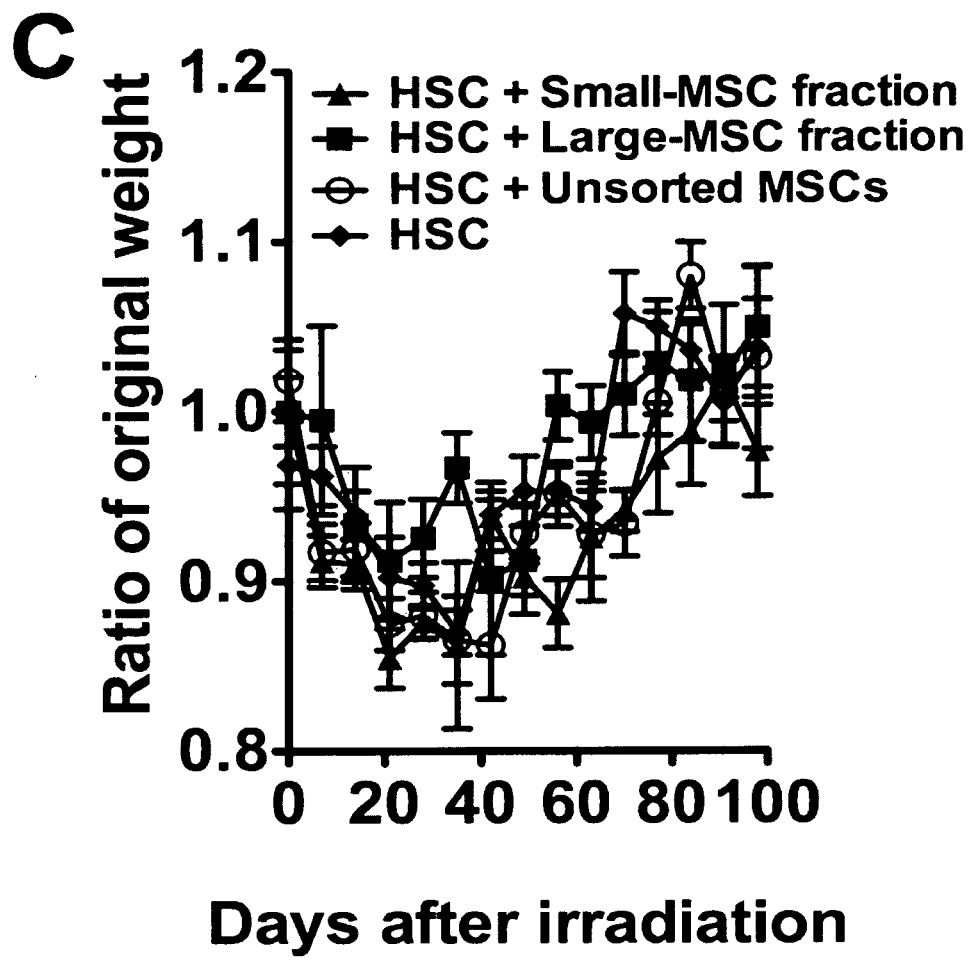
FIG. 12C shows weights of NSG mice undergoing experimental HSC transplants in FIG. 5C. All values are given in mean±sd unless otherwise stated.
Figure 14:
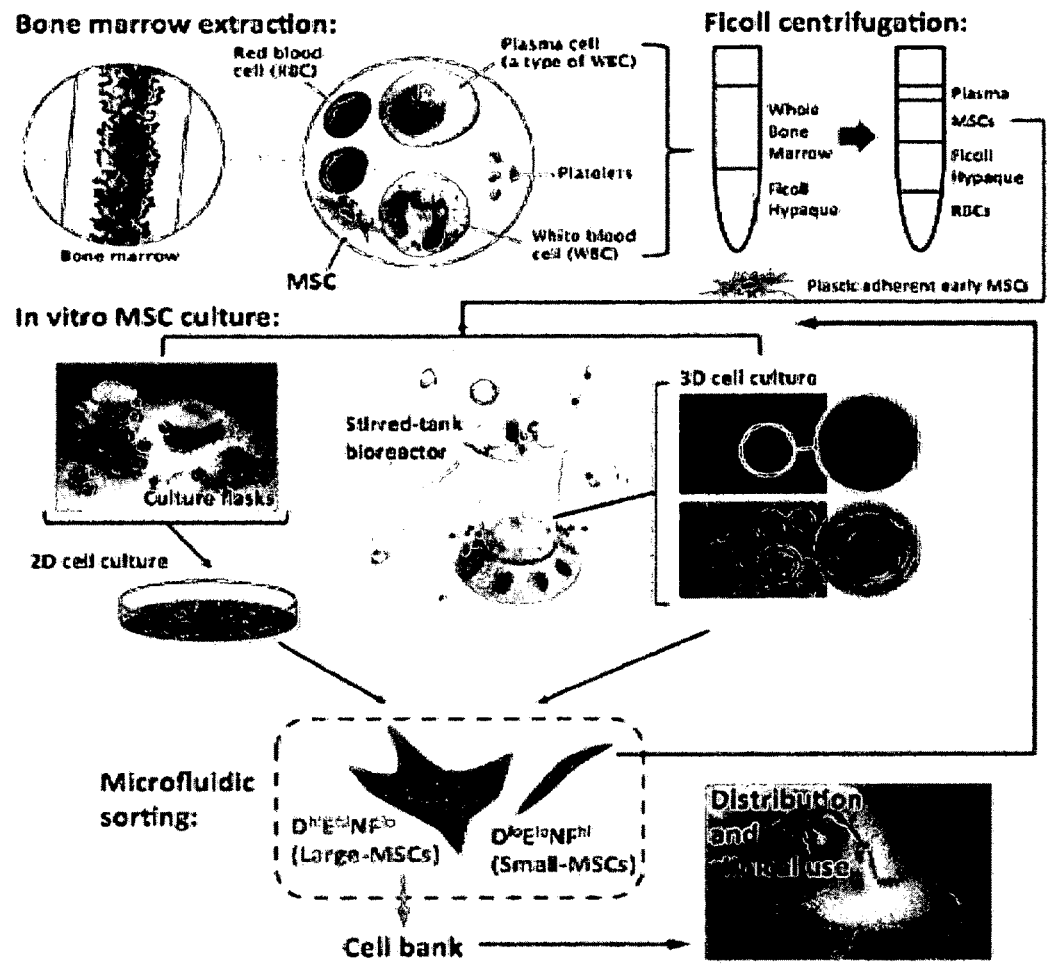
FIG. 14 is a schematic showing a production process of large-MSCs. Bone marrow (BM) MSCs are extracted and regularly expanded in either 2D or 3D culture systems until a later passage. Microfluidic sorting is then applied to extract a large-MSC fraction, which is cryogenically preserved. The small-MSC fraction is returned to culture to generate more large-MSCs at a later passage for extraction. In this manner, large-MSCs are continually extracted and banked for therapy.
Figure 15A:
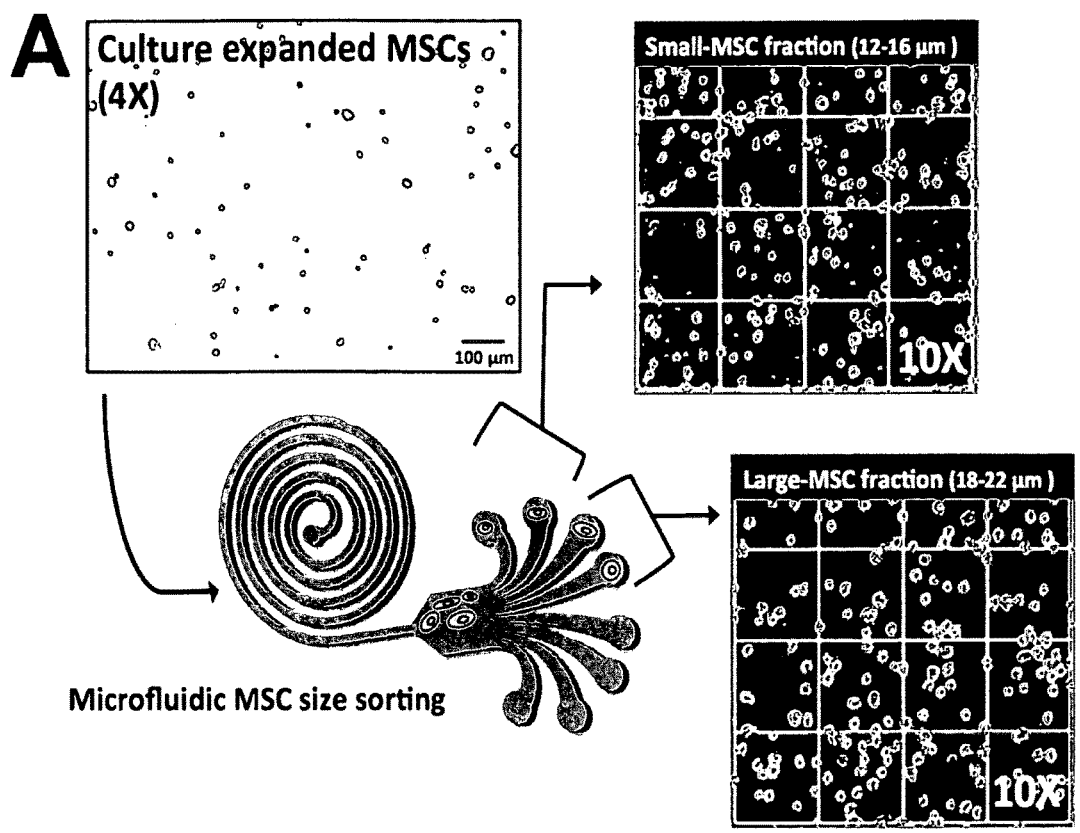
FIGS. 15A-15G show characteristics of the large-MSC fraction.
Figure 15B:
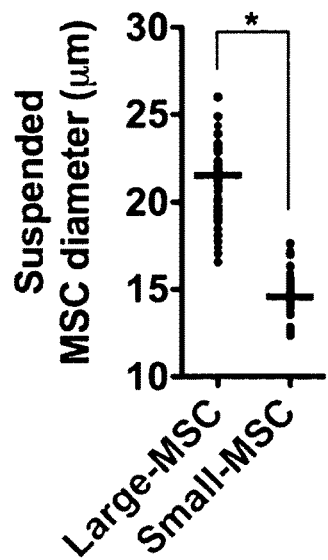
Figure 15C:
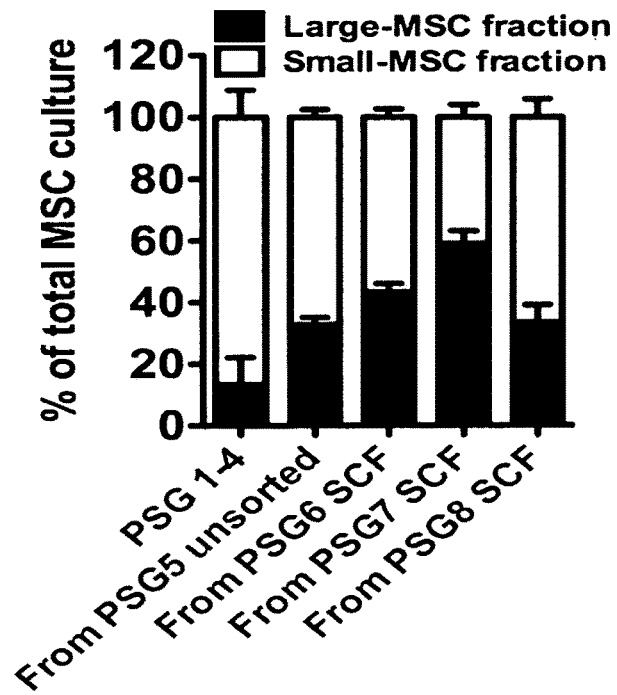
Figure 15D:
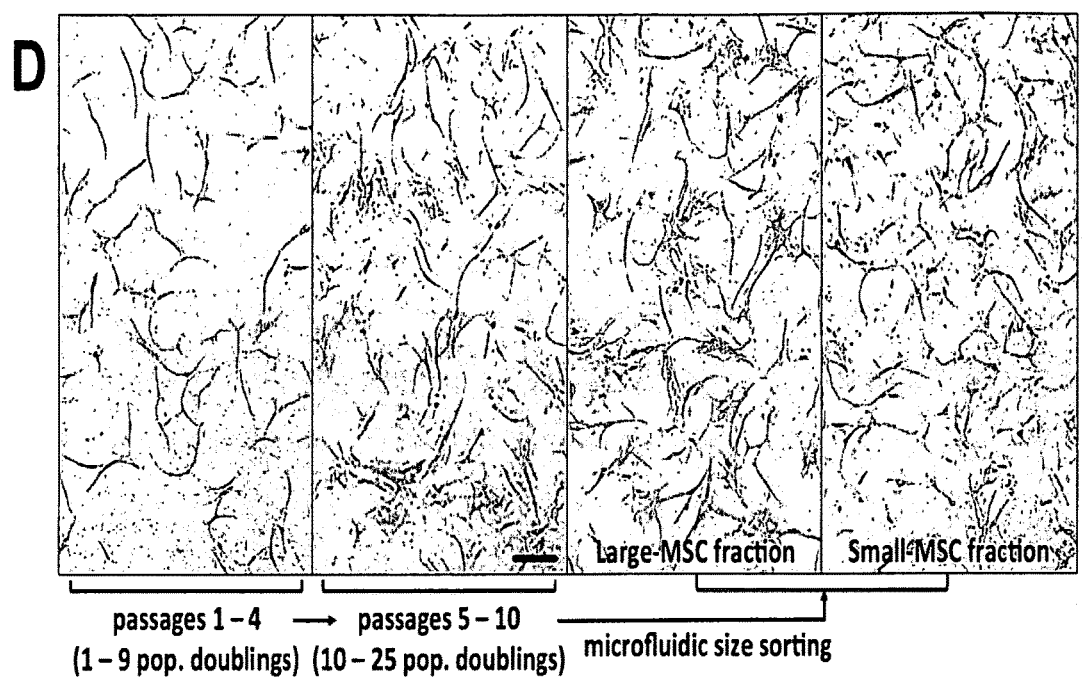
Figure 15E:
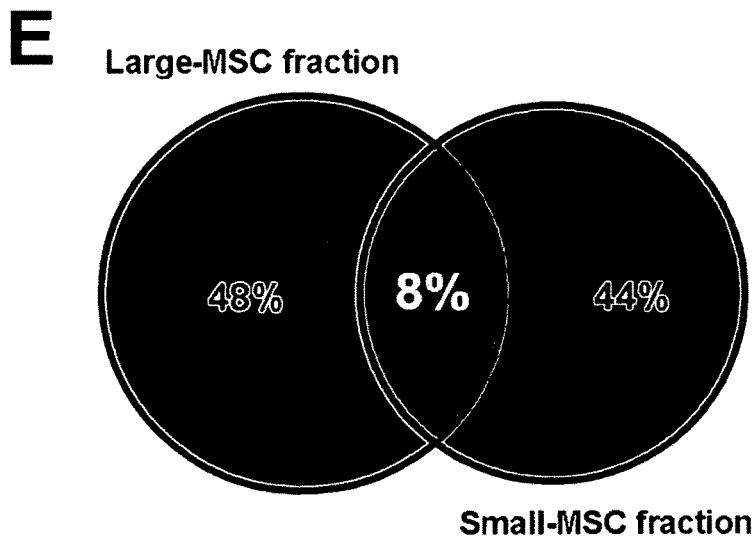
Figure 15F:
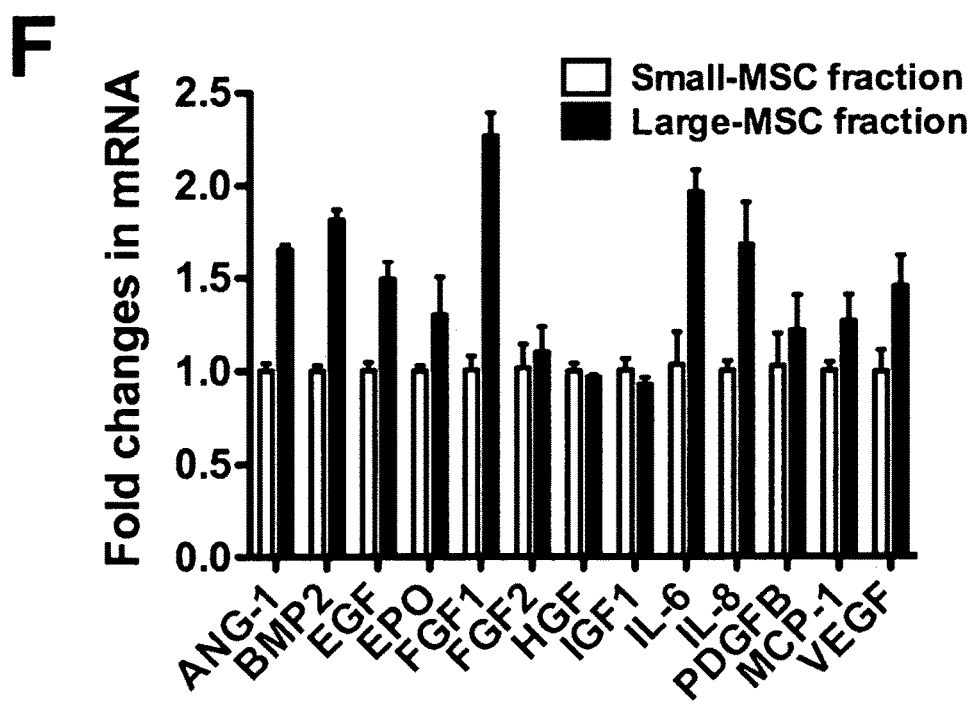
Figure 15G:
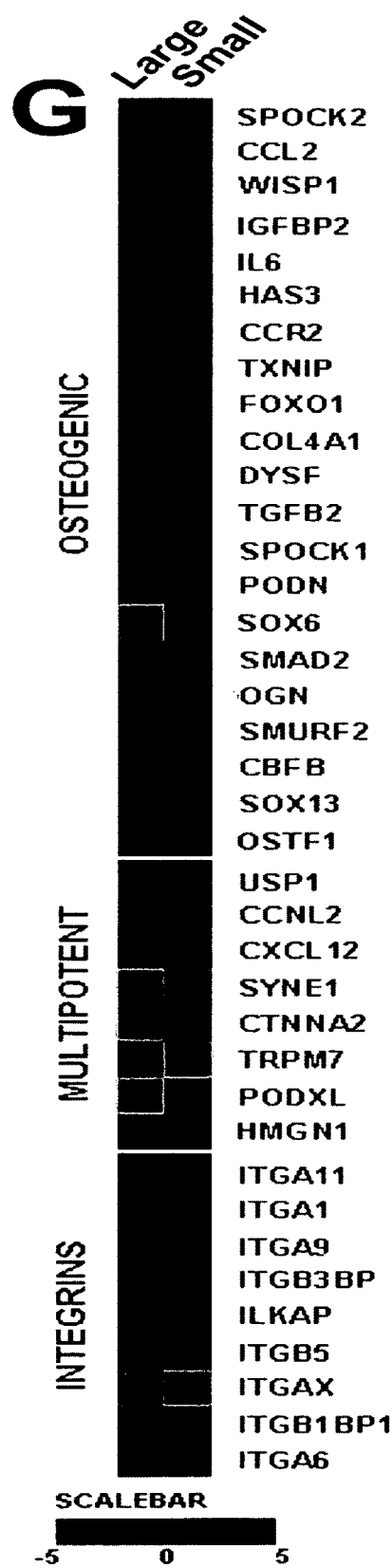
Figure 16A:
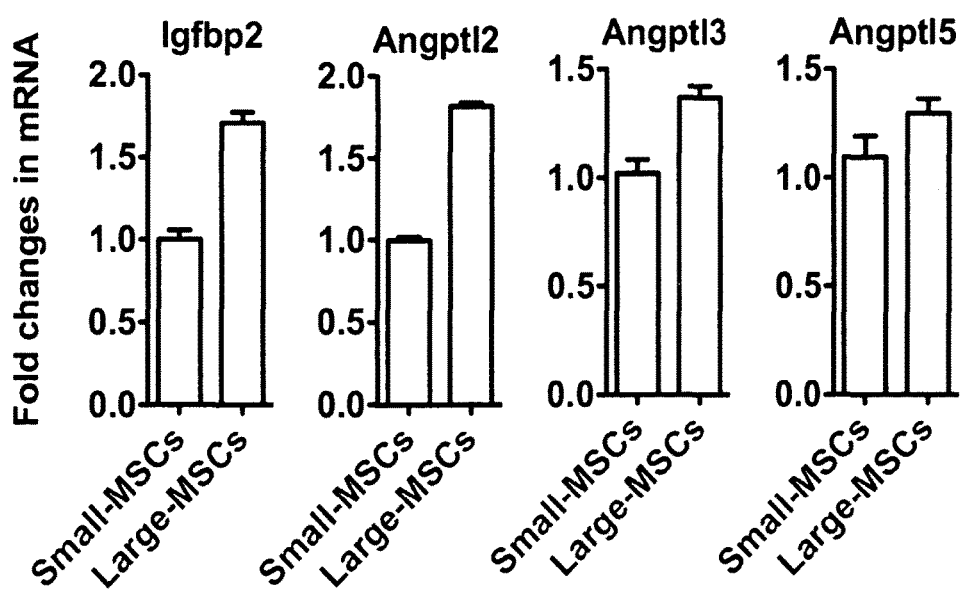
FIG. 16A is an RTPCR analysis of the expression of Igfbp2, Angptl2, Angptl3, and Angptl4 in large- and small-MSC fractions. These data are normalized to GAPDH. The large-MSC population therefore exhibits upregulation of proteins related to their secretory profile. In particular, Igfbp2 and Angptl5 can be used to supplement culture expansion of hematopoietic stem cell (HSC) in vitro, thereby augmenting and/or promoting the efficacy of HSC transplantation.

Hematopoietic growth factors secreted by injected MSCs in vivo could enhance the survivability and engraftment of donor HSCs. It was therefore investigated whether hematopoietic factors secreted by different MSC fractions could provide a repopulative advantage to the injected HSCs. In vitro CFU assays were performed on HSCs that were exposed to the secretome of different MSC fractions (non-contact cultures) for a period of 7 days, corresponding to a sufficiently similar period of time in our in vivo models for donor HSCs to be affected by MSC derived growth factors after their co-injection (MSCs are undetected in mice by day 10). Compared to unsupplemented media, the secretome from all MSC fractions supported increased HSC CFU formation in vitro and repopulation in vivo; no significant differences were found between the ability of different MSC fraction secretomes for affecting HSC CFU formation or for improving donor cell engraftment and chimerism in long-term in vivo repopulation assays (FIGS. 12A and 12B). We also found no meaningful differences between secreted levels of hematopoietic factors like SDF-1a and TPO between the large- and small-MSC fractions (FIG. 3E). These results indicated that MSCs generally improved donor HSC repopulation dynamics, but the large- and small-MSC fraction secretome do not differentially affect HSC repopulation capabilities through direct stimulation of HSCs.

Enhanced Early Reconstitution Kinetics with Large-MSC Co-Injections

Figure 5A:
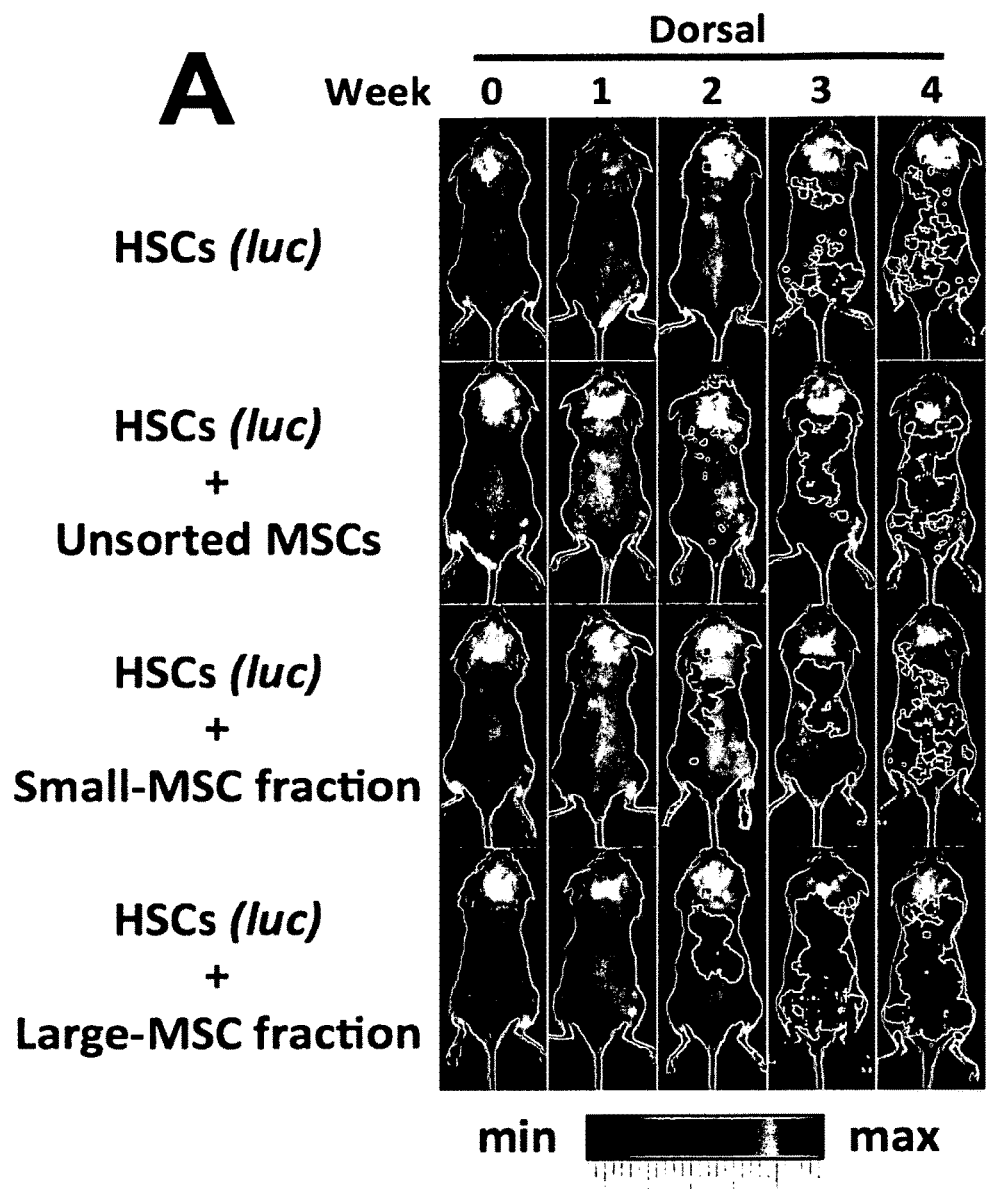
FIGS. 5A-5F show that large-MSC co-injection leads to faster donor HSC repopulation kinetics. Myeloablated NSGs (3.0 Gy) were infused with a co-injection of human HSCs and different MSCs 24 after the procedure.
Figure 5B:
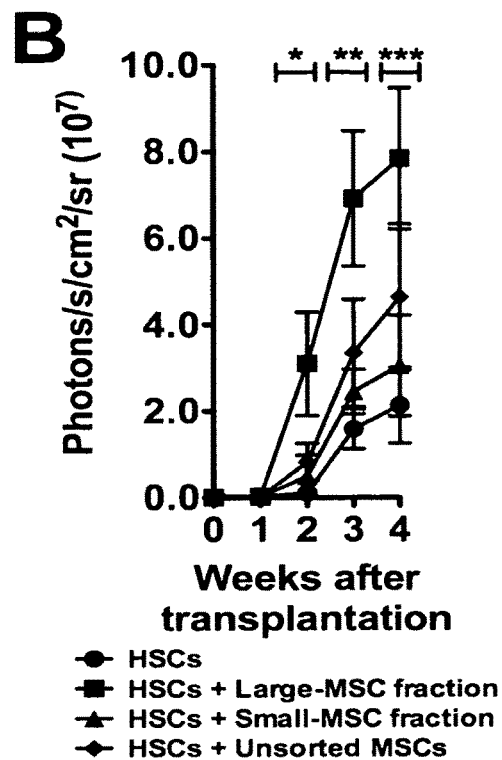
Figure 5C:
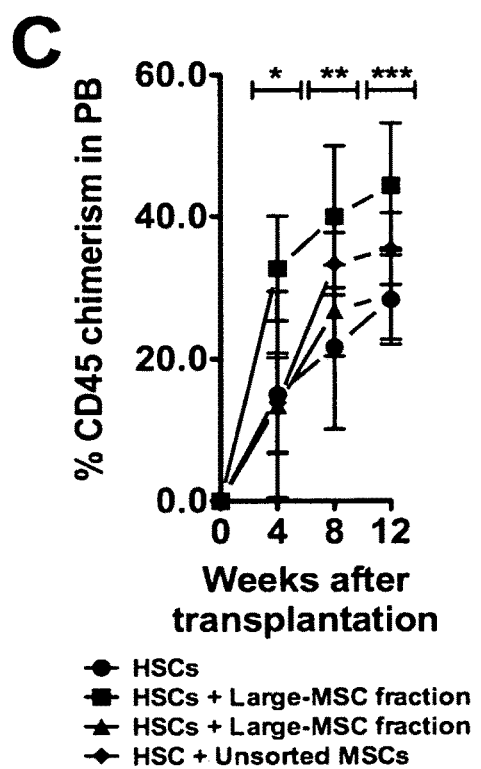

Encouraged by the increased homing of donor HSCs to large-MSC treated BMs, it was subsequently investigated whether this would lead to improvements in long-term HSC engraftment and reconstitution kinetics. After sublethal irradiation of NSG mice (3.0 Gy), the following treatments were investigated: 1) HSCs, 2) HSCs and unsorted MSCs (PSG 6), 3) HSCs and small-MSC fraction (PSG 6), and 4) HSCs and large-MSC fraction (PSG 6). HSCs and MSCs were given as co-injections 24 h after irradiation at doses of 5 million/Kg and 25 million/Kg, respectively. Initially, HSC engraftment and repopulation kinetics were examined using luciferase-transformed CD34+Lin-human HSCs and whole body bioluminescence imaging. Over a period of 2-3 weeks after treatment, we observed a steady increase in whole body bioluminescence originating from anatomic sites corresponding to the spine and femurs; this increase in signal was most pronounced in the large-MSC adjuvant therapy group (~3-4× increase by week 3, FIGS. 5A and 5B) but was significantly slower in other treatment groups. These trends were consistent in a separate set of experiments examining donor HSC engraftment via the level of human CD45 chimerism after transplantation (FIG. 5C); however, the most pronounced effect of large-MSCs on HSC engraftment was observed in the earlier time points (<1 month) after transplantation. These data showed significantly rapid and higher HSC engraftment rates for large-MSC treatment groups at week 4, but reconstitution levels became statistically indifferent from other treatment groups after 4 weeks (FIG. 5C).

Figure 5D:
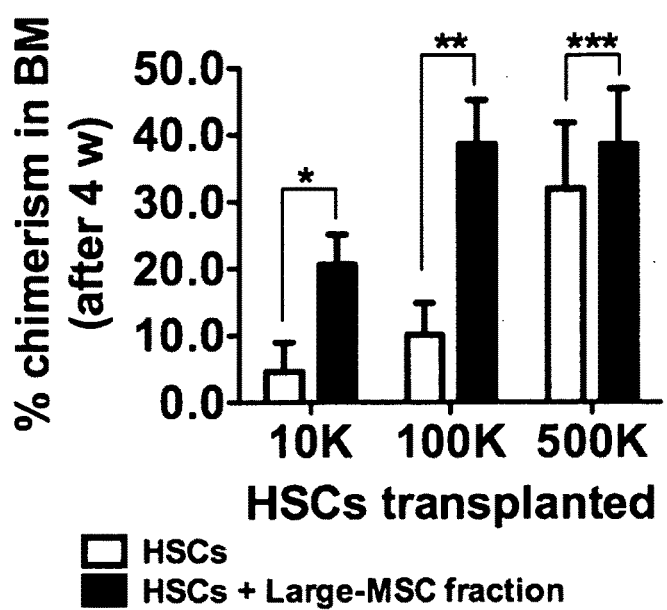
Figure 5E:
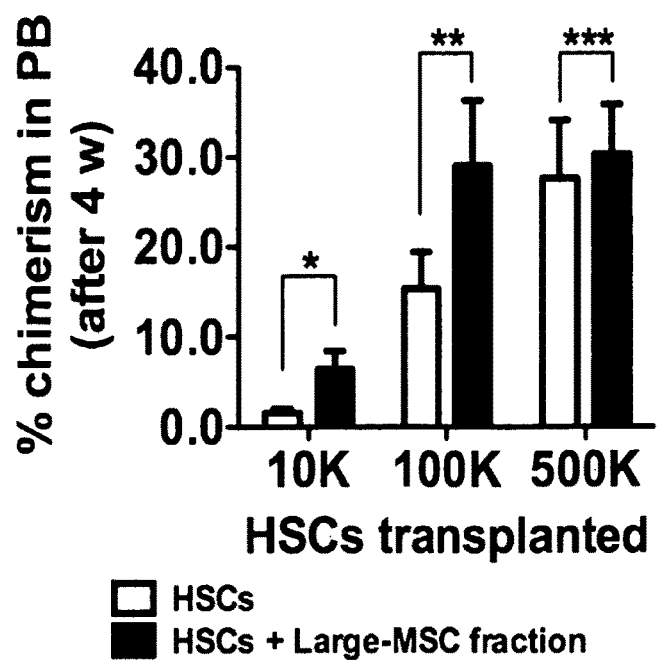
Figure 5F:
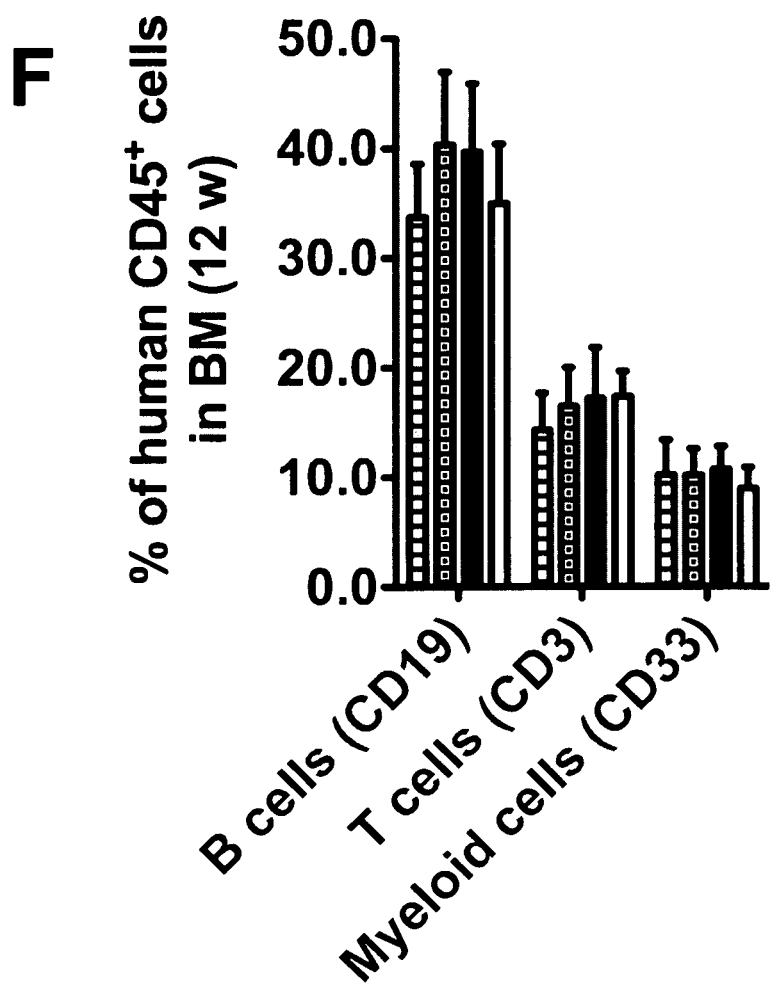

Large-MSC mediated enhancements in HSC engraftment were also more prominent at lower HSC doses. FIGS. 5D and 5E show the levels of CD45 chimerism in the BM and peripheral blood 4 weeks after large-MSCs were co-administered with varying numbers of HSCs. Engraftment in both the BM and peripheral blood was only significantly different at HSC doses less than 100K. Although large-MSC co-administration increased the initial rate of HSC engraftment and repopulation kinetics, it did not affect their multilineage differentiation potential and the engraftment enhancing effect of large-MSCs was also not lineage restricted (FIG. 5F).

Discussion

The demonstration of consistent and high levels of therapeutic efficacy from readily available sources remains a central challenge for MSC-based medicines. However, subtle differences in donor, source, culture methods and expansion levels can affect the nature of the final MSC culture. To realize the potential of MSC-based therapies, the variable efficacies of the final culture expanded product must be addressed. Heuristic failure analyses of the largest clinical experiences to date show that even when the consistency of MSC biology is maintained with similar MSC harvesting procedures, the process of culture expansion introduces artifacts that greatly affect the quality of the expanded cells. From a stem cell biology perspective, genetic re-programming inexorably occurs when somatic stem cells, which inherently exhibit genetic plasticity, are impelled to proliferate extensively under artificial selection pressures to achieve a cell quantity large enough for clinical or industrial use. Expansion pressures lead to clonal impoverishment, lineage commitment and a resultant biology that is significantly different not only from that of the initial MSCs, but also between culture expanded cells. Thus, a heterogeneous mixture of MSCs is produced, making it difficult to engineer consistent therapy.

Here, a cell sorting strategy for expanded MSC cultures that can homogenize their therapeutic properties and deliver consistency in medical applications was devised. Through new understanding of the mechanisms governing MSC-induced tissue regeneration, it was experimentally shown that osteoprogenitor MSCs, instead of uncommitted MSCs within the same BM mixture, stimulated repair for injured tissues most effectively via secretion of a cocktail of relevant growth factors. Although this has been alluded to in other investigations of BM repair, it has yet to be translated into a viable form of therapy. This delayed realization is due to the impracticality of extracting osteoprogenitors/osteoblasts from BM as well as a general dearth of studies examining subpopulation cell properties in expanded cultures that may lead to new discoveries for their use. Label-free biophysical cell sorting also adds to the attractiveness of this approach, as technical and regulatory complications arising from traditional antibody selection or other biochemical modifications of the cells are avoided.

Compared to other treatment groups, systemic administration of the osteoprogenitor-enriched large-MSC fraction resulted in enhanced regeneration of BM tissue and increased survival times after irradiative damage. There was no evidence of any long-term MSC engraftment within the BM tissue and further experiments demonstrated that regular injections of conditioned media from the large-MSC fraction partially reproduced the effect of cell-injections. These observations, together with data showing the increased capabilities of the large-MSC fraction for secreting regenerative factors, are consistent with other MSC studies and support the notion that large-MSCs also function primarily as "cell factories" after systemic injection to mediate tissue repair. The multitude of beneficial factors secreted by large-MSCs has the potential to modulate the injured cellular milieu on multiple fronts to evoke sustained and enhanced tissue regeneration. Large-MSCs represent a natural systems-based therapy for tissue repair across immunological barriers; clinical data to date support the long-term safety profile of systematically delivered MSC therapy for the treatment of various diseases. As much as $10^6$ MSCs/kg from non-related donors have been administered without long-term complications. This generates a high level of enthusiasm within the scientific and medical communities for the continued development of adult MSC-based therapies, as they are a preferred stem cell therapy over embryonic or fetal stem cell sources. Furthermore, the demonstrated safety profile of adult MSCs from unrelated donors paves the way for the use of pre-manufactured, cryopreserved MSCs from a larger donor pool, which would greatly facilitate the widespread use of this living therapeutic.

In the second part of this study, applications of the large-MSCs for HSCT were demonstrated. HSCT involves a preparative conditioning regimen consisting of total body irradiation (TBI), chemotherapy, or a combination of both to provide adequate immunosuppression to prevent early rejection of transplanted cells, to eradicate malignant cells prior to transplant and to ablate the BM of hematopoietic cells to make room for the donor cells. Shortly after the conclusion of conditioning therapy, ex vivo preserved HSCs, autologous or allogeneic, HLA-matched or mismatched, are then given to the patient as an infusion to re-establish hematopoietic function. The post-treatment period is generally associated with a substantial level of morbidity and mortality. Typical complications include decreased cardiovascular and respiratory capacity, muscle weakness, fatigue, pain, gastrointestinal problems and the loss of appetite. Patients therefore require prolonged convalescence, especially if they are also affected by additional toxicities related to cytotoxic conditioning (hepatic venoocclusive disease, cardiotoxicity, neutropenia) or allo-reactivity of donor cells (graft-vs-host disease). Together, the continued decline in physical status as a result of transplant complications can ultimately be life threatening and additional steps towards de-risking this costly procedure will have significant impact on refining HSCT to support its use for an even broader range of indications. A great number of approaches for managing these procedures are HSC-centric in nature, in that they rely on growth factors to boost HSC function, or on methods for enhancing the quality of injected donor HSCs to resist immune rejection and to possess the greatest possible "stem-like" capabilities for long-term multilineage reconstitution in the host body. However, retrospective clinical data show that these HSC-centric approaches have limited utility, particularly in HSCT procedures for patients receiving cord blood HSCT, a second HSCT, or haploidentical HSCT. To compensate for known inefficacies in engraftment, large numbers of cells are administered, but even this last-ditch attempt is inefficient for a significant number of high-risk patients. These observations, together with laboratory data, demonstrate that HSC quality is not the only deterministic parameter on the outcome of a transplant. The state of the host BM tissue environment, specifically, its vascular structural integrity and functionality of associated niche cells, also contributes to donor HSC homing, engraftment, integration and survival to influence the outcome of HSCT and, additionally, also plays an important role in graft function even after HSCT. Thus, large-MSC based strategies aimed at manipulating the recovery of the BM after myeloablation can be particularly impactful for fostering tissue environments conducive for HSC engraftment.

It was found that co-transplantation of large-MSCs and hematopoietic stem/progenitor cells resulted in significantly higher engraftment and initial reconstitution rates than was observed after co-transplantation with small-MSCs or unsorted MSCs. Homing studies showed higher levels of donor HSC levels in the BM after co-injections with large-MSCs, and subsequent CFU assays on the engrafted donor cells, together with long-term donor HSC repopulation studies, confirmed the hematopoietic transplant advantage when large-MSCs are used as co-therapy. Taken together, large-MSC based therapy for regenerating the BM stroma addresses unmet challenges for more effective management of hematologic diseases and can also work cooperatively with existing HSC-centric treatments towards better patient health. These cells can be administered as adjuvant therapy in HSCT applications, or used as treatment for patients that suffer from long-term hematopoietic disorder as a result of intensive chemo- or radio-anticancer treatment.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of producing an MSC population with enhanced regenerative potential, comprising:
   a) culturing an MSC-containing population of cells in a culture medium to a confluence of 80% to 90% over each of at least four population doublings to provide a population enriched in large-MSC cells, wherein the four population doublings are measured from initial extraction of the MSC-containing population from a source; and
   b) biophysically sorting the MSC-containing population of cells produced in (a) and collecting a large-MSC population of cells from the MSC-containing population, thereby producing an MSC population with enhanced regenerative potential.

2. The method of claim 1, wherein the biophysical sorting of the MSC-containing population comprises applying the MSC-containing population of cells to an inlet of an MSC-dimensioned microfluidic device and collecting a large-MSC population of cells from an outlet of the MSC-dimensioned microfluidic device.

3. The method of claim 1, further comprising culturing the large-MSC population.

4. The method of claim 3, comprising collecting conditioned medium from the large-MSC culture.

5. The method of claim 4, wherein the large-MSC culture medium contains increased amounts of one or more of IL-6, IL-8, MCP-1, EGF, VEGF, FGF1, FGF2, BMP2, ANG1, osteopontin, Igfbp2, Angptl2, Angptl3, and Angptl5 compared to a culture medium obtained from small-MSCs.

6. The method of claim 1, further comprising collecting a small-MSC population from an outlet of the MSC-dimensioned microfluidic device.

7. The method of claim 6, further comprising culturing the small-MSC population.

8. The method of claim 7, comprising applying the cultured small-MSC population to an inlet of an MSC-dimensioned microfluidic device and collecting a large-MSC population from an outlet of the MSC-dimensioned microfluidic device.

9. The method of claim 1, wherein the MSC-containing population of cells is obtained from bone marrow, is a cultured MSC-containing population of cells or an uncultured MSC-containing population of cells.

10. The method of claim 1, further comprising trypsinizing the MSC-containing population of cells after the MSC-containing population of cells has been cultured to a confluence of 80% to 90%.

11. The method of claim 10, wherein trypsinizing is performed after each of the at least four population doublings.

12. The method of claim 10, further comprising cryopreserving a portion of the MSC-containing population of cells in a cryopreservation medium after trypsinization, after about 4 to about 6 population doublings or after about 12 population doublings.

13. The method of claim 1, wherein the biophysical sorting has a throughput of at least about $10^3$ cells/minute, or about $1\text{-}5\times 10^6$ cells/minute.

14. A method of culturing an MSC-containing population cells to produce an MSC population with enhanced regenerative potential, comprising:
   a) culturing an MSC-containing population of cells in a culture medium to a confluence of 80% to 90%;
   b) optionally trypsinizing the MSC-containing population of cells;
   c) repeating a) and b) so that the MSC-containing population of cells doubles at least four times, as measured from initial extraction of the MSC-containing population from a source, to thereby produce an MSC population with enhanced regenerative potential; and
   d) optionally cryopreserving a portion of the MSC-containing population of cells in a cryopreservation medium after one or more population doublings.

15. The method of claim 14, wherein the MSC-containing population of cells is obtained from bone marrow.

16. The method of claim 14, wherein a portion of the MSC-containing population of cells is cryopreserved after about four to six population doublings.

17. The method of claim 16, wherein a portion of the MSC-containing population of cells is cryopreserved after about twelve population doublings.

18. The method of claim 16, wherein the cryopreservation medium comprises Dulbecco's Modified Eagle's Medium, fetal bovine serum, and dimethyl sulfoxide.

19. The method of claim 16, wherein the cryopreservation medium consists essentially of 70% Dulbecco's Modified Eagle's Medium Low Glucose, 20% fetal bovine serum, and 10% dimethyl sulfoxide.

20. A method of producing an MSC population with enhanced regenerative potential, comprising:
   a) culturing an MSC-containing population of cells in a culture medium to a confluence of 80% to 90% over each of at least four population doublings to provide a population enriched in large-MSC cells, wherein the four population doublings are measured from initial extraction of the MSC-containing population from a source, wherein the MSC-containing population of cells are seeded, initially and at subsequent passages, at about 1000 MSC/cm$^2$ to 1500 MSC/cm$^2$; and
   b) biophysically sorting the MSC-containing population of cells produced in (a) and collecting a large-MSC population of cells from the MSC-containing population, thereby producing an MSC population with enhanced regenerative potential.

* * * * *

SEQUENCE LISTING

<160> NUMBER OF SEQ ID NOS: 42

<210> SEQ ID NO 1
<211> LENGTH: 18
<212> TYPE: DNA
<213> ORGANISM: Artifical Sequence
<220> FEATURE:
<223> OTHER INFORMATION: Primer

<400> SEQUENCE: 1
caaggctgtg ggcaaggt                                             18

<210> SEQ ID NO 2
<211> LENGTH: 18
<212> TYPE: DNA
<213> ORGANISM: Artifical Sequence
<220> FEATURE:
<223> OTHER INFORMATION: Primer

<400> SEQUENCE: 2
ggaaggccat gccagtga                                             18

<210> SEQ ID NO 3
<211> LENGTH: 20
<212> TYPE: DNA
<213> ORGANISM: Artifical Sequence
<220> FEATURE:
<223> OTHER INFORMATION: Primer

<400> SEQUENCE: 3
cgaatggcag cacgctatta                                           20

<210> SEQ ID NO 4
<211> LENGTH: 19
<212> TYPE: DNA
<213> ORGANISM: Artifical Sequence
<220> FEATURE:
<223> OTHER INFORMATION: Primer

<400> SEQUENCE: 4
tggcttccat cagcgtcaa                                            19

<210> SEQ ID NO 5
<211> LENGTH: 19
<212> TYPE: DNA
<213> ORGANISM: Artifical Sequence
<220> FEATURE:
<223> OTHER INFORMATION: Primer

<400> SEQUENCE: 5
cgggaccaga ctcgtctca                                            19

<210> SEQ ID NO 6
<211> LENGTH: 18
<212> TYPE: DNA
<213> ORGANISM: Artifical Sequence
<220> FEATURE:
<223> OTHER INFORMATION: Primer

<400> SEQUENCE: 6
ttccttggtc ggcgtttg                                             18

<210> SEQ ID NO 7
<211> LENGTH: 20
<212> TYPE: DNA
<213> ORGANISM: Artifical Sequence

```
<220> FEATURE:
<223> OTHER INFORMATION: Primer

<400> SEQUENCE: 7
tccacagcct ttgtgtccaa                                               20

<210> SEQ ID NO 8
<211> LENGTH: 20
<212> TYPE: DNA
<213> ORGANISM: Artifical Sequence
<220> FEATURE:
<223> OTHER INFORMATION: Primer

<400> SEQUENCE: 8
gcgcctgggt ctcttcacta                                               20

<210> SEQ ID NO 9
<211> LENGTH: 20
<212> TYPE: DNA
<213> ORGANISM: Artifical Sequence
<220> FEATURE:
<223> OTHER INFORMATION: Primer

<400> SEQUENCE: 9
gctctgctcc aagcgcttta                                               20

<210> SEQ ID NO 10
<211> LENGTH: 18
<212> TYPE: DNA
<213> ORGANISM: Artifical Sequence
<220> FEATURE:
<223> OTHER INFORMATION: Primer

<400> SEQUENCE: 10
ggtgcgctgg tgtttgct                                                 18

<210> SEQ ID NO 11
<211> LENGTH: 18
<212> TYPE: DNA
<213> ORGANISM: Artifical Sequence
<220> FEATURE:
<223> OTHER INFORMATION: Primer

<400> SEQUENCE: 11
tcagggctgc cagtttcg                                                 18

<210> SEQ ID NO 12
<211> LENGTH: 24
<212> TYPE: DNA
<213> ORGANISM: Artifical Sequence
<220> FEATURE:
<223> OTHER INFORMATION: Primer

<400> SEQUENCE: 12
gcttttggca tactctgtga tctc                                          24

<210> SEQ ID NO 13
<211> LENGTH: 14
<212> TYPE: DNA
<213> ORGANISM: Artifical Sequence
<220> FEATURE:
<223> OTHER INFORMATION: Primer

<400> SEQUENCE: 13
ccgggcccgc gtat                                                     14
```

<210> SEQ ID NO 14
<211> LENGTH: 20
<212> TYPE: DNA
<213> ORGANISM: Artifical Sequence
<220> FEATURE:
<223> OTHER INFORMATION: Primer

<400> SEQUENCE: 14
tcctgctcgt cggtcatctt                                           20

<210> SEQ ID NO 15
<211> LENGTH: 20
<212> TYPE: DNA
<213> ORGANISM: Artifical Sequence
<220> FEATURE:
<223> OTHER INFORMATION: Primer

<400> SEQUENCE: 15
agggctcttc ggcaaatgta                                           20

<210> SEQ ID NO 16
<211> LENGTH: 23
<212> TYPE: DNA
<213> ORGANISM: Artifical Sequence
<220> FEATURE:
<223> OTHER INFORMATION: Primer

<400> SEQUENCE: 16
gaaggaatgc ccattaacaa caa                                       23

<210> SEQ ID NO 17
<211> LENGTH: 20
<212> TYPE: DNA
<213> ORGANISM: Artifical Sequence
<220> FEATURE:
<223> OTHER INFORMATION: Primer

<400> SEQUENCE: 17
caccggaagg aaccatctca                                           20

<210> SEQ ID NO 18
<211> LENGTH: 17
<212> TYPE: DNA
<213> ORGANISM: Artifical Sequence
<220> FEATURE:
<223> OTHER INFORMATION: Primer

<400> SEQUENCE: 18
agagccacgg ccagctt                                              17

<210> SEQ ID NO 19
<211> LENGTH: 18
<212> TYPE: DNA
<213> ORGANISM: Artifical Sequence
<220> FEATURE:
<223> OTHER INFORMATION: Primer

<400> SEQUENCE: 19
cgagggcctg gagtgtgt                                             18

<210> SEQ ID NO 20
<211> LENGTH: 21
<212> TYPE: DNA
<213> ORGANISM: Artifical Sequence
<220> FEATURE:
<223> OTHER INFORMATION: Primer

<400> SEQUENCE: 20
cgcataatct gcatggtgat g                                    21

<210> SEQ ID NO 21
<211> LENGTH: 25
<212> TYPE: DNA
<213> ORGANISM: Artifical Sequence
<220> FEATURE:
<223> OTHER INFORMATION: Primer

<400> SEQUENCE: 21
tccaggttat cccagagatt taatg                                25

<210> SEQ ID NO 22
<211> LENGTH: 20
<212> TYPE: DNA
<213> ORGANISM: Artifical Sequence
<220> FEATURE:
<223> OTHER INFORMATION: Primer

<400> SEQUENCE: 22
gggcttttgg tgggagaagt                                      20

<210> SEQ ID NO 23
<211> LENGTH: 20
<212> TYPE: DNA
<213> ORGANISM: Artifical Sequence
<220> FEATURE:
<223> OTHER INFORMATION: Primer

<400> SEQUENCE: 23
aaagggcatc ctctccacaa                                      20

<210> SEQ ID NO 24
<211> LENGTH: 18
<212> TYPE: DNA
<213> ORGANISM: Artifical Sequence
<220> FEATURE:
<223> OTHER INFORMATION: Primer

<400> SEQUENCE: 24
aggcgtttcc gctgtttg                                        18

<210> SEQ ID NO 25
<211> LENGTH: 23
<212> TYPE: DNA
<213> ORGANISM: Artifical Sequence
<220> FEATURE:
<223> OTHER INFORMATION: Primer

<400> SEQUENCE: 25
tgtaaaaaca cccctggatc cta                                  23

<210> SEQ ID NO 26
<211> LENGTH: 21
<212> TYPE: DNA
<213> ORGANISM: Artifical Sequence
<220> FEATURE:
<223> OTHER INFORMATION: Primer

<400> SEQUENCE: 26
cccatcagga agcagaacaa a                                    21

<210> SEQ ID NO 27

<210> SEQ ID NO 27
<211> LENGTH: 19
<212> TYPE: DNA
<213> ORGANISM: Artifical Sequence
<220> FEATURE:
<223> OTHER INFORMATION: Primer

<400> SEQUENCE: 27
gcccagagca ggaagcatt                                                19

<210> SEQ ID NO 28
<211> LENGTH: 20
<212> TYPE: DNA
<213> ORGANISM: Artifical Sequence
<220> FEATURE:
<223> OTHER INFORMATION: Primer

<400> SEQUENCE: 28
tcttcccagc atggctctgt                                               20

<210> SEQ ID NO 29
<211> LENGTH: 23
<212> TYPE: DNA
<213> ORGANISM: Artifical Sequence
<220> FEATURE:
<223> OTHER INFORMATION: Primer

<400> SEQUENCE: 29
gtttaatctg cctccaggga att                                           23

<210> SEQ ID NO 30
<211> LENGTH: 17
<212> TYPE: DNA
<213> ORGANISM: Artifical Sequence
<220> FEATURE:
<223> OTHER INFORMATION: Primer

<400> SEQUENCE: 30
agtggccccc gttgcta                                                  17

<210> SEQ ID NO 31
<211> LENGTH: 23
<212> TYPE: DNA
<213> ORGANISM: Artifical Sequence
<220> FEATURE:
<223> OTHER INFORMATION: Primer

<400> SEQUENCE: 31
aatcaaaagt tcggcatgta gct                                           23

<210> SEQ ID NO 32
<211> LENGTH: 20
<212> TYPE: DNA
<213> ORGANISM: Artifical Sequence
<220> FEATURE:
<223> OTHER INFORMATION: Primer

<400> SEQUENCE: 32
ctgagcaggg cagatttgct                                               20

<210> SEQ ID NO 33
<211> LENGTH: 21
<212> TYPE: DNA
<213> ORGANISM: Artifical Sequence
<220> FEATURE:
<223> OTHER INFORMATION: Primer

<400> SEQUENCE: 33
tctggttccc cttcaatagc a    21

<210> SEQ ID NO 34
<211> LENGTH: 22
<212> TYPE: DNA
<213> ORGANISM: Artifical Sequence
<220> FEATURE:
<223> OTHER INFORMATION: Primer

<400> SEQUENCE: 34
ggtcaaattc atggccaaat tc    22

<210> SEQ ID NO 35
<211> LENGTH: 21
<212> TYPE: DNA
<213> ORGANISM: Artifical Sequence
<220> FEATURE:
<223> OTHER INFORMATION: Primer

<400> SEQUENCE: 35
cctctcaaga gccacaaatg c    21

<210> SEQ ID NO 36
<211> LENGTH: 20
<212> TYPE: DNA
<213> ORGANISM: Artifical Sequence
<220> FEATURE:
<223> OTHER INFORMATION: Primer

<400> SEQUENCE: 36
tccagcagcc aagattcaga    20

<210> SEQ ID NO 37
<211> LENGTH: 22
<212> TYPE: DNA
<213> ORGANISM: Artifical Sequence
<220> FEATURE:
<223> OTHER INFORMATION: Primer

<400> SEQUENCE: 37
caagcagaag tgggttcagg at    22

<210> SEQ ID NO 38
<211> LENGTH: 20
<212> TYPE: DNA
<213> ORGANISM: Artifical Sequence
<220> FEATURE:
<223> OTHER INFORMATION: Primer

<400> SEQUENCE: 38
tcttcggagt ttgggtttgc    20

<210> SEQ ID NO 39
<211> LENGTH: 23
<212> TYPE: DNA
<213> ORGANISM: Artifical Sequence
<220> FEATURE:
<223> OTHER INFORMATION: Primer

<400> SEQUENCE: 39
atcgccatct tcttccctta act    23

<210> SEQ ID NO 40
<211> LENGTH: 21
<212> TYPE: DNA

```
<213> ORGANISM: Artifical Sequence
<220> FEATURE:
<223> OTHER INFORMATION: Primer

<400> SEQUENCE: 40
agagcgaccc catcagtctc t                                              21

<210> SEQ ID NO 41
<211> LENGTH: 22
<212> TYPE: DNA
<213> ORGANISM: Artifical Sequence
<220> FEATURE:
<223> OTHER INFORMATION: Primer

<400> SEQUENCE: 41
agccctgacc actccagttt ag                                             22

<210> SEQ ID NO 42
<211> LENGTH: 24
<212> TYPE: DNA
<213> ORGANISM: Artifical Sequence
<220> FEATURE:
<223> OTHER INFORMATION: Primer

<400> SEQUENCE: 42
ccctctatgg ctgtttcttt ctct                                           24
```